(12) United States Patent
Griffin et al.

(10) Patent No.: US 11,859,007 B2
(45) Date of Patent: *Jan. 2, 2024

(54) HUMANIZED ANTI-CD73 ANTIBODIES

(71) Applicants: Corvus Pharmaceuticals, Inc., Burlingame, CA (US); BioAtla, LLC, San Diego, CA (US)

(72) Inventors: Emily Piccione Griffin, Belmont, CA (US); Richard A. Miller, Portola Valley, CA (US); Gerhard Johann Frey, San Diego, CA (US); Hwai Wen Chang, San Marcos, CA (US)

(73) Assignees: CORVUS PHARMACEUTICALS, INC., Burlingame, CA (US); BIOATLA, INC., San Diego, CA (US)

( * ) Notice: Subject to any disclaimer, the term of this patent is extended or adjusted under 35 U.S.C. 154(b) by 326 days.

This patent is subject to a terminal disclaimer.

(21) Appl. No.: 17/031,297

(22) Filed: Sep. 24, 2020

(65) Prior Publication Data
US 2021/0253727 A1 Aug. 19, 2021

Related U.S. Application Data

(63) Continuation of application No. 16/060,343, filed as application No. PCT/US2016/065968 on Dec. 9, 2016, now Pat. No. 10,822,426.

(60) Provisional application No. 62/346,327, filed on Jun. 6, 2016, provisional application No. 62/289,694, filed on Feb. 1, 2016, provisional application No. 62/265,357, filed on Dec. 9, 2015.

(51) Int. Cl.
| | |
|---|---|
| *C07K 16/28* | (2006.01) |
| *A61K 39/00* | (2006.01) |
| *G01N 33/573* | (2006.01) |
| *G01N 33/84* | (2006.01) |
| *A61P 35/00* | (2006.01) |

(52) U.S. Cl.
CPC .......... *C07K 16/2896* (2013.01); *A61P 35/00* (2018.01); *G01N 33/573* (2013.01); *G01N 33/84* (2013.01); *C07K 2317/24* (2013.01); *C07K 2317/52* (2013.01); *C07K 2317/565* (2013.01); *C07K 2317/71* (2013.01); *C07K 2317/76* (2013.01); *C07K 2317/92* (2013.01); *G01N 2333/916* (2013.01)

(58) Field of Classification Search
None
See application file for complete search history.

(56) References Cited

U.S. PATENT DOCUMENTS

| | | | |
|---|---|---|---|
| 7,456,260 B2 * | 11/2008 | Rybak ................ | C07K 16/2803 536/23.4 |
| 7,994,289 B2 | 8/2011 | Waldmann et al. | |

FOREIGN PATENT DOCUMENTS

| | | | |
|---|---|---|---|
| WO | WO-2008/156712 A1 | 12/2008 | |
| WO | WO-2008156712 A1 * | 12/2008 | .............. A61P 31/00 |
| WO | WO-2009/043933 A1 | 4/2009 | |
| WO | WO-2011/110621 A1 | 9/2011 | |
| WO | WO-2011110621 A1 * | 9/2011 | ....... C07K 14/70503 |
| WO | WO-2011/091078 A9 | 1/2012 | |
| WO | WO-2012/022682 A1 | 2/2012 | |
| WO | WO-2013/006449 A2 | 1/2013 | |
| WO | WO-2014/039975 A2 | 3/2014 | |
| WO | WO-2014/130965 A1 | 8/2014 | |
| WO | WO-2014/153424 A1 | 9/2014 | |
| WO | WO-2015/070972 A1 | 5/2015 | |
| WO | WO-2015/164865 A1 | 10/2015 | |
| WO | WO-2017/100670 A1 | 6/2017 | |

OTHER PUBLICATIONS

Young et al (Cancer Discovery, 2014, 4:1-10).*
Gao et al (BioMed Research International, 2014, p. 1-9).*
Terp et al (J Immunology, 2013, 191:internet p. 1-9).*
Zhou et al (Cancer Biology & Therapy, 2007, 6:426-431).*
Tan et al (J Immunology, 2002, 169:1119-1125).*
Riechmann et al (Nature, 1988, 332:323-327).*
Hwang et al (Methods, 2005, 36:35-42).*
Williams et al ((2010). Humanising Antibodies by CDR Grafting. Chapter 21, pp. 319-339 in Kontermann, Roland & Dübel, Stefan. Antibody Engineering).*
First Office Action and Search Report issued by the China National Intellectual Property Administration in Chinese Patent Application No. 201680081339.6 dated Feb. 1, 2021 (Feb. 1, 2021). 12 pages. [Chinese language].
First Office Action and Search Report issued by the China National Intellectual Property Administration in Chinese Patent Application No. 201680081339.6 dated Feb. 1, 2021 (Feb. 1, 2021). 10 pages. [English language translation].
Examination Report issued in Indian Patent Application No. 201817025169, Date of Dispatch/Email: Nov. 27, 2020 (Nov. 27, 2020). 6 pages. [Includes English language translation].
First Office Action issued in Japanese Patent Application No. 2018-549405, dated Jan. 5, 2021. 2 pages. [English language translation].
First Office Action issued in Japanese Patent Application No. 2018-549405, dated Jan. 5, 2021. 3 pages. [Japanese language].
Office Action issued in Israeli Patent Application No. 259927, dated Jul. 7, 2021. 3 pages. [English language translation].
Office Action issued in Israeli Patent Application No. 259927, dated Jul. 7, 2021. 3 pages. [Hebrew language].
Second Office Action and Search Report issued in Chile Patent Application No. 2018-01512, dated Jun. 9, 2021. 12 pages. [Spanish language. References cited in English language].

(Continued)

*Primary Examiner* — Laura B Goddard
(74) *Attorney, Agent, or Firm* — MINTZ, LEVIN, COHN, FERRIS, GLOVSKY AND POPEO, P.C.

(57) ABSTRACT

Provided herein are, inter alia, humanized 1E9 antibodies capable of binding CD73. The humanized antibodies are useful for the treatment of cancer. Further provided are nucleic acids encoding humanized 1E9 antibodies and methods of inhibiting cell proliferation using the humanized antibodies provided herein.

15 Claims, 9 Drawing Sheets

Specification includes a Sequence Listing.

(56) References Cited

OTHER PUBLICATIONS

Almagro, J.C. et al. (Oct. 1, 2009) "Antibody Engineering: Humanization, Affinity Maturation, and Selection Techniques," *Therapeutic Monoclonal Antibodies: From Bench to Clinic* (Chapter 13), Wiley, Hoboken, US, pp. 311-334.

Extended European Search Report issued in European Patent Application No. EP 16 87 3984.5, dated Apr. 9, 2019 (Apr. 9, 2019). 7 pages.

Gao, Z-w, et al. (Jul. 14, 2014) "The Roles of CD73 in Cancer," *BioMed Research International*, 2014:9 pages.

Hausler, S. et al. (Jan. 30, 2014, e-published Jan. 15, 2014). "Anti-CD39 and anti-CD73 antibodies A1 and 7G2 improve targeted therapy in ovarian cancer by blocking adenosine-dependent immune evasion," *Am J Transl Res.*, 6(2):129-139.

International Search Report and Written Opinion issued in International Patent Application No. PCT/US16/65968, dated Feb. 28, 2017 (Feb. 28, 2017). 19 pages.

Massaia, M et al. (Sep. 15, 1990). "Human T Cell Activation. Synergy Between CD73 (Ecto-5'-Nucleotidasaen) Signals Delivered through CD3 and CD2 Molecules." *The Journal of Immunology.* 145(6): 1664-1674.

Safdari, Y. et al. (Oct. 1, 2013, e-published Aug. 2, 2013). "Antibody humanization methods—a review and update", *Biotechnology and Genetic Engineering Reviews* 29(2):175-186.

Tan, P. et al. (Jul. 15, 2002) ""Superhumanized" Antibodies: Reduction of Immunogenic Potential by Complementarity-Determining Region Grafting with Human Germline Sequences: Application to an Anti-CD28." *J Immunol.* 169:1119-1125.

Terp, M.G. et at. (2013, e-published Sep. 16, 2013). "Anti-Human CD73 Monoclonal Antibody Inhibits Metastasis Formation in Human Breast Cancer by Inducing Clustering and Internalization of CD73 Expressed on the Surface of Cancer Cells." *The Journal of Immunology.* 191:1-9.

Thomson, L.F. et al. (Jan. 1990). "Production and characterization of monoclonal antibodies to the glycosyl phosphatidylinositol-anchored lymphocyte differentiation antigen ecto-5'-nucleotidase(CD73)," *Tissue Antigens* 35(1):9-19.

Young, A. et al. (Aug. 1, 2014, e-published Jul. 17, 2014)."Targeting Cancer-Derived Adenosine: New Therapeutic Approaches," Cancer Discovery, vol. 4, No. 8, pp. 879-888 (1-10), XP055242089, US ISSN: 2159-8274, DOI: 10.1158/2159-8290.CD-14-0341.

\* cited by examiner

HUMANIZED ANTI-CD73 ANTIBODIES

CROSS REFERENCE TO RELATED APPLICATIONS

This application is a continuation of U.S. application Ser. No. 16/060,343, filed Jun. 7, 2018, now U.S. Pat. No. 10,822,426, issued Nov. 3, 2020, which is a national stage application filed under 35 U.S.C. § 371, of International Patent Application No. PCT/2016/065968, filed Dec. 9, 2016, which claims priority to U.S. Provisional Application No. 62/265,357, filed Dec. 9, 2015, U.S. Provisional Application No. 62/289,694, filed Feb. 1, 2016, and U.S. Provisional Application No. 62/346,327, filed Jun. 6, 2016, which are hereby incorporated by reference in their entirety and for all purposes.

REFERENCE TO A SEQUENCE LISTING, A TABLE OR A COMPUTER PROGRAM LISTING APPENDIX SUBMITTED AS AN ASCII TEXT FILE

The Sequence Listing written in file 048517-508C01US_SEQUENCE_LISTING_ST25.TXT, created on Dec. 8, 2020, 50,576 bytes, machine format IBM-PC, MS Windows operating system, is hereby incorporated by reference.

BACKGROUND OF THE INVENTION

The glycosyl-phosphatidylinositol-anchored CD73 antigen is considered the rate-limiting enzyme in the generation of extracellular adenosine (Stagg J, Smyth M J. Extracellular adenosine triphosphate and adenosine in cancer. Oncogene. 2010; 29:5346-58. doi: 10.1038/onc.2010.292). CD73 can be found constitutively expressed at high levels on various types of cancer cells. CD73-generated adenosine is assumed to suppress adaptive anti-tumor immune responses thereby promoting tumor growth and metastasis. There is a need in the art for antibody-based CD73 cancer therapy which inhibits the catalytic activity of CD73 and prevents the ability of circulating tumor cells to extravasate and colonize thereby inhibiting metastasis. The present invention addresses these and other needs in the art.

BRIEF SUMMARY OF THE INVENTION

In one aspect is provided a humanized 1E9 antibody including a humanized light chain variable region including a mouse CDR L1, mouse CDR L2, or mouse CDR L3 and a humanized heavy chain variable region including a mouse CDR H1, mouse CDR H2, or mouse CDR H3.

In one aspect, an antibody (e.g. a humanized 1E9 antibody) is provided. The antibody includes a light chain (e.g. humanized light chain) variable region and a heavy chain (e.g. humanized heavy chain) variable region. The light chain variable region includes:

(i) a CDR L1 (e.g. mouse CDR L1) as set forth in SEQ ID NO:1, a CDR L2 (e.g. a mouse CDR L2) as set forth in SEQ ID NO:2, a CDR L3 (e.g. a mouse CDR L3) as set forth in SEQ ID NO:3 and (ii) a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, a tyrosine at a position corresponding to Kabat position 85, or a phenylalanine at a position corresponding to Kabat position 87. The heavy chain variable region includes:

(i) a CDR H1 (e.g. a mouse CDR H1) as set forth in SEQ ID NO:4, a CDRH2 (e.g. a mouse CDR H2) as set forth in SEQ ID NO:5, a CDR H3 (e.g. a mouse CDR H3) as set forth in SEQ ID NO:6 and (ii) an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80, or a glutamic acid at a position corresponding to Kabat position 81.

In one aspect, a humanized 1E9 antibody is provided. The 1E9 antibody includes a humanized light chain variable region and a humanized heavy chain variable region. The humanized light chain variable region includes:
(i) a mouse CDR L1 as set forth in SEQ ID NO:1, a mouse CDR L2 as set forth in SEQ ID NO:2, a mouse CDR L3 as set forth in SEQ ID NO:3 and
(ii) a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, a tyrosine at a position corresponding to Kabat position 85, or a phenylalanine at a position corresponding to Kabat position 87. The humanized heavy chain variable region includes:
(i) a mouse CDR H1 as set forth in SEQ ID NO:4, a mouse CDR H2 as set forth in SEQ ID NO:5, and a mouse CDR H3 as set forth in SEQ ID NO:6 and
(ii) an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80, or a glutamic acid at a position corresponding to Kabat position 81.

In another aspect, provided is an antibody (e.g. a humanized 1E9 antibody) including a light chain (e.g. a humanized light chain) variable region and a heavy chain (e.g. a humanized heavy chain) variable region, wherein the heavy chain variable region comprises the sequence of SEQ ID NO:7.

In another aspect, provided is a humanized 1E9 antibody including a humanized light chain variable region and a humanized heavy chain variable region, wherein the humanized heavy chain variable region comprises the sequence of SEQ ID NO:7.

In one aspect, provided herein is an IgG1 (e.g. humanized IgG1) antibody including a light chain (e.g. a humanized light chain) variable region and a heavy chain (e.g. humanized heavy chain) variable region, wherein the light chain variable region includes a CDR L1 (e.g. mouse CDR L1) as set forth in SEQ ID NO:1, a CDR L2 (e.g. mouse CDR L2) as set forth in SEQ ID NO:2, a CDR L3 (e.g. mouse CDR L3) as set forth in SEQ ID NO:3 and wherein the heavy chain variable region includes a CDR H1 (e.g. mouse CDR H1) as set forth in SEQ ID NO:4, a CDR H2 (e.g. mouse CDR H2) as set forth in SEQ ID NO:5, a CDR H3 (e.g. mouse CDR H3) as set forth in SEQ ID NO:6.

In one aspect, provided herein is a humanized IgG1 antibody including a humanized light chain variable region and a humanized heavy chain variable region, wherein the humanized light chain variable region includes a mouse CDR L1 as set forth in SEQ ID NO:1, a mouse CDR L2 as set forth in SEQ ID NO:2, a mouse CDR L3 as set forth in SEQ ID NO:3 and wherein the humanized heavy chain variable region includes a mouse CDR H1 as set forth in SEQ ID NO:4, a mouse CDR H2 as set forth in SEQ ID NO:5, and a mouse CDR H3 as set forth in SEQ ID NO:6.

In one aspect, provided herein is an IgG4 (e.g. humanized IgG4) antibody including a light chain (e.g. a humanized light chain) variable region and a heavy chain (e.g. humanized heavy chain) variable region, wherein the light chain variable region includes a CDR L1 (e.g. mouse CDR L1) as set forth in SEQ ID NO:1, a CDR L2 (e.g. mouse CDR L2) as set forth in SEQ ID NO:2, a CDR L3 (e.g. mouse CDR L3) as set forth in SEQ ID NO:3 and wherein the heavy chain variable region includes a CDR H1 (e.g. mouse CDR H1) as set forth in SEQ ID NO:4, a CDR H2 (e.g. mouse CDR H2) as set forth in SEQ ID NO:5, a CDR H3 (e.g. mouse CDR H3) as set forth in SEQ ID NO:6.

In one aspect, provided herein is a humanized IgG4 antibody including a humanized light chain variable region and a humanized heavy chain variable region, wherein the humanized light chain variable region includes a mouse CDR L1 as set forth in SEQ ID NO:1, a mouse CDR L2 as set forth in SEQ ID NO:2, a mouse CDR L3 as set forth in SEQ ID NO:3 and wherein the humanized heavy chain variable region includes a mouse CDR H1 as set forth in SEQ ID NO:4, a mouse CDR H2 as set forth in SEQ ID NO:5, and a mouse CDR H3 as set forth in SEQ ID NO:6.

In one aspect, an isolated nucleic acid encoding a 1E9 antibody (e.g., a humanized 1E9 antibody) provided herein including embodiments is provided.

In one aspect, an isolated nucleic acid encoding a humanized 1E9 antibody provided herein including embodiments is provided.

In another aspect, an isolated nucleic acid encoding a IgG1 antibody (e.g., a humanized IgG1 antibody) provided herein including embodiments is provided.

In another aspect, an isolated nucleic acid encoding a humanized IgG1 antibody provided herein including embodiments is provided.

In another aspect, an isolated nucleic acid encoding a IgG4 antibody (e.g., a humanized IgG4 antibody) provided herein including embodiments is provided.

In another aspect, an isolated nucleic acid encoding a humanized IgG4 antibody provided herein including embodiments is provided.

In another aspect, a pharmaceutical composition including a therapeutically effective amount of a 1E9 antibody (e.g., a humanized 1E9 antibody) provided herein including embodiments thereof and a pharmaceutically acceptable excipient is provided.

In another aspect, a pharmaceutical composition including a therapeutically effective amount of a humanized 1E9 antibody provided herein including embodiments thereof and a pharmaceutically acceptable excipient is provided.

In another aspect, a pharmaceutical composition including a therapeutically effective amount of an IgG1 antibody (e.g., a humanized IgG1 antibody) provided herein including embodiments thereof and a pharmaceutically acceptable excipient is provided.

In another aspect, a pharmaceutical composition including a therapeutically effective amount of a humanized IgG1 antibody provided herein including embodiments thereof and a pharmaceutically acceptable excipient is provided.

In another aspect, a pharmaceutical composition including a therapeutically effective amount of an IgG4 antibody (e.g., a humanized IgG4 antibody) provided herein including embodiments thereof and a pharmaceutically acceptable excipient is provided.

In another aspect, a pharmaceutical composition including a therapeutically effective amount of a humanized IgG4 antibody provided herein including embodiments thereof and a pharmaceutically acceptable excipient is provided.

In one aspect, a method of treating cancer in a subject in need thereof is provided. The method includes administering to the subject a therapeutically effective amount of a 1E9 antibody (e.g., a humanized 1E9 antibody) provided herein including embodiments thereof, thereby treating cancer in the subject.

In one aspect, a method of treating cancer in a subject in need thereof is provided. The method includes administering to the subject a therapeutically effective amount of a humanized 1E9 antibody provided herein including embodiments thereof, thereby treating cancer in the subject.

In one aspect, a method of treating cancer in a subject in need thereof is provided. The method includes administering to the subject a therapeutically effective amount of an IgG1 antibody (e.g., a humanized IgG1 antibody) provided herein including embodiments thereof, thereby treating cancer in the subject.

In one aspect, a method of treating cancer in a subject in need thereof is provided. The method includes administering to the subject a therapeutically effective amount of a humanized IgG1 antibody provided herein including embodiments thereof, thereby treating cancer in the subject.

In one aspect, a method of treating cancer in a subject in need thereof is provided. The method includes administering to the subject a therapeutically effective amount of an IgG4 antibody (e.g., a humanized IgG4 antibody) provided herein including embodiments thereof, thereby treating cancer in the subject.

In one aspect, a method of treating cancer in a subject in need thereof is provided. The method includes administering to the subject a therapeutically effective amount of a humanized IgG4 antibody provided herein including embodiments thereof, thereby treating cancer in the subject.

In one aspect, a method of inhibiting proliferation of a cell is provided. The method includes (i) contacting a cell with an IgG1 antibody (e.g., a humanized IgG1 antibody) as provided herein including embodiments thereof, thereby forming a contacted cell. (ii) The IgG1 antibody (e.g., humanized IgG1 antibody) is allowed to bind a CD73 antigen on the contacted cell, thereby inhibiting proliferation of the cell.

In one aspect, a method of inhibiting proliferation of a cell is provided. The method includes (i) contacting a cell with a humanized IgG1 antibody as provided herein including embodiments thereof, thereby forming a contacted cell. (ii) The humanized IgG1 antibody is allowed to bind a CD73 antigen on the contacted cell, thereby inhibiting proliferation of the cell.

In one aspect, a method of inhibiting proliferation of a cell is provided. The method includes (i) contacting a cell with an IgG4 antibody (e.g., a humanized IgG4 antibody) as provided herein including embodiments thereof, thereby forming a contacted cell. (ii) The IgG4 antibody (e.g., humanized IgG4 antibody) is allowed to bind a CD73 antigen on the contacted cell, thereby inhibiting proliferation of the cell.

In one aspect, a method of inhibiting proliferation of a cell is provided. The method includes (i) contacting a cell with a humanized IgG4 antibody as provided herein including embodiments thereof, thereby forming a contacted cell. (ii) The humanized IgG4 antibody is allowed to bind a CD73 antigen on the contacted cell, thereby inhibiting proliferation of the cell.

In another aspect an anti-CD73 antibody is provided. The anti-CD73 binds the same epitope as a 1E9 antibody, wherein the 1E9 antibody includes a light chain variable region (e.g., a humanized light chain variable region) including a CDR L1 (e.g., a mouse CDR L1), CDR L2 (e.g., a mouse CDR L2), or CDR L3 (e.g., a mouse CDR L3) and a heavy chain variable region (e.g., a humanized heavy chain variable region) including a CDR H1 (e.g., a mouse CDR H1), CDR H2 (e.g., a mouse CDR H2), or CDR H3 (e.g., a mouse CDR H3).

In another aspect an anti-CD73 antibody is provided. The anti-CD73 binds the same epitope as a 1E9 antibody, wherein the 1E9 antibody includes a humanized light chain variable region including a mouse CDR L1, mouse CDR L2, or mouse CDR L3 and a humanized heavy chain variable region including a mouse CDR H1, mouse CDR H2, or mouse CDR H3.

In another aspect an anti-CD73 antibody is provided. The anti-CD73 binds the same epitope as a 1E9 antibody, wherein the 1E9 antibody includes a light chain variable region (e.g., a humanized light chain variable region) and a heavy chain variable region (e.g., a humanized heavy chain variable region). The light chain variable region includes:

(i) a CDR L1 (e.g., a mouse CDR L1) as set forth in SEQ ID NO:1, a CDR L2 (e.g., a mouse CDR L2) as set forth in SEQ ID NO:2, a CDR L3 (e.g., a mouse CDR L3) as set forth in SEQ ID NO:3 and (ii) a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, a tyrosine at a position corresponding to Kabat position 85, or a phenylalanine at a position corresponding to Kabat position 87. The humanized heavy chain variable region includes:

(i) a CDR H1 (e.g., a mouse CDR H1) as set forth in SEQ ID NO:4, a CDR H2 (e.g., a mouse CDR H2) as set forth in SEQ ID NO:5, a CDR H3 (e.g., a mouse CDR H3) as set forth in SEQ ID NO:6 and (ii) an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80, or a glutamic acid at a position corresponding to Kabat position 81.

In another aspect an anti-CD73 antibody is provided. The anti-CD73 binds the same epitope as a 1E9 antibody, wherein the 1E9 antibody includes a humanized light chain variable region and a humanized heavy chain variable region. The humanized light chain variable region includes:

(i) a mouse CDR L1 as set forth in SEQ ID NO:1, a mouse CDR L2 as set forth in SEQ ID NO:2, a mouse CDR L3 as set forth in SEQ ID NO:3 and (ii) a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, a tyrosine at a position corresponding to Kabat position 85, or a phenylalanine at a position corresponding to Kabat position 87. The humanized heavy chain variable region includes:

(i) a mouse CDR H1 as set forth in SEQ ID NO:4, a mouse CDR H2 as set forth in SEQ ID NO:5, and a mouse CDR H3 as set forth in SEQ ID NO:6 and (ii) an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80, or a glutamic acid at a position corresponding to Kabat position 81.

BRIEF DESCRIPTION OF THE DRAWINGS

FIG. 4A and FIG. 4B: FIG. 4A: Alignment of heavy chain variable domains. The variable domains of the top 10 hits were aligned to the parental clone BAP094-01 (chimeric 1E9 HC (SEQ ID NO:41)). Amino acid residues identical to the parental clone are represented by dots, only amino acid differences are shown. Four unique HC variable domains have been identified within the top 10 hits. The sequences are listed (top to bottom) based on identity of framework 3, framework 2 and framework 1. CDRs are boxed. The sequence listed for BAP094-hum01-HC corresponds to SEQ ID NO:42; the sequence listed for BAP094-hum02-HC corresponds to SEQ ID NO:43; the sequence listed for BAP094-hum06-HC corresponds to SEQ ID NO:47; the sequence listed for BAP094-hum07-HC corresponds to SEQ ID NO:48; the sequence listed for BAP094-hum08-HC corresponds to SEQ ID NO:49; the sequence listed for BAP094-hum03-HC corresponds to SEQ ID NO:44; the sequence listed for BAP094-hum09-HC corresponds to SEQ ID NO:50; the sequence listed for BAP094-hum04-HC corresponds to SEQ ID NO:45; the sequence listed for BAP094-hum05-HC corresponds to SEQ ID NO:46; the sequence listed for BAP094-hum10-HC corresponds to SEQ ID NO:51. FIG. 4B: Alignment of light chain variable domains. The variable domains of the top hits were aligned to the parental clone BAP094-01 (chimeric 1E9 LC (SEQ ID NO:30)). Amino acid residues identical to the parental clone are represented by dots, only amino acid differences are shown. 5 unique LC variable domains have been identified within the top 10 hits. The sequences are listed (top to bottom) based on identity of framework 3, framework 2, and framework 1. CDRs are boxed. The sequence listed for BAP094-hum02-LC corresponds to SEQ ID NO:32; the sequence listed for BAP094-hum03-LC corresponds to SEQ ID NO:33; the sequence listed for BAP094-hum04-LC corresponds to SEQ ID NO:34; the sequence listed for BAP094-hum01-LC corresponds to SEQ ID NO:31; the sequence listed for BAP094-hum07-LC corresponds to SEQ ID NO:37; the sequence listed for BAP094-hum08-LC corresponds to SEQ ID NO:38; the sequence listed for BAP094-hum09-LC corresponds to SEQ ID NO:39; the sequence listed for BAP094-hum10-LC corresponds to SEQ ID NO:40; the sequence listed for BAP094-hum05-LC corresponds to SEQ ID NO:35; the sequence listed for BAP094-hum06-LC corresponds to SEQ ID NO:36.

DETAILED DESCRIPTION OF THE INVENTION

Definitions

Figure 1:
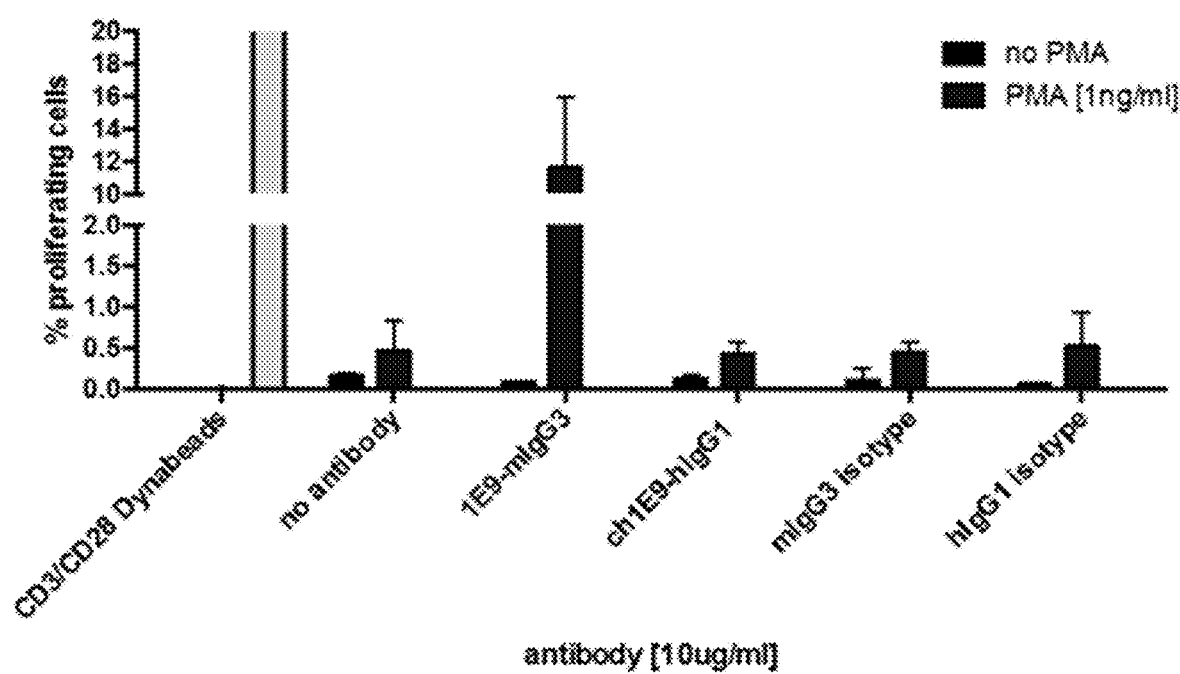
FIG. 1: Human T cells isolated by negative selection cultured with indicated treatments for 5 days. Cell proliferation is analyzed by dilution of Cell Trace Violet Tracker Dye.
Figure 2:
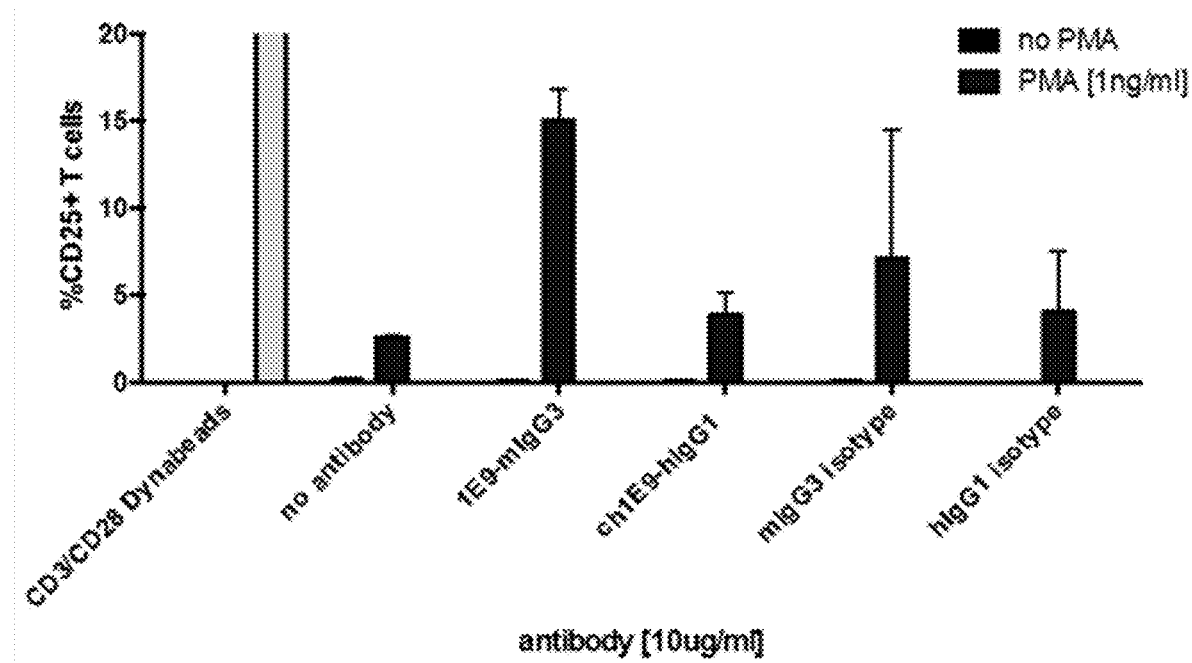
FIG. 2: Human T cells isolated by negative selection cultured with indicated treatments for 5 days. CD25 expression analyzed by flow cytometry.
Figure 3A:
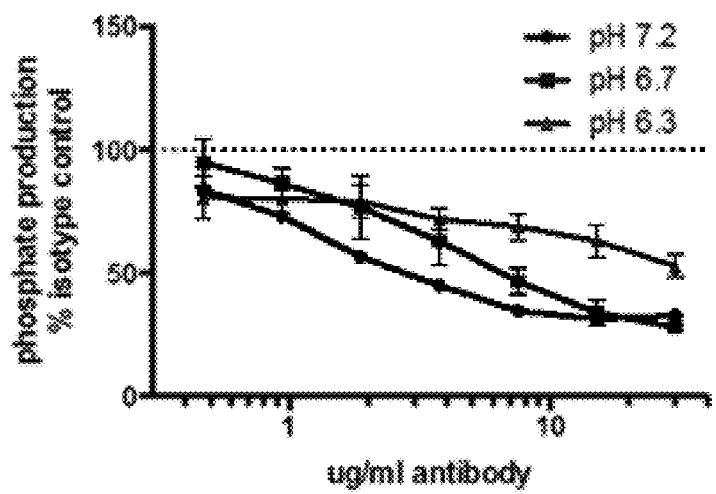
FIG. 3A-3E: MDA-MB-231 cells, a human breast cell line expressing CD73, were incubated with the indicated humanized antibodies (CPX-002 in FIG. 3A; CPX-005 in FIG. 3B; CPX-006 in FIG. 3C; CPX-004 in FIG. 3D; CPX-003 in FIG. 3E) over a range of concentrations for 1 hour at 37° C. Cells were washed in phosphate-free buffer and subsequently incubated with 250 µM AMP for 20 minutes at 37° C. Conditioned media was collected from each well and phosphate levels were determined using a malachite green based detection kit (Sensolyte MG phosphate kit, AnaSPEC). Absolute phosphate values were determined by interpolation to a standard curve. The assay was performed under 3 different pH conditions: 7.2, 6.7, or 6.3. Cells were equilibrated in buffer of the appropriate pH by washing prior to addition of antibody. The remainder of the assay was performed in buffer of the indicated pH.
Figure 3B:
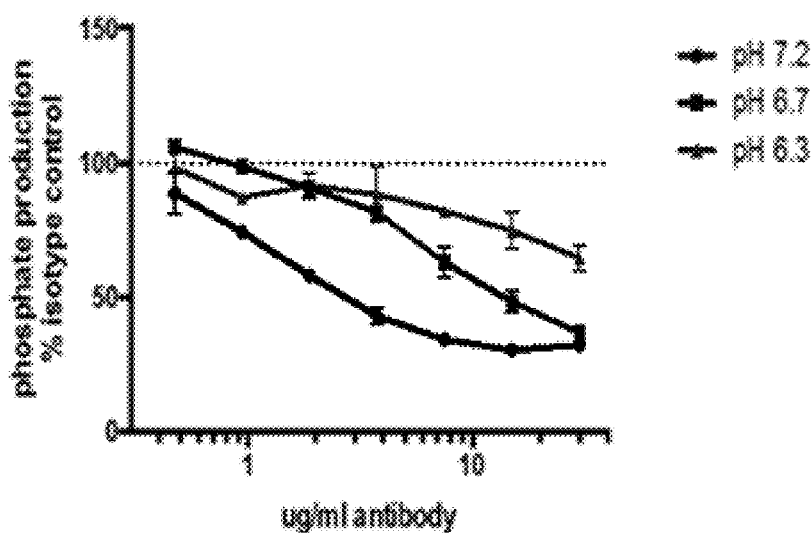
Figure 3C:
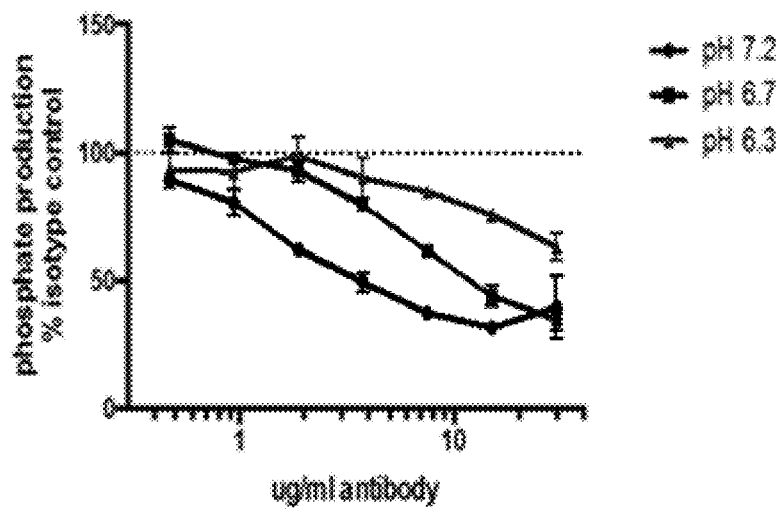
Figure 3D:
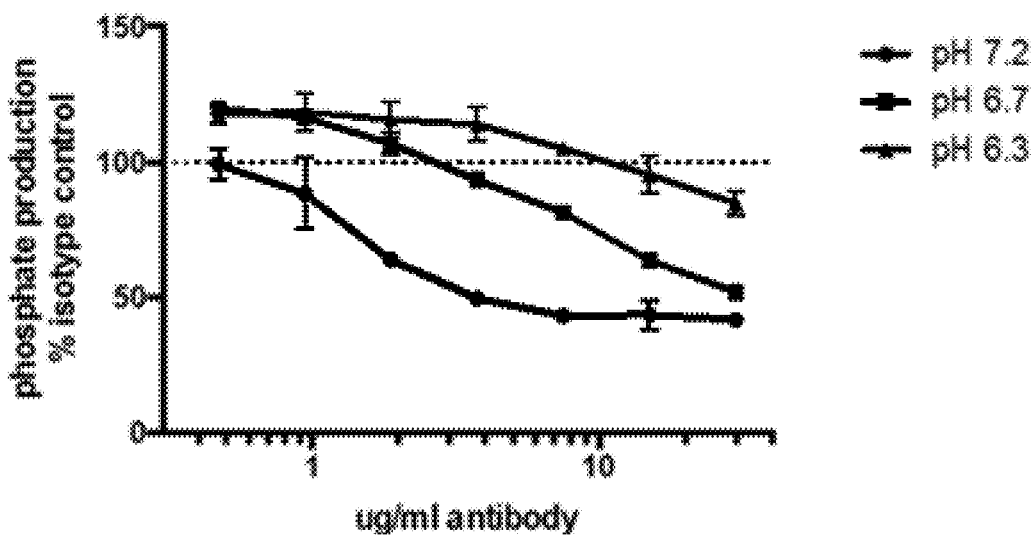
Figure 3E:
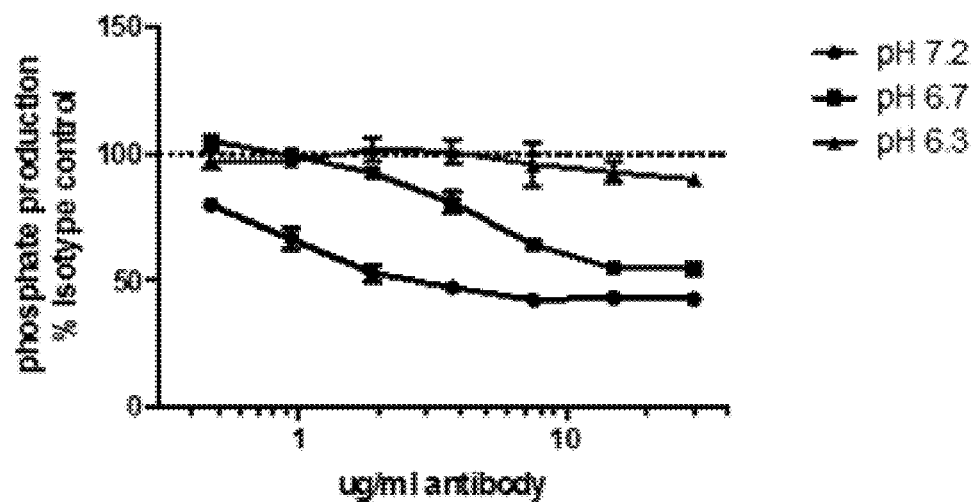

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

The terms "CDR L1", "CDR L2" and "CDR L3" as provided herein refer to the complementarity determining regions (CDR) 1, 2, and 3 of the variable light (L) chain of an antibody. Likewise, the terms "CDR H1", "CDR H2" and "CDR H3" as provided herein refer to the complementarity determining regions (CDR) 1, 2, and 3 of the variable heavy (H) chain of an antibody.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)).

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

A "ligand" refers to an agent, e.g., a polypeptide or other molecule, capable of binding to a receptor.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a biotin domain as described herein and a biotin-binding domain. In embodiments contacting includes, for example, allowing a humanized antibody as described herein to interact with CD73 antigen.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present invention includes polypeptides that are substantially identical to any of SEQ ID NOs:30-51.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

An amino acid residue in an antibody "corresponds" to a given residue when it occupies the same essential structural position within the antibody as the given residue. For example, a selected residue in a comparison antibody corresponds to position 48 (according to the Kabat numbering system as described herein) in an antibody provided herein when the selected residue occupies the same essential spatial or structural relationship to Kabat position 48 as assessed using applicable methods in the art. For example, a comparison antibody may be aligned for maximum sequence homology with the antibody provided herein and the position in the aligned comparison antibody that aligns with Kabat position 48 may be determined to correspond to it. Alternatively, instead of (or in addition to) a primary sequence alignment as described above, a three dimensional structural alignment can also be used, e.g., where the structure of the comparison antibody is aligned for maximum correspondence with an antibody provided herein and the overall structures compared. In this case, an amino acid that occupies the same essential position as Kabat position 48 in the structural model may be said to correspond.

The term "isolated," when applied to a protein, denotes that the protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified" denotes that a protein gives rise to essentially one band in an electrophoretic gel. Particularly, it means that the protein is at least 85% pure, more preferably at least 95% pure, and most preferably at least 99% pure.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Typically a specific or selective reaction will be at least twice background signal or noise and more typically more than 10 to 100 times background.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

As defined herein, the term "inhibition", "inhibit", "inhibiting" and the like in reference to a protein-inhibitor (e.g., humanized 1E9 antibody-CD73) interaction means negatively affecting (e.g., decreasing) the activity or function of the protein (e.g., decreasing the catalytic activity of CD73) relative to the activity or function of the protein in the absence of the inhibitor (e.g., humanized 1E9 antibody). In some embodiments inhibition refers to reduction of a disease or symptoms of disease. Thus, inhibition includes, at least in part, partially or totally blocking stimulation, decreasing, preventing, or delaying activation, or inactivating, desensitizing, or down-regulating signal transduction or enzymatic activity or the amount of a protein. Similarly an "inhibitor" is a compound or protein that inhibits CD73 activity, e.g., by binding, partially or totally blocking, decreasing, preventing, delaying, inactivating, desensitizing, or down-regulating enzymatic activity (e.g., CD73 catalytic activity).

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

The compositions provided herein, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The combined administrations contemplates co-administration, using separate formulations or a single pharmaceutical formulation, and consecutive administration in either order, wherein preferably there is a time period while both (or all) active agents simultaneously exert their biological activities.

Effective doses of the compositions provided herein vary depending upon many different factors, including means of administration, target site, physiological state of the patient, whether the patient is human or an animal, other medications administered, and whether treatment is prophylactic or therapeutic. However, a person of ordinary skill in the art would immediately recognize appropriate and/or equivalent doses looking at dosages of approved compositions for treating and preventing cancer for guidance.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

Humanized Antibodies

A humanized antibody is a genetically engineered antibody in which at least one CDR (or functional fragment thereof) from a mouse antibody ("donor antibody", which can also be rat, hamster or other non-human species) are grafted onto a human antibody ("acceptor antibody"). The human antibody is a non-natural (e.g. not naturally occurring or not naturally produced by a human) antibody that does not elicit an immune response in a human, does not elicit a significant immune response in a human, or elicits an immune response that is less than the immune response elicited in a mouse. In embodiments, more than one mouse CDR is grafted (e.g. all six mouse CDRs are grafted). The sequence of the acceptor antibody can be, for example, a mature human antibody sequence (or fragment thereof), a consensus sequence of a human antibody sequence (or fragment thereof), or a germline region sequence (or fragment thereof). Thus, a humanized antibody may be an antibody having one or more CDRs from a donor antibody and a variable region framework (FR). The FR may form part of a constant region and/or a variable region within a human antibody. In addition, in order to retain high binding affinity, amino acids in the human acceptor sequence may be replaced by the corresponding amino acids from the donor sequence, for example where: (1) the amino acid is in a CDR; (2) the amino acid is in the human framework region (e.g. the amino acid is immediately adjacent to one of the CDR's). See, U.S. Pat. Nos. 5,530,101 and 5,585,089, incorporated herein by reference, which provide detailed instructions for construction of humanized antibodies. Although humanized antibodies often incorporate all six CDRs (e.g. as defined by Kabat, but often also including hypervariable loop H1 as defined by Chothia) from a mouse antibody, they can also be made with fewer mouse CDRs and/or less than the complete mouse CDR sequence (e.g. a functional fragment of a CDR) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Typically a humanized antibody as provided herein may include (i) a light chain comprising at least one CDR (often three CDRs) from a mouse antibody (also referred to herein as a mouse CDR) and a human variable region framework; and (ii) a heavy chain comprising at least one CDR (often three CDRs) from the mouse antibody and a human variable region framework (FR). The light and heavy chain variable region frameworks (FRs) may each be a mature human antibody variable region framework sequence (or fragment thereof), a germline variable region framework sequence (combined with a J region sequence) (or fragment thereof), or a consensus sequence of a human antibody variable region framework sequence (or fragment thereof). In embodiments, the humanized antibody includes a light chain as described in (i), a heavy chain as described in (ii) together with a light chain human constant region and a heavy chain constant region.

A chimeric antibody is an antibody in which the variable region of a mouse (or other rodent) antibody is combined with the constant region of a human antibody; their construction by means of genetic engineering is well-known. Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies. Other types of genetically engineered antibodies that may have reduced immunogenicity relative to mouse antibodies include human antibodies made using phage display methods (Dower et al., WO91/17271; McCafferty et al., WO92/001047; Winter, WO92/20791; and Winter, FEBS Lett. 23:92, 1998, each of which is incorporated herein by reference) or using transgenic animals (Lonberg et al., WO93/12227; Kucherlapati WO91/10741, each of which is incorporated herein by reference).

Other approaches to design humanized antibodies may also be used to achieve the same result as the methods in U.S. Pat. Nos. 5,530,101 and 5,585,089 described above, for example, "superhumanization" (see Tan et al. J. Immunol. 169: 1119, 2002, and U.S. Pat. No. 6,881,557) or the method of Studnicak et al., Protein Eng. 7:805, 1994. Moreover, other approaches to produce genetically engineered, reduced-immunogenicity mAbs include "reshaping", "hyperchimerization" and veneering/resurfacing, as described, e.g., in Vaswami et al., Annals of Allergy, Asthma and Immunology 81:105, 1998; Roguska et al. Protein Eng. 9:895, 1996; and U.S. Pat. Nos. 6,072,035 and 5,639,641.

A "CD73 protein" or "CD73 antigen" as referred to herein includes any of the recombinant or naturally-occurring forms of the Cluster of Differentiation 73 (CD73) also known as 5'-nucleotidase (5'-NT) or ecto-5'-nucleotidase or variants or homologs thereof that maintain CD73 nucleotidase activity (e.g. within at least 50%, 80%, 90%, 95%, 96%, 97%, 98%, 99% or 100% activity compared to CD73). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD73 protein. In embodiments, the CD73 protein is substantially identical to the protein identified by the UniProt reference number 21589 or a variant or homolog having substantial identity thereto. In embodiments, the CD73 protein is substantially identical to the protein identified by the UniProt reference number Q61503 or a variant or homolog having substantial identity thereto.

Humanized 1E9 Antibodies

Provided herein are, inter alia, humanized 1E9 antibodies including a humanized light chain variable region and a humanized heavy chain variable region. The humanized 1E9 antibodies as provided herein are capable of binding a CD73 protein and include at least one CDR or a functional fragment thereof of the mouse monoclonal antibody 1E9 (Thomson L F et al. Tissue Antigens 2008, Volume 35, Issue 1: Production and characterization of monoclonal antibodies to the glycosyl phosphatidylinositol-anchored lymphocyte differentiation antigen ecto-5'-nucleotidase (CD73)). A functional fragment of a CDR is a portion of a complete CDR amino acid sequence that is capable of binding to an antigen (e.g., CD73). Thus, a functional fragment of a CDR typically includes the amino acid residues required for CDR binding to the antigen (e.g., CD73). A "mouse CDR" is a complete CDR amino acid sequence or a functional fragment thereof derived from a mouse antibody that is capable of binding CD73. Thus, a functional fragment of a mouse CDR typically includes the amino acid residues required for CDR binding to CD73. Where a humanized 1E9 antibody includes at least one mouse CDR, the at least one mouse CDR or a functional fragment thereof is derived from a donor antibody. In embodiments, the donor antibody is a mouse 1E9 antibody. A person of skill in the art will immediately recognize that a humanized 1E9 antibody including at least one mouse CDR is a humanized antibody with at least one mouse CDR derived from a donor 1E9 antibody and the additional CDRs are derived from the acceptor antibody (e.g. where the light chain includes a total of three CDRs and the heavy chain includes a total of three CDRs).

In embodiments, the humanized light chain variable region and the humanized heavy chain variable region include combined one mouse CDR or functional fragment of a mouse CDR. Thus, in some embodiments, the humanized light chain variable region and the humanized heavy chain variable region include combined six CDRs wherein at least one of the six CDRs is a mouse CDR. Where the humanized light chain variable region and the humanized heavy chain variable region include combined one mouse CDR, the humanized light chain variable region or the humanized heavy chain variable region include one mouse CDR. For example, a humanized antibody may include CDR L3 derived from the donor antibody (e.g. mouse, also referred to herein as a mouse CDR L3) and CDR L1, CDR L2, CDR H1, CDR H2, and CDR H3 derived from the acceptor antibody (i.e. human).

In embodiments, the humanized light chain variable region and the humanized heavy chain variable region include combined two mouse CDRs. Where the humanized light chain variable region and the humanized heavy chain variable region include combined two mouse CDRs, the humanized light chain variable region and the humanized heavy chain variable region each include one mouse CDR (i), the humanized light chain variable region includes two mouse CDRs (ii), or the humanized heavy chain variable region includes two mouse CDRs (iii). For example, a humanized antibody may include CDR L3 and CDR H3 derived from the donor antibody (also referred to herein as a mouse CDR L3 and a mouse CDR H3, respectively), and CDR L1, CDR L2, CDR H1, and CDR H2 derived from the acceptor antibody (i.e. human).

In embodiments, the humanized light chain variable region and the humanized heavy chain variable region include combined three mouse CDRs. Where the humanized light chain variable region and the humanized heavy chain variable region include combined three mouse CDRs, the humanized light chain variable region may include one mouse CDR and the humanized heavy chain variable region may include two mouse CDRs (i), the humanized light chain variable region includes two mouse CDRs and the humanized heavy chain variable region includes one mouse CDR (ii), the humanized light chain variable region includes three mouse CDRs (iii), or the humanized heavy chain variable region includes three mouse CDRs (iv). For example, a humanized antibody may include CDR L3, CDR H3 and CDR L2 derived from the donor antibody (e.g. mouse, also referred to herein as a CDR L3, mouse CDR H3, and mouse CDR L2 respectively) and CDR L1, CDR H1, and CDR H2 derived from the acceptor antibody (i.e. human).

In embodiments, the humanized light chain variable region and the humanized heavy chain variable region include combined four mouse CDRs. Where the humanized light chain variable region and the humanized heavy chain variable region include combined four mouse CDRs, the humanized light chain variable region includes one mouse CDR and the humanized heavy chain variable region includes three mouse CDRs (i), the humanized light chain variable region includes three mouse CDRs and the humanized heavy chain variable region includes one mouse CDR (ii), or the humanized light chain variable region includes two mouse CDRs and the humanized heavy chain variable region includes two mouse CDRs (iii). For example, a humanized antibody may include CDR L3, CDR H3, CDR L2 and CDR L1 derived from the donor antibody (e.g. mouse, also referred to herein as a mouse CDR L3, mouse CDR H3, mouse CDR L2 and mouse CDR L1 respectively) and CDR H1 and CDR H2 derived from the acceptor antibody (i.e. human).

In embodiments, the humanized light chain variable region and the humanized heavy chain variable region each include at least one mouse CDR. Where the humanized light chain variable region and the humanized heavy chain variable region each include at least one mouse CDR, the humanized light chain variable region includes at least one mouse CDR and the humanized heavy chain variable region includes at least one mouse CDR. Thus, in some embodiments, the humanized light chain variable region includes mouse CDR L1 and the humanized heavy chain includes mouse CDR H1. In embodiments, mouse CDR L1 includes the amino acid sequence of SEQ ID NO:1 and mouse CDR H1 includes the amino acid sequence of SEQ ID NO:4. In embodiments, mouse CDR L1 is the amino acid sequence of SEQ ID NO:1 and mouse CDR H1 is the amino acid sequence of SEQ ID NO:4. In embodiments, the humanized light chain variable region includes mouse CDR L2 and the humanized heavy chain variable region includes mouse CDR H2. In embodiments, mouse CDR L2 includes the amino acid sequence of SEQ ID NO:2 and mouse CDR H2 includes the amino acid sequence of SEQ ID NO:5. In embodiments, mouse CDR L2 is the amino acid sequence of SEQ ID NO:2 and mouse CDR H2 is the amino acid sequence of SEQ ID NO:5. In embodiments, the humanized light chain variable region includes mouse CDR L3 and the humanized heavy chain variable region includes mouse CDR H3. In embodiments, mouse CDR L3 includes the amino acid sequence of SEQ ID NO:3 and mouse CDR H3 includes the amino acid sequence of SEQ ID NO:6. In embodiments, CDR L3 is the amino acid sequence of SEQ ID NO:3 and mouse CDR H3 is the amino acid sequence of SEQ ID NO:6.

In embodiments, the presence of mouse CDR L3 and mouse CDR H3 may be sufficient for binding of a humanized antibody to CD73. Thus, in embodiments, the humanized antibody does not include mouse CDR L1, mouse CDR L2, CDR H1 or mouse CDR H2. Where the humanized antibody does not include mouse CDR L1, mouse CDR L2, mouse CDR H1 or mouse CDR H2, the humanized antibody includes CDR L1, CDR L2, CDR H1 or CDR H2 derived from the acceptor antibody (i.e. human). Thus, a humanized antibody that does not include mouse CDR L1, mouse CDR L2, mouse CDR H1 or mouse CDR H2, does not include CDR L1, CDR L2, CDR H1 or CDR H2 from a donor antibody (e.g. mouse, rat, rabbit), but includes CDR L1, CDR L2, CDR H1 or CDR H2 from the acceptor antibody (i.e. human). Thus, in embodiments the humanized light chain variable region does not include mouse CDR L1 or mouse CDR L2 and the humanized heavy chain variable region does not include mouse CDR H1 or mouse CDR H2. In embodiments, the humanized light chain variable region does not include mouse CDR L1 and mouse CDR L2 and the humanized heavy chain variable region does not include mouse CDR H1 and mouse CDR H2.

In embodiments, the humanized light chain variable region includes mouse CDR L2 and mouse CDR L3 and the humanized heavy chain variable region includes mouse CDR H2 and mouse CDR H3. In embodiments, the humanized light chain variable region includes mouse CDR L1, mouse CDR L2 and mouse CDR L3 and the humanized heavy chain variable region includes mouse CDR H1, mouse CDR H2 and mouse CDR H3. In embodiments, the humanized light chain variable region includes mouse CDR L1 as set forth in SEQ ID NO:1, mouse CDR L2 as set forth in SEQ ID NO:2 and mouse CDR L3 as set forth in SEQ ID NO:3, and the humanized heavy chain variable region includes mouse CDR H1 as set forth in SEQ ID NO:4, mouse CDR H2 as set forth in SEQ ID NO:5, and mouse CDR H3 as set forth in SEQ ID NO:6.

The position of CDRs and FRs may be defined by the Kabat numbering system (Kabat et al., Sequences of Proteins of Immunological Interest, Fifth Edition, U.S. Department of Health and Human Services, U.S. Government Printing Office (1991)). Likewise, the positions occupied by individual residues within the light or the heavy chain of an antibody may be defined by the Kabat numbering system. Therefore, the location of residues required for binding within a humanized light chain and a humanized heavy chain of a humanized antibody may be defined by the position of the residue according to the Kabat numbering system as is well known in the art. As described above, a humanized antibody may be an antibody having CDRs from a donor antibody (e.g. mouse) and variable region framework (FR) from a human antibody. The framework regions (FRs) are said to hold the CDRs in place in a humanized antibody. Proceeding from the amino-terminus, these regions are designated FR L1, FR L2, FR L3, and FR L4 for the light chain and FR H1, FR H2, FR H3, and FR H4, for the heavy chain, respectively. Surprisingly, the present invention provides for humanized antibodies that include one or more residues within the framework regions that are important for epitope binding of the humanized antibody. A framework region residue involved in (or important for) epitope binding (e.g. CD73 binding) is referred to herein as a binding framework region residue. The binding framework region residues may reside in the framework region of a humanized light chain variable region (i.e. FR L1, FR L2, FR L3, FR L4) or they may reside in the framework of a humanized heavy chain variable region (i.e. FR H1, FR H2, FR H3, FR H4). A binding framework residue residing in the FR L3 region of a humanized light chain is referred to herein as a FR L3 binding framework region residue. Thus, a binding framework region residue residing in the FR H3 region of a humanized heavy chain is referred to herein as a FR H3 binding framework region residue.

In embodiments, the humanized antibody includes at least one binding framework region residue. In embodiments, the humanized light chain variable region includes at least one binding framework region residue. In embodiments, the humanized light chain variable region includes one or more FR L1, FR L2, FR L3 or FR L4 binding framework region residues. In embodiments, the humanized light chain variable region includes one or more FR L1 binding framework region residues. In embodiments, the humanized light chain variable region includes one or more FR L2 binding framework region residues. In embodiments, the humanized light chain variable region includes one or more FR L3 binding framework region residues. In embodiments, the humanized light chain variable region includes one or more FR L4 binding framework region residues. In embodiments, the humanized heavy chain variable region includes one or more FR H1, FR H2, FR H3 or FR H4 binding framework region residues. In embodiments, the humanized heavy chain variable region includes one or more FR H1 binding framework region residues. In embodiments, the humanized heavy chain variable region includes one or more FR H2 binding framework region residues. In embodiments, the humanized heavy chain variable region includes one or more FR H3 binding framework region residues. In embodiments, the humanized heavy chain variable region includes one or more FR H4 binding framework region residues.

In embodiments, the humanized light chain variable region includes at least one binding framework region residue (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 37, 38, 39, 40, 41, 42 43, 44, 45, 46, 47, 48, 49, 50 or more residues) and the humanized heavy chain variable region includes at least one binding framework region residue (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 37, 38, 39, 40, 41, 42 43, 44, 45, 46, 47, 48, 49, 50 or more residues). The position of a binding framework region residue within a humanized antibody may be defined by the Kabat numbering system similar to the positions CDR residues.

In one aspect is provided a humanized 1E9 antibody including a humanized light chain variable region including a mouse CDR L1, mouse CDR L2, or mouse CDR L3 and a humanized heavy chain variable region including a mouse CDR H1, mouse CDR H2, or mouse CDR H3. The humanized light chain variable region may include a mouse CDR L1 as set forth in SEQ ID NO:1, a mouse CDR L2 as set forth in SEQ ID NO:2, or a mouse CDR L3 as set forth in SEQ ID NO:3. The humanized light chain variable region may include a mouse CDR L1 as set forth in SEQ ID NO:1, a mouse CDR L2 as set forth in SEQ ID NO:2, and a mouse CDR L3 as set forth in SEQ ID NO:3. The humanized heavy chain variable region may include a mouse CDR H1 as set forth in SEQ ID NO:4, a mouse CDR H2 as set forth in SEQ ID NO:5, or a mouse CDR H3 as set forth in SEQ ID NO:6. The humanized heavy chain variable region may include a mouse CDR H1 as set forth in SEQ ID NO:4, a mouse CDR H2 as set forth in SEQ ID NO:5, and a mouse CDR H3 as set forth in SEQ ID NO:6. In embodiments, the humanized light chain variable region includes a mouse CDR L1 as set forth in SEQ ID NO:1. In embodiments, the humanized light chain variable region includes a mouse CDR L2 as set forth in SEQ ID NO:2. In embodiments, the humanized light chain variable region includes a mouse CDR L3 as set forth in SEQ ID NO:3. In embodiments, the humanized heavy chain variable region includes a mouse CDR H1 as set forth in SEQ ID NO:4. In embodiments, the humanized heavy chain variable region includes a mouse CDR H2 as set forth in SEQ ID NO:5. In embodiments, the humanized light chain variable region includes a mouse CDR H3 as set forth in SEQ ID NO:6. In further embodiments, the humanized light chain variable region includes at least one binding framework region residue. In other further embodiments, the humanized heavy chain variable region includes at least one binding framework region residue.

In one aspect, a humanized 1E9 antibody is provided. The 1E9 antibody includes a humanized light chain variable region and a humanized heavy chain variable region. The humanized light chain variable region includes:
(i) a mouse CDR L1 as set forth in SEQ ID NO:1, a mouse CDR L2 as set forth in SEQ ID NO:2, a mouse CDR L3 as set forth in SEQ ID NO:3 and
(ii) a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, a tyrosine at a position corresponding to Kabat position 85, or a phenylalanine at a position corresponding to Kabat position 87. The humanized heavy chain variable region includes:

(i) a mouse CDR H1 as set forth in SEQ ID NO:4, a mouse CDR H2 as set forth in SEQ ID NO:5, and a mouse CDR H3 as set forth in SEQ ID NO:6 and (ii) an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80, or a glutamic acid at a position corresponding to Kabat position 81.

In embodiments, the humanized light chain variable region provided herein includes a binding framework region residue that is a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, a tyrosine at a position corresponding to Kabat position 85, or a phenylalanine at a position corresponding to Kabat position 87.

In embodiments, the humanized light chain variable region includes a binding framework region residue that is a valine at a position corresponding to Kabat position 2. In embodiments, the humanized light chain variable region includes a binding framework region residue that is a methionine at a position corresponding to Kabat position 4. In embodiments, the humanized light chain variable region includes a binding framework region residue that is an aspartic acid or a leucine at a position corresponding to Kabat position 9. In embodiments, the humanized light chain variable region includes a binding framework region residue that is a proline or a serine at a position corresponding to Kabat position 12. In embodiments, the humanized light chain variable region includes a binding framework region residue that is a lysine or a proline at a position corresponding to Kabat position 18. In embodiments, the humanized light chain variable region includes a binding framework region residue that is a alanine at a position corresponding to Kabat position 43. In embodiments, the humanized light chain variable region includes a binding framework region residue that is a proline or a serine at a position corresponding to Kabat position 60.

In embodiments, the humanized light chain variable region includes a binding framework region residue that is a threonine at a position corresponding to Kabat position 74. In embodiments, the humanized light chain variable region includes a binding framework region residue that is an asparagine or a serine at a position corresponding to Kabat position 76. In embodiments, the humanized light chain variable region includes a binding framework region residue that is an asparagine or a serine at a position corresponding to Kabat position 77. In embodiments, the humanized light chain variable region includes a binding framework region residue that is an isoleucine or a leucine at a position corresponding to Kabat position 78. In embodiments, the humanized light chain variable region includes a binding framework region residue that is a serine or an alanine at a position corresponding to Kabat position 80. In embodiments, the humanized light chain variable region includes a binding framework region residue that is a glutamine at a position corresponding to Kabat position 100. In embodiments, the humanized light chain variable region includes a binding framework region residue that is a valine at a position corresponding to Kabat position 104. In embodiments, the humanized light chain variable region includes a binding framework region residue that is a glutamic acid or an alanine at a position corresponding to Kabat position 1. In embodiments, the humanized light chain variable region includes a binding framework region residue that is a glutamine at a position corresponding to Kabat position 3.

In embodiments, the humanized light chain variable region includes a binding framework region residue that is a phenylalanine or a threonine at a position corresponding to Kabat position 10. In embodiments, the humanized light chain variable region includes a binding framework region residue that is a glutamine at a position corresponding to Kabat position 11. In embodiments, the humanized light chain variable region includes a binding framework region residue that is an alanine or a leucine at a position corresponding to Kabat position 13. In embodiments, the humanized light chain variable region includes a binding framework region residue that is a threonine at a position corresponding to Kabat position 14. In embodiments, the humanized light chain variable region includes a binding framework region residue that is a valine or a proline at a position corresponding to Kabat position 15. In embodiments, the humanized light chain variable region includes a binding framework region residue that is a lysine at a position corresponding to Kabat position 16. In embodiments, the humanized light chain variable region includes a binding framework region residue that is a glutamic acid or an aspartic acid at a position corresponding to Kabat position 17. In embodiments, the humanized light chain variable region includes a binding framework region residue that is a threonine at a position corresponding to Kabat position 22.

In embodiments, the humanized light chain variable region includes a binding framework region residue that is a lysine at a position corresponding to Kabat position 42. In embodiments, the humanized light chain variable region includes a binding framework region residue that is an arginine at a position corresponding to Kabat position 45. In embodiments, the humanized light chain variable region includes a binding framework region residue that is an isoleucine at a position corresponding to Kabat position 58. In embodiments, the humanized light chain variable region includes a binding framework region residue that is a tyrosine at a position corresponding to Kabat position 67. In embodiments, the humanized light chain variable region includes a binding framework region residue that is a phenylalanine at a position corresponding to Kabat position 73. In embodiments, the humanized light chain variable region includes a binding framework region residue that is an isoleucine at a position corresponding to Kabat position 78. In embodiments, the humanized light chain variable region includes a binding framework region residue that is a tyrosine at a position corresponding to Kabat position 85. In embodiments, the humanized light chain variable region includes a binding framework region residue that is a phenylalanine at a position corresponding to Kabat position 87.

The humanized heavy chain variable region provided herein may include a binding framework region residue that is an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80, or a glutamic acid at a position corresponding to Kabat position 81.

In embodiments, the humanized heavy chain variable region includes a binding framework region residue that is an isoleucine at a position corresponding to Kabat position 37. In embodiments, the humanized heavy chain variable region includes a binding framework region residue that is an alanine or a proline at a position corresponding to Kabat position 40. In embodiments, the humanized heavy chain variable region includes a binding framework region residue that is a lysine at a position corresponding to Kabat position 43. In embodiments, the humanized heavy chain variable region includes a binding framework region residue that is a serine at a position corresponding to Kabat position 70. In embodiments, the humanized heavy chain variable region includes a binding framework region residue that is an isoleucine or a threonine at a position corresponding to Kabat position 75. In embodiments, the humanized heavy chain variable region includes a binding framework region residue that is a tryptophan at a position corresponding to Kabat position 82. In embodiments, the humanized heavy chain variable region includes a binding framework region residue that is an arginine or a lysine at a position corresponding to Kabat position 83. In embodiments, the humanized heavy chain variable region includes a binding framework region residue that is a alanine at a position corresponding to Kabat position 84.

In embodiments, the humanized heavy chain variable region includes a binding framework region residue that is a serine at a position corresponding to Kabat position 85. In embodiments, the humanized heavy chain variable region includes a binding framework region residue that is a valine or a methionine at a position corresponding to Kabat position 89. In embodiments, the humanized heavy chain variable region includes a binding framework region residue that is a valine at a position corresponding to Kabat position 5. In embodiments, the humanized heavy chain variable region includes a binding framework region residue that is a serine at a position corresponding to Kabat position 7. In embodiments, the humanized heavy chain variable region includes a binding framework region residue that is a valine at a position corresponding to Kabat position 11. In embodiments, the humanized heavy chain variable region includes a binding framework region residue that is a glutamic acid or a lysine at a position corresponding to Kabat position 12. In embodiments, the humanized heavy chain variable region includes a binding framework region residue that is an isoleucine or a valine at a position corresponding to Kabat position 20. In embodiments, the humanized heavy chain variable region includes a binding framework region residue that is an arginine at a position corresponding to Kabat position 38. In embodiments, the humanized heavy chain variable region includes a binding framework region residue that is an arginine at a position corresponding to Kabat position 66. In embodiments, the humanized heavy chain variable region includes a binding framework region residue that is an valine at a position corresponding to Kabat position 67.

In embodiments, the humanized heavy chain variable region includes a binding framework region residue that is an isoleucine at a position corresponding to Kabat position 69. In embodiments, the humanized heavy chain variable region includes a binding framework region residue that is an alanine at a position corresponding to Kabat position 71. In embodiments, the humanized heavy chain variable region includes a binding framework region residue that is a lysine at a position corresponding to Kabat position 73. In embodiments, the humanized heavy chain variable region includes a binding framework region residue that is a threonine at a position corresponding to Kabat position 87. In embodiments, the humanized heavy chain variable region includes a binding framework region residue that is a glutamic acid at a position corresponding to Kabat position 1. In embodiments, the humanized heavy chain variable region includes a binding framework region residue that is a valine at a position corresponding to Kabat position 24. In embodiments, the humanized heavy chain variable region includes a binding framework region residue that is a arginine at a position corresponding to Kabat position 44. In embodiments, the humanized heavy chain variable region includes a binding framework region residue that is a methionine at a position corresponding to Kabat position 48. In embodiments, the humanized heavy chain variable region includes a binding framework region residue that is a leucine at a position corresponding to Kabat position 80. In embodiments, the humanized heavy chain variable region includes a binding framework region residue that is a glutamic acid at a position corresponding to Kabat position 81.

In embodiments, the humanized light chain variable region includes a valine at a position corresponding to Kabat position 2, a methionine at a position corresponding to Kabat position 4, a leucine at a position corresponding to Kabat position 9, a proline at a position corresponding to Kabat position 12, or a proline at a position corresponding to Kabat position 18;

and the humanized heavy chain variable region includes an isoleucine at a position corresponding to Kabat position 37, a proline at a position corresponding to Kabat position 40, a lysine at a position corresponding to Kabat position 43, a serine at a position corresponding to Kabat position 70, a isoleucine at a position corresponding to Kabat position 75, a tryptophan at a position corresponding to Kabat position 82, a lysine at a position corresponding to Kabat position 83, a alanine at a position corresponding to Kabat position 84, a serine at a position corresponding to Kabat position 85, or a methionine at a position corresponding to Kabat position 89.

In embodiments, the humanized light chain variable region includes a valine at a position corresponding to Kabat position 2, a methionine at a position corresponding to Kabat position 4, a leucine at a position corresponding to Kabat position 9, a proline at a position corresponding to Kabat position 12, and a proline at a position corresponding to Kabat position 18; and the humanized heavy chain variable region includes an isoleucine at a position corresponding to Kabat position 37, a proline at a position corresponding to Kabat position 40, a lysine at a position corresponding to Kabat position 43, a serine at a position corresponding to Kabat position 70, a isoleucine at a position corresponding to Kabat position 75, a tryptophan at a position corresponding to Kabat position 82, a lysine at a position corresponding to Kabat position 83, a alanine at a position corresponding to Kabat position 84, a serine at a position corresponding to Kabat position 85, or a methionine at a position corresponding to Kabat position 89.

In embodiments, the humanized light chain variable region includes a valine at a position corresponding to Kabat position 2, a methionine at a position corresponding to Kabat position 4, a leucine at a position corresponding to Kabat position 9, a proline at a position corresponding to Kabat position 12, or a proline at a position corresponding to Kabat position 18; and the humanized heavy chain variable region includes an isoleucine at a position corresponding to Kabat position 37, a proline at a position corresponding to Kabat position 40, a lysine at a position corresponding to Kabat position 43, a serine at a position corresponding to Kabat position 70, a isoleucine at a position corresponding to Kabat position 75, a tryptophan at a position corresponding to Kabat position 82, a lysine at a position corresponding to Kabat position 83, a alanine at a position corresponding to Kabat position 84, a serine at a position corresponding to Kabat position 85, and a methionine at a position corresponding to Kabat position 89.

In embodiments, the humanized light chain variable region includes a valine at a position corresponding to Kabat position 2, a methionine at a position corresponding to Kabat position 4, a leucine at a position corresponding to Kabat position 9, a proline at a position corresponding to Kabat position 12, and a proline at a position corresponding to Kabat position 18; and the humanized heavy chain variable region includes an isoleucine at a position corresponding to Kabat position 37, a proline at a position corresponding to Kabat position 40, a lysine at a position corresponding to Kabat position 43, a serine at a position corresponding to Kabat position 70, a isoleucine at a position corresponding to Kabat position 75, a tryptophan at a position corresponding to Kabat position 82, a lysine at a position corresponding to Kabat position 83, a alanine at a position corresponding to Kabat position 84, a serine at a position corresponding to Kabat position 85, and a methionine at a position corresponding to Kabat position 89.

In embodiments, the humanized light chain variable region includes a proline or a serine at a position corresponding to Kabat position 12, an alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100 or a valine at a position corresponding to Kabat position 104; and the humanized heavy chain variable region includes a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an alanine or a proline at a position corresponding to Kabat position 40, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, an isoleucine or a threonine at a position corresponding to Kabat position 75, an arginine or a lysine at a position corresponding to Kabat position 83 or a threonine at a position corresponding to Kabat position 87.

In embodiments, the humanized light chain variable region includes a proline or a serine at a position corresponding to Kabat position 12, an alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100 and a valine at a position corresponding to Kabat position 104; and the humanized heavy chain variable region includes a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an alanine or a proline at a position corresponding to Kabat position 40, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, an isoleucine or a threonine at a position corresponding to Kabat position 75, an arginine or a lysine at a position corresponding to Kabat position 83 or a threonine at a position corresponding to Kabat position 87.

In embodiments, the humanized light chain variable region includes a proline or a serine at a position corresponding to Kabat position 12, an alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100 or a valine at a position corresponding to Kabat position 104; and the humanized heavy chain variable region includes a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an alanine or a proline at a position corresponding to Kabat position 40, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, an isoleucine or a threonine at a position corresponding to Kabat position 75, an arginine or a lysine at a position corresponding to Kabat position 83 and a threonine at a position corresponding to Kabat position 87.

In embodiments, the humanized light chain variable region includes a proline or a serine at a position corresponding to Kabat position 12, an alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100 and a valine at a position corresponding to Kabat position 104; and the humanized heavy chain variable region includes a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an alanine or a proline at a position corresponding to Kabat position 40, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, an isoleucine or a threonine at a position corresponding to Kabat position 75, an arginine or a lysine at a position corresponding to Kabat position 83 and a threonine at a position corresponding to Kabat position 87.

In embodiments, humanized light chain variable region includes a glutamic acid or an alanine at a position corresponding to Kabat position 1, a valine at a position corresponding to Kabat position 2, a glutamine at a position corresponding to Kabat position 3, a methionine at a position corresponding to Kabat position 4, an aspartic acid or a leucine at a position corresponding to Kabat position 9, a phenylalanine or a threonine at a position corresponding to Kabat position 10, a glutamine at a position corresponding to Kabat position 11, a serine or a proline at a position corresponding to Kabat position 12, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a lysine or a proline at a position corresponding to Kabat position 18, a threonine at a position corresponding to Kabat position 22, a lysine at a position corresponding to Kabat position 42, an arginine at a position corresponding to Kabat position 45, an isoleucine at a position corresponding to Kabat position 58, a proline or a serine at a position corresponding to Kabat position 60, a tyrosine at a position corresponding to Kabat position 67, a phenylalanine at a position corresponding to Kabat position 73, an isoleucine at a position corresponding to Kabat position 78, a serine or an alanine at a position corresponding to Kabat position 80, a tyrosine at a position corresponding to Kabat position 85 or a phenylalanine at a position corresponding to Kabat position 87; and the humanized heavy chain variable region includes a glutamic acid at a position corresponding to Kabat position 1, a valine at a position corresponding to Kabat position 24, an isoleucine at a position corresponding to Kabat position 37, a lysine at a position corresponding to Kabat position 43, a arginine at a position corresponding to Kabat position 44, a methionine at a position corresponding to Kabat position 48, a serine at a position corresponding to Kabat position 70, a leucine at a position corresponding to Kabat position 80, a glutamic acid at a position corresponding to Kabat position 81, a tryptophan at a position corresponding to Kabat position 82, an alanine at a position corresponding to Kabat position 84, a serine at a position corresponding to Kabat position 85 or a valine or a methionine at a position corresponding to Kabat position 89.

In embodiments, humanized light chain variable region includes a glutamic acid or an alanine at a position corresponding to Kabat position 1, a valine at a position corresponding to Kabat position 2, a glutamine at a position corresponding to Kabat position 3, a methionine at a position corresponding to Kabat position 4, an aspartic acid or a leucine at a position corresponding to Kabat position 9, a phenylalanine or a threonine at a position corresponding to Kabat position 10, a glutamine at a position corresponding to Kabat position 11, a serine or a proline at a position corresponding to Kabat position 12, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a lysine or a proline at a position corresponding to Kabat position 18, a threonine at a position corresponding to Kabat position 22, a lysine at a position corresponding to Kabat position 42, an arginine at a position corresponding to Kabat position 45, an isoleucine at a position corresponding to Kabat position 58, a proline or a serine at a position corresponding to Kabat position 60, a tyrosine at a position corresponding to Kabat position 67, a phenylalanine at a position corresponding to Kabat position 73, an isoleucine at a position corresponding to Kabat position 78, a serine or an alanine at a position corresponding to Kabat position 80, a tyrosine at a position corresponding to Kabat position 85 and a phenylalanine at a position corresponding to Kabat position 87; and the humanized heavy chain variable region includes a glutamic acid at a position corresponding to Kabat position 1, a valine at a position corresponding to Kabat position 24, an isoleucine at a position corresponding to Kabat position 37, a lysine at a position corresponding to Kabat position 43, a arginine at a position corresponding to Kabat position 44, a methionine at a position corresponding to Kabat position 48, a serine at a position corresponding to Kabat position 70, a leucine at a position corresponding to Kabat position 80, a glutamic acid at a position corresponding to Kabat position 81, a tryptophan at a position corresponding to Kabat position 82, an alanine at a position corresponding to Kabat position 84, a serine at a position corresponding to Kabat position 85 or a valine or a methionine at a position corresponding to Kabat position 89.

In embodiments, humanized light chain variable region includes a glutamic acid or an alanine at a position corresponding to Kabat position 1, a valine at a position corresponding to Kabat position 2, a glutamine at a position corresponding to Kabat position 3, a methionine at a position corresponding to Kabat position 4, an aspartic acid or a leucine at a position corresponding to Kabat position 9, a phenylalanine or a threonine at a position corresponding to Kabat position 10, a glutamine at a position corresponding to Kabat position 11, a serine or a proline at a position corresponding to Kabat position 12, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a lysine or a proline at a position corresponding to Kabat position 18, a threonine at a position corresponding to Kabat position 22, a lysine at a position corresponding to Kabat position 42, an arginine at a position corresponding to Kabat position 45, an isoleucine at a position corresponding to Kabat position 58, a proline or a serine at a position corresponding to Kabat position 60, a tyrosine at a position corresponding to Kabat position 67, a phenylalanine at a position corresponding to Kabat position 73, an isoleucine at a position corresponding to Kabat position 78, a serine or an alanine at a position corresponding to Kabat position 80, a tyrosine at a position corresponding to Kabat position 85 or a phenylalanine at a position corresponding to Kabat position 87; and the humanized heavy chain variable region includes a glutamic acid at a position corresponding to Kabat position 1, a valine at a position corresponding to Kabat position 24, an isoleucine at a position corresponding to Kabat position 37, a lysine at a position corresponding to Kabat position 43, a arginine at a position corresponding to Kabat position 44, a methionine at a position corresponding to Kabat position 48, a serine at a position corresponding to Kabat position 70, a leucine at a position corresponding to Kabat position 80, a glutamic acid at a position corresponding to Kabat position 81, a tryptophan at a position corresponding to Kabat position 82, an alanine at a position corresponding to Kabat position 84, a serine at a position corresponding to Kabat position 85 and a valine or a methionine at a position corresponding to Kabat position 89.

In embodiments, humanized light chain variable region includes a glutamic acid or an alanine at a position corresponding to Kabat position 1, a valine at a position corresponding to Kabat position 2, a glutamine at a position corresponding to Kabat position 3, a methionine at a position corresponding to Kabat position 4, an aspartic acid or a leucine at a position corresponding to Kabat position 9, a phenylalanine or a threonine at a position corresponding to Kabat position 10, a glutamine at a position corresponding to Kabat position 11, a serine or a proline at a position corresponding to Kabat position 12, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a lysine or a proline at a position corresponding to Kabat position 18, a threonine at a position corresponding to Kabat position 22, a lysine at a position corresponding to Kabat position 42, an arginine at a position corresponding to Kabat position 45, an isoleucine at a position corresponding to Kabat position 58, a proline or a serine at a position corresponding to Kabat position 60, a tyrosine at a position corresponding to Kabat position 67, a phenylalanine at a position corresponding to Kabat position 73, an isoleucine at a position corresponding to Kabat position 78, a serine or an alanine at a position corresponding to Kabat position 80, a tyrosine at a position corresponding to Kabat position 85 and a phenylalanine at a position corresponding to Kabat position 87; and the humanized heavy chain variable region includes a glutamic acid at a position corresponding to Kabat position 1, a valine at a position corresponding to Kabat position 24, an isoleucine at a position corresponding to Kabat position 37, a lysine at a position corresponding to Kabat position 43, an arginine at a position corresponding to Kabat position 44, a methionine at a position corresponding to Kabat position 48, a serine at a position corresponding to Kabat position 70, a leucine at a position corresponding to Kabat position 80, a glutamic acid at a position corresponding to Kabat position 81, a tryptophan at a position corresponding to Kabat position 82, an alanine at a position corresponding to Kabat position 84, a serine at a position corresponding to Kabat position 85 and a valine or a methionine at a position corresponding to Kabat position 89.

In embodiments, the humanized heavy chain variable region includes a valine at a position corresponding to Kabat position 5, a serine at a position corresponding to Kabat position 7, a valine at a position corresponding to Kabat position 11, a glutamic acid at a position corresponding to Kabat position 12, a valine at a position corresponding to Kabat position 20, an arginine at a position corresponding to Kabat position 38, an alanine at a position corresponding to Kabat position 40, a methionine at a position corresponding to Kabat position 48, an arginine at a position corresponding to Kabat position 66, a valine at a position corresponding to Kabat position 67, an isoleucine at a position corresponding to Kabat position 69, an alanine at a position corresponding to Kabat position 71, a lysine at a position corresponding to Kabat position 73, a threonine at a position corresponding to Kabat position 75, a glutamic acid at a position corresponding to Kabat position 81, an arginine at a position corresponding to Kabat position 83, a threonine at a position corresponding to Kabat position 87, or a valine at a position corresponding to Kabat position 89.

In embodiments, the humanized heavy chain variable region includes a valine at a position corresponding to Kabat position 5, a serine at a position corresponding to Kabat position 7, a valine at a position corresponding to Kabat position 11, a glutamic acid at a position corresponding to Kabat position 12, a valine at a position corresponding to Kabat position 20, an arginine at a position corresponding to Kabat position 38, an alanine at a position corresponding to Kabat position 40, a methionine at a position corresponding to Kabat position 48, an arginine at a position corresponding to Kabat position 66, a valine at a position corresponding to Kabat position 67, an isoleucine at a position corresponding to Kabat position 69, an alanine at a position corresponding to Kabat position 71, a lysine at a position corresponding to Kabat position 73, a threonine at a position corresponding to Kabat position 75, a glutamic acid at a position corresponding to Kabat position 81, an arginine at a position corresponding to Kabat position 83, a threonine at a position corresponding to Kabat position 87, and a valine at a position corresponding to Kabat position 89.

In embodiments, the humanized heavy chain variable region includes the sequence of SEQ ID NO:7. In embodiments, the humanized heavy chain variable region is SEQ ID NO:7.

In embodiments, the humanized heavy chain variable region includes the sequence of SEQ ID NO:53. In embodiments, the humanized heavy chain variable region is SEQ ID NO:53. In embodiments, the humanized light chain variable region includes the sequence of SEQ ID NO:55. In embodiments, the humanized light chain variable region is SEQ ID NO:55. Thus, in another aspect, provided is a humanized 1E9 antibody including a humanized light chain variable region and a humanized heavy chain variable region, wherein the humanized heavy chain variable region includes the sequence of SEQ ID NO:53 and the humanized light chain variable region includes the sequence of SEQ ID NO:55.

Further provided herein are humanized 1E9 antibodies capable of binding CD73 and including a humanized light chain variable region and a humanized heavy chain variable region including the sequence of SEQ ID NO:7. Thus, in another aspect, provided is a humanized 1E9 antibody including a humanized light chain variable region and a humanized heavy chain variable region, wherein the humanized heavy chain variable region includes the sequence of SEQ ID NO:7.

The humanized 1E9 antibodies as provided herein may be Fab' fragments. Where the humanized 1E9 antibodies are Fab' fragments, the humanized 1E9 antibodies include a humanized heavy chain (e.g. including a constant and a variable region) and a humanized light chain (e.g. including a constant and a variable region). In embodiments, the humanized 1E9 antibody is a Fab' fragment. In embodiments, the humanized 1E9 antibody includes a human constant region. In embodiments, the humanized 1E9 antibody is an IgG. In embodiments, the humanized 1E9 antibody is an IgG1. In embodiments, the humanized 1E9 antibody is an IgG4. In embodiments, the humanized 1E9 antibody is an IgA. In other embodiments, the humanized antibody is an IgM.

In embodiments, the humanized 1E9 antibody is a single chain antibody. A single chain antibody includes a variable light chain and a variable heavy chain. A person of skill in the art will immediately recognize that a single chain antibody includes a single light chain and a single heavy chain, in contrast to an immunoglobulin antibody, which includes two identical pairs of polypeptide chains, each pair having one light chain and one heavy chain. Each light chain and heavy chain in turn consists of two regions: a variable ("V") region (i.e. variable light chain and variable heavy chain) involved in binding the target antigen, and a constant ("C") region that interacts with other components of the immune system. The variable light chain and the variable heavy chain in a single chain antibody may be linked through a linker peptide. Examples for linker peptides of single chain antibodies are described in Bird, R. E., Hardman, K. D., Jacobson, J. W., Johnson, S., Kaufman, B. M., Lee, S. M., Lee, T., Pope, S. H., Riordan, G. S. and Whitlow, M. (1988). Methods of making scFv antibodies have been described. See, Huse et al., *Science* 246:1275-1281 (1989); Ward et al., *Nature* 341:544-546 (1989); and Vaughan et al., *Nature Biotech.* 14:309-314 (1996). Briefly, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell.

The ability of an antibody to bind a specific epitope (e.g., CD73) can be described by the equilibrium dissociation constant ($K_D$). The equilibrium dissociation constant ($K_D$) as defined herein is the ratio of the dissociation rate (K-off) and the association rate (K-on) of a humanized 1E9 antibody to a CD73 protein. It is described by the following formula: $K_D$=K-off/K-on. In embodiments, the humanized antibody is capable of binding a CD73 antigen with an equilibrium dissociation constant ($K_D$) from about 0.5 to about 25 nM. In embodiments, the humanized antibody is capable of binding a CD73 antigen with an equilibrium dissociation constant ($K_D$) from about 1 to about 25 nM. In embodiments, the humanized antibody is capable of binding a CD73 antigen with an equilibrium dissociation constant ($K_D$) from about 1.5 to about 25 nM. In embodiments, the humanized antibody is capable of binding a CD73 antigen with an equilibrium dissociation constant ($K_D$) from about 2 to about 25 nM. In embodiments, the humanized antibody is capable of binding a CD73 antigen with an equilibrium dissociation constant ($K_D$) from about 2.5 to about 25 nM. In embodiments, the humanized antibody is capable of binding a CD73 antigen with an equilibrium dissociation constant ($K_D$) from about 3 to about 25 nM. In embodiments, the humanized antibody is capable of binding a CD73 antigen with an equilibrium dissociation constant ($K_D$) from about 3.5 to about 25 nM. In embodiments, the humanized antibody is capable of binding a CD73 antigen with an equilibrium dissociation constant ($K_D$) from about 4 to about 25 nM. In embodiments, the humanized antibody is capable of binding a CD73 antigen with an equilibrium dissociation constant ($K_D$) in this paragraph at a pH below 7.5. In embodiments, the humanized antibody is capable of binding a CD73 antigen with an equilibrium dissociation constant ($K_D$) in this paragraph at a pH of less than about 7.5. In embodiments, the humanized antibody is capable of binding a CD73 antigen with an equilibrium dissociation constant ($K_D$) in this paragraph at a pH of less than about 7.0. In embodiments, the humanized antibody is capable of binding a CD73 antigen with an equilibrium dissociation constant ($K_D$) in this paragraph at a pH of less than about 6.5. In embodiments, the humanized antibody is capable of binding a CD73 antigen with an equilibrium dissociation constant ($K_D$) in this paragraph at a pH of less than about 6.0. In embodiments, the humanized antibody is capable of binding a CD73 antigen with an equilibrium dissociation constant ($K_D$) in this paragraph at a pH of less than about 5.5. In embodiments, the humanized antibody is capable of binding a CD73 antigen with an equilibrium dissociation constant ($K_D$) in this paragraph at a pH of less than about 5. In embodiments, the humanized antibody is capable of binding a CD73 antigen with an equilibrium dissociation constant ($K_D$) in this paragraph at a pH of less than about 4.5. In embodiments, the humanized antibody is capable of binding a CD73 antigen with an equilibrium dissociation constant ($K_D$) in this paragraph at a pH from about 6.0 to about 7.0. In embodiments, the humanized antibody is capable of binding a CD73 antigen with an equilibrium dissociation constant ($K_D$) in this paragraph at a pH of about 6.0. In embodiments, the humanized antibody is capable of binding a CD73 antigen with an equilibrium dissociation constant ($K_D$) in this paragraph at a pH of about 6.1. In embodiments, the humanized antibody is capable of binding a CD73 antigen with an equilibrium dissociation constant ($K_D$) in this paragraph at a pH of about 6.2. In embodiments, the humanized antibody is capable of binding a CD73 antigen with an equilibrium dissociation constant ($K_D$) in this paragraph at a pH of about 6.3. In embodiments, the humanized antibody is capable of binding a CD73 antigen with an equilibrium dissociation constant ($K_D$) in this paragraph at a pH of about 6.4. In embodiments, the humanized antibody is capable of binding a CD73 antigen with an equilibrium dissociation constant ($K_D$) in this paragraph at a pH of about 6.5. In embodiments, the humanized antibody is capable of binding a CD73 antigen with an equilibrium dissociation constant ($K_D$) in this paragraph at a pH of about 6.6. In embodiments, the humanized antibody is capable of binding a CD73 antigen with an equilibrium dissociation constant ($K_D$) in this paragraph at a pH of about 6.7. In embodiments, the humanized antibody is capable of binding a CD73 antigen with an equilibrium dissociation constant ($K_D$) in this paragraph at a pH of about 6.8. In embodiments, the humanized antibody is capable of binding a CD73 antigen with an equilibrium dissociation constant ($K_D$) in this paragraph at a pH of about 6.9. In embodiments, the humanized antibody is capable of binding a CD73 antigen with an equilibrium dissociation constant ($K_D$) in this paragraph at a pH of about 7.0.

In embodiments, the humanized antibody is capable of binding a CD73 antigen with an equilibrium dissociation constant ($K_D$) from about 4.5 to about 25 nM. In embodiments, the humanized antibody is capable of binding a CD73 antigen with an equilibrium dissociation constant ($K_D$) from about 5 to about 25 nM. In embodiments, the humanized antibody is capable of binding a CD73 antigen with an equilibrium dissociation constant ($K_D$) from about 5.5 to about 25 nM. In embodiments, the humanized antibody is capable of binding a CD73 antigen with an equilibrium dissociation constant ($K_D$) from about 6 to about 25 nM. In embodiments, the humanized antibody is capable of binding a CD73 antigen with an equilibrium dissociation constant ($K_D$) from about 6.5 to about 25 nM. In embodiments, the humanized antibody is capable of binding a CD73 antigen with an equilibrium dissociation constant ($K_D$) from about 7 to about 25 nM. In embodiments, the humanized antibody is capable of binding a CD73 antigen with an equilibrium dissociation constant ($K_D$) from about 7.5 to about 25 nM. In embodiments, the humanized antibody is capable of binding a CD73 antigen with an equilibrium dissociation constant ($K_D$) from about 8 to about 25 nM. In embodiments, the humanized antibody is capable of binding a CD73 antigen with an equilibrium dissociation constant ($K_D$) in this paragraph at a pH below 7.5. In embodiments, the humanized antibody is capable of binding a CD73 antigen with an equilibrium dissociation constant ($K_D$) in this paragraph at a pH of less than about 7.5. In embodiments, the humanized antibody is capable of binding a CD73 antigen with an equilibrium dissociation constant ($K_D$) in this paragraph at a pH of less than about 7.0. In embodiments, the humanized antibody is capable of binding a CD73 antigen with an equilibrium dissociation constant ($K_D$) in this paragraph at a pH of less than about 6.5. In embodiments, the humanized antibody is capable of binding a CD73 antigen with an equilibrium dissociation constant ($K_D$) in this paragraph at a pH of less than about 6.0. In embodiments, the humanized antibody is capable of binding a CD73 antigen with an equilibrium dissociation constant ($K_D$) in this paragraph at a pH of less than about 5.5. In embodiments, the humanized antibody is capable of binding a CD73 antigen with an equilibrium dissociation constant ($K_D$) in this paragraph at a pH of less than about 5. In embodiments, the humanized antibody is capable of binding a CD73 antigen with an equilibrium dissociation constant ($K_D$) in this paragraph at a pH of less than about 4.5. In embodiments, the humanized antibody is capable of binding a CD73 antigen with an equilibrium dissociation constant ($K_D$) in this paragraph at a pH from about 6.0 to about 7.0. In embodiments, the humanized antibody is capable of binding a CD73 antigen with an equilibrium dissociation constant ($K_D$) in this paragraph at a pH of about 6.0. In embodiments, the humanized antibody is capable of binding a CD73 antigen with an equilibrium dissociation constant ($K_D$) in this paragraph at a pH of about 6.1. In embodiments, the humanized antibody is capable of binding a CD73 antigen with an equilibrium dissociation constant ($K_D$) in this paragraph at a pH of about 6.2. In embodiments, the humanized antibody is capable of binding a CD73 antigen with an equilibrium dissociation constant ($K_D$) in this paragraph at a pH of about 6.3. In embodiments, the humanized antibody is capable of binding a CD73 antigen with an equilibrium dissociation constant ($K_D$) in this paragraph at a pH of about 6.4. In embodiments, the humanized antibody is capable of binding a CD73 antigen with an equilibrium dissociation constant ($K_D$) in this paragraph at a pH of about 6.5. In embodiments, the humanized antibody is capable of binding a CD73 antigen with an equilibrium dissociation constant ($K_D$) in this paragraph at a pH of about 6.6. In embodiments, the humanized antibody is capable of binding a CD73 antigen with an equilibrium dissociation constant ($K_D$) in this paragraph at a pH of about 6.7. In embodiments, the humanized antibody is capable of binding a CD73 antigen with an equilibrium dissociation constant ($K_D$) in this paragraph at a pH of about 6.8. In embodiments, the humanized antibody is capable of binding a CD73 antigen with an equilibrium dissociation constant ($K_D$) in this paragraph at a pH of about 6.9. In embodiments, the humanized antibody is capable of binding a CD73 antigen with an equilibrium dissociation constant ($K_D$) in this paragraph at a pH of about 7.0.

In embodiments, the humanized antibody is capable of binding a CD73 antigen with an equilibrium dissociation constant ($K_D$) from about 8.5 to about 25 nM. In embodiments, the humanized antibody is capable of binding a CD73 antigen with an equilibrium dissociation constant ($K_D$) from about 9 to about 25 nM. In embodiments, the humanized antibody is capable of binding a CD73 antigen with an equilibrium dissociation constant ($K_D$) from about 9.5 to about 25 nM. In embodiments, the humanized antibody is capable of binding a CD73 antigen with an equilibrium dissociation constant ($K_D$) from about 10 to about 25 nM. In embodiments, the humanized antibody is capable of binding a CD73 antigen with an equilibrium dissociation constant ($K_D$) from about 11 to about 25 nM. In embodiments, the humanized antibody is capable of binding a CD73 antigen with an equilibrium dissociation constant ($K_D$) from about 12 to about 25 nM. In embodiments, the humanized antibody is capable of binding a CD73 antigen with an equilibrium dissociation constant ($K_D$) from about 13 to about 25 nM. In embodiments, the humanized antibody is capable of binding a CD73 antigen with an equilibrium dissociation constant ($K_D$) from about 14 to about 25 nM. In embodiments, the humanized antibody is capable of binding a CD73 antigen with an equilibrium dissociation constant ($K_D$) from about 15 to about 25 nM. In embodiments, the humanized antibody is capable of binding a CD73 antigen with an equilibrium dissociation constant ($K_D$) from about 16 to about 25 nM. In embodiments, the humanized antibody is capable of binding a CD73 antigen with an equilibrium dissociation constant ($K_D$) in this paragraph at a pH below 7.5. In embodiments, the humanized antibody is capable of binding a CD73 antigen with an equilibrium dissociation constant ($K_D$) in this paragraph at a pH of less than about 7.5. In embodiments, the humanized antibody is capable of binding a CD73 antigen with an equilibrium dissociation constant ($K_D$) in this paragraph at a pH of less than about 7.0. In embodiments, the humanized antibody is capable of binding a CD73 antigen with an equilibrium dissociation constant ($K_D$) in this paragraph at a pH of less than about 6.5. In embodiments, the humanized antibody is capable of binding a CD73 antigen with an equilibrium dissociation constant ($K_D$) in this paragraph at a pH of less than about 6.0. In embodiments, the humanized antibody is capable of binding a CD73 antigen with an equilibrium dissociation constant ($K_D$) in this paragraph at a pH of less than about 5.5. In embodiments, the humanized antibody is capable of binding a CD73 antigen with an equilibrium dissociation constant ($K_D$) in this paragraph at a pH of less than about 5. In embodiments, the humanized antibody is capable of binding a CD73 antigen with an equilibrium dissociation constant ($K_D$) in this paragraph at a pH of less than about 4.5. In embodiments, the humanized antibody is capable of binding a CD73 antigen with an equilibrium dissociation constant ($K_D$) in this paragraph at a pH from about 6.0 to about 7.0. In embodiments, the humanized antibody is capable of binding a CD73 antigen with an equilibrium dissociation constant ($K_D$) in this paragraph at a pH of about 6.0. In embodiments, the humanized antibody is capable of binding a CD73 antigen with an equilibrium dissociation constant ($K_D$) in this paragraph at a pH of about 6.1. In embodiments, the humanized antibody is capable of binding a CD73 antigen with an equilibrium dissociation constant ($K_D$) in this paragraph at a pH of about 6.2. In embodiments, the humanized antibody is capable of binding a CD73 antigen with an equilibrium dissociation constant ($K_D$) in this paragraph at a pH of about 6.3. In embodiments, the humanized antibody is capable of binding a CD73 antigen with an equilibrium dissociation constant ($K_D$) in this paragraph at a pH of about 6.4. In embodiments, the humanized antibody is capable of binding a CD73 antigen with an equilibrium dissociation constant ($K_D$) in this paragraph at a pH of about 6.5. In embodiments, the humanized antibody is capable of binding a CD73 antigen with an equilibrium dissociation constant ($K_D$) in this paragraph at a pH of about 6.6. In embodiments, the humanized antibody is capable of binding a CD73 antigen with an equilibrium dissociation constant ($K_D$) in this paragraph at a pH of about 6.7. In embodiments, the humanized antibody is capable of binding a CD73 antigen with an equilibrium dissociation constant ($K_D$) in this paragraph at a pH of about 6.8. In embodiments, the humanized antibody is capable of binding a CD73 antigen with an equilibrium dissociation constant ($K_D$) in this paragraph at a pH of about 6.9. In embodiments, the humanized antibody is capable of binding a CD73 antigen with an equilibrium dissociation constant ($K_D$) in this paragraph at a pH of about 7.0.

In embodiments, the humanized antibody is capable of binding a CD73 antigen with an equilibrium dissociation constant ($K_D$) from about 17 to about 25 nM. In embodiments, the humanized antibody is capable of binding a CD73 antigen with an equilibrium dissociation constant ($K_D$) from about 18 to about 25 nM. In embodiments, the humanized antibody is capable of binding a CD73 antigen with an equilibrium dissociation constant ($K_D$) from about 19 to about 25 nM. In embodiments, the humanized antibody is capable of binding a CD73 antigen with an equilibrium dissociation constant ($K_D$) from about 20 to about 25 nM. In embodiments, the humanized antibody is capable of binding a CD73 antigen with an equilibrium dissociation constant ($K_D$) from about 21 to about 25 nM. In embodiments, the humanized antibody is capable of binding a CD73 antigen with an equilibrium dissociation constant ($K_D$) from about 22 to about 25 nM. In embodiments, the humanized antibody is capable of binding a CD73 antigen with an equilibrium dissociation constant ($K_D$) from about 23 to about 25 nM. In embodiments, the humanized antibody is capable of binding a CD73 antigen with an equilibrium dissociation constant ($K_D$) from about 24 to about 25 nM. In embodiments, the humanized antibody is capable of binding a CD73 antigen with an equilibrium dissociation constant ($K_D$) of about 0.5, 1 2, 3, 4, 5, 6, 7, 8, 9, 10, 11, 12, 13, 14, 15, 16, 17, 18, 19, 20, 21, 22, 23, 24, or 25 nM. In embodiments, the humanized antibody is capable of binding a CD73 antigen with an equilibrium dissociation constant ($K_D$) in this paragraph at a pH below 7.5. In embodiments, the humanized antibody is capable of binding a CD73 antigen with an equilibrium dissociation constant ($K_D$) in this paragraph at a pH of less than about 7.5. In embodiments, the humanized antibody is capable of binding a CD73 antigen with an equilibrium dissociation constant ($K_D$) in this paragraph at a pH of less than about 7.0. In embodiments, the humanized antibody is capable of binding a CD73 antigen with an equilibrium dissociation constant ($K_D$) in this paragraph at a pH of less than about 6.5. In embodiments, the humanized antibody is capable of binding a CD73 antigen with an equilibrium dissociation constant ($K_D$) in this paragraph at a pH of less than about 6.0. In embodiments, the humanized antibody is capable of binding a CD73 antigen with an equilibrium dissociation constant ($K_D$) in this paragraph at a pH of less than about 5.5. In embodiments, the humanized antibody is capable of binding a CD73 antigen with an equilibrium dissociation constant ($K_D$) in this paragraph at a pH of less than about 5. In embodiments, the humanized antibody is capable of binding a CD73 antigen with an equilibrium dissociation constant ($K_D$) in this paragraph at a pH of less than about 4.5. In embodiments, the humanized antibody is capable of binding a CD73 antigen with an equilibrium dissociation constant ($K_D$) in this paragraph at a pH from about 6.0 to about 7.0. In embodiments, the humanized antibody is capable of binding a CD73 antigen with an equilibrium dissociation constant ($K_D$) in this paragraph at a pH of about 6.0. In embodiments, the humanized antibody is capable of binding a CD73 antigen with an equilibrium dissociation constant ($K_D$) in this paragraph at a pH of about 6.1. In embodiments, the humanized antibody is capable of binding a CD73 antigen with an equilibrium dissociation constant ($K_D$) in this paragraph at a pH of about 6.2. In embodiments, the humanized antibody is capable of binding a CD73 antigen with an equilibrium dissociation constant ($K_D$) in this paragraph at a pH of about 6.3. In embodiments, the humanized antibody is capable of binding a CD73 antigen with an equilibrium dissociation constant ($K_D$) in this paragraph at a pH of about 6.4. In embodiments, the humanized antibody is capable of binding a CD73 antigen with an equilibrium dissociation constant ($K_D$) in this paragraph at a pH of about 6.5. In embodiments, the humanized antibody is capable of binding a CD73 antigen with an equilibrium dissociation constant ($K_D$) in this paragraph at a pH of about 6.6. In embodiments, the humanized antibody is capable of binding a CD73 antigen with an equilibrium dissociation constant ($K_D$) in this paragraph at a pH of about 6.7. In embodiments, the humanized antibody is capable of binding a CD73 antigen with an equilibrium dissociation constant ($K_D$) in this paragraph at a pH of about 6.8. In embodiments, the humanized antibody is capable of binding a CD73 antigen with an equilibrium dissociation constant ($K_D$) in this paragraph at a pH of about 6.9. In embodiments, the humanized antibody is capable of binding a CD73 antigen with an equilibrium dissociation constant ($K_D$) in this paragraph at a pH of about 7.0.

In embodiments, the humanized antibody is capable of binding a CD73 antigen with an equilibrium dissociation constant ($K_D$) of about 7.1 nM. In embodiments, the humanized antibody is capable of binding a CD73 antigen with an equilibrium dissociation constant ($K_D$) of about 6.9 nM. In embodiments, the humanized antibody is capable of binding a CD73 antigen with an equilibrium dissociation constant ($K_D$) of about 9.4 nM. In embodiments, the humanized antibody is capable of binding a CD73 antigen with an equilibrium dissociation constant ($K_D$) of about 19.5 nM. In embodiments, the humanized antibody is capable of binding a CD73 antigen with an equilibrium dissociation constant ($K_D$) of about 17.8 nM. In embodiments, the humanized antibody is capable of binding a CD73 antigen with an equilibrium dissociation constant ($K_D$) of about 15.9 nM. In embodiments, the humanized antibody is capable of binding a CD73 antigen with an equilibrium dissociation constant ($K_D$) in this paragraph at a pH below 7.5. In embodiments, the humanized antibody is capable of binding a CD73 antigen with an equilibrium dissociation constant ($K_D$) in this paragraph at a pH of less than about 7.5. In embodiments, the humanized antibody is capable of binding a CD73 antigen with an equilibrium dissociation constant ($K_D$) in this paragraph at a pH of less than about 7.0. In embodiments, the humanized antibody is capable of binding a CD73 antigen with an equilibrium dissociation constant ($K_D$) in this paragraph at a pH of less than about 6.5. In embodiments, the humanized antibody is capable of binding a CD73 antigen with an equilibrium dissociation constant ($K_D$) in this paragraph at a pH of less than about 6.0. In embodiments, the humanized antibody is capable of binding a CD73 antigen with an equilibrium dissociation constant ($K_D$) in this paragraph at a pH of less than about 5.5. In embodiments, the humanized antibody is capable of binding a CD73 antigen with an equilibrium dissociation constant ($K_D$) in this paragraph at a pH of less than about 5. In embodiments, the humanized antibody is capable of binding a CD73 antigen with an equilibrium dissociation constant ($K_D$) in this paragraph at a pH of less than about 4.5. In embodiments, the humanized antibody is capable of binding a CD73 antigen with an equilibrium dissociation constant ($K_D$) in this paragraph at a pH from about 6.0 to about 7.0. In embodiments, the humanized antibody is capable of binding a CD73 antigen with an equilibrium dissociation constant ($K_D$) in this paragraph at a pH of about 6.0. In embodiments, the humanized antibody is capable of binding a CD73 antigen with an equilibrium dissociation constant ($K_D$) in this paragraph at a pH of about 6.1. In embodiments, the humanized antibody is capable of binding a CD73 antigen with an equilibrium dissociation constant ($K_D$) in this paragraph at a pH of about 6.2. In embodiments, the humanized antibody is capable of binding a CD73 antigen with an equilibrium dissociation constant ($K_D$) in this paragraph at a pH of about 6.3. In embodiments, the humanized antibody is capable of binding a CD73 antigen with an equilibrium dissociation constant ($K_D$) in this paragraph at a pH of about 6.4. In embodiments, the humanized antibody is capable of binding a CD73 antigen with an equilibrium dissociation constant ($K_D$) in this paragraph at a pH of about 6.5. In embodiments, the humanized antibody is capable of binding a CD73 antigen with an equilibrium dissociation constant (K$_D$) in this paragraph at a pH of about 6.6. In embodiments, the humanized antibody is capable of binding a CD73 antigen with an equilibrium dissociation constant (K$_D$) in this paragraph at a pH of about 6.7. In embodiments, the humanized antibody is capable of binding a CD73 antigen with an equilibrium dissociation constant (K$_D$) in this paragraph at a pH of about 6.8. In embodiments, the humanized antibody is capable of binding a CD73 antigen with an equilibrium dissociation constant (K$_D$) in this paragraph at a pH of about 6.9. In embodiments, the humanized antibody is capable of binding a CD73 antigen with an equilibrium dissociation constant (K$_D$) in this paragraph at a pH of about 7.0.

In one aspect, an antibody capable of binding CD73 at a pH of less than about 7.5 is provided. In embodiments, the antibody, is capable of binding a CD73 antigen at a pH of less than about 7.0. In embodiments, the antibody, is capable of binding a CD73 antigen at a pH of less than about 6.5. In embodiments, the antibody, is capable of binding a CD73 antigen at a pH of less than about 6.0. In embodiments, the antibody, is capable of binding a CD73 antigen at a pH of less than about 5.5. In embodiments, the antibody, is capable of binding a CD73 antigen at a pH of less than about 5. In embodiments, the antibody, is capable of binding a CD73 antigen at a pH of less than about 4.5. In embodiments, the antibody is capable of binding a CD73 antigen at a pH from about 6.0 to about 7.0. In embodiments, the antibody is capable of binding a CD73 antigen at a pH of about 6.0. In embodiments, the antibody is capable of binding a CD73 antigen at a pH of about 6.1. In embodiments, the antibody is capable of binding a CD73 antigen at a pH of about 6.2. In embodiments, the antibody is capable of binding a CD73 antigen at a pH of about 6.3. In embodiments, the antibody is capable of binding a CD73 antigen at a pH of about 6.4. In embodiments, the antibody is capable of binding a CD73 antigen at a pH of about 6.5. In embodiments, the antibody is capable of binding a CD73 antigen at a pH of about 6.6. In embodiments, the antibody is capable of binding a CD73 antigen at a pH of about 6.7. In embodiments, the antibody is capable of binding a CD73 antigen at a pH of about 6.8. In embodiments, the antibody is capable of binding a CD73 antigen at a pH of about 6.9. In embodiments, the antibody is capable of binding a CD73 antigen at a pH of about 7.0. In embodiments, the antibody as set forth in this paragraph is a humanized antibody. In embodiments, the antibody includes a light chain (e.g. humanized light chain) variable region and a heavy chain (e.g. humanized heavy chain) variable region. The light chain variable region includes:

(i) a CDR L1 (e.g. mouse CDR L1) as set forth in SEQ ID NO:1, a CDR L2 (e.g. mouse CDR L2) as set forth in SEQ ID NO:2, a CDR L3 (e.g. mouse CDR L3) as set forth in SEQ ID NO:3 and (ii) a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, an isoleucine at a position corresponding to Kabat position 78, a tyrosine at a position corresponding to Kabat position 85, or a phenylalanine at a position corresponding to Kabat position 87. The heavy chain variable region includes:

(i) a CDR H1 (e.g. a mouse CDR H1) as set forth in SEQ ID NO:4, a CDRH2 (e.g. a mouse CDR H2) as set forth in SEQ ID NO:5, a CDR H3 (e.g. a mouse CDR H3) as set forth in SEQ ID NO:6 and (ii) an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80, or a glutamic acid at a position corresponding to Kabat position 81.

The humanized 1E9 antibodies provided herein are capable of binding CD73 at a pH below 7.5. Thus, in embodiments, the humanized antibody, is capable of binding a CD73 antigen at a pH of less than about 7.5. In embodiments, the humanized antibody, is capable of binding a CD73 antigen at a pH of less than about 7.0. In embodiments, the humanized antibody, is capable of binding a CD73 antigen at a pH of less than about 6.5. In embodiments, the humanized antibody, is capable of binding a CD73 antigen at a pH of less than about 6.0. In embodiments, the humanized antibody, is capable of binding a CD73 antigen at a pH of less than about 5.5. In embodiments, the humanized antibody, is capable of binding a CD73 antigen at a pH of less than about 5. In embodiments, the humanized antibody, is capable of binding a CD73 antigen at a pH of less than about 4.5. In embodiments, the antibody is capable of binding a CD73 antigen at a pH from about 6.0 to about 7.0. In embodiments, the antibody is capable of binding a CD73 antigen at a pH of about 6.0. In embodiments, the antibody is capable of binding a CD73 antigen at a pH of about 6.1. In embodiments, the antibody is capable of binding a CD73 antigen at a pH of about 6.2. In embodiments, the antibody is capable of binding a CD73 antigen at a pH of about 6.3. In embodiments, the antibody is capable of binding a CD73 antigen at a pH of about 6.4. In embodiments, the antibody is capable of binding a CD73 antigen at a pH of about 6.5. In embodiments, the antibody is capable of binding a CD73 antigen at a pH of about 6.6. In embodiments, the antibody is capable of binding a CD73 antigen at a pH of about 6.7. In embodiments, the antibody is capable of binding a CD73 antigen at a pH of about 6.8. In embodiments, the antibody is capable of binding a CD73 antigen at a pH of about 6.9. In embodiments, the antibody is capable of binding a CD73 antigen at a pH of about 7.0.

The humanized 1E9 antibody provided herein including embodiments thereof may include a glutamine at a position corresponding to Kabat position 297.

In embodiments, the humanized 1E9 antibody is bound to a CD73 antigen. In embodiments, the CD73 antigen forms part of a cell. In embodiments, the cell is a lymphoid cell. In embodiments, the cell is a T cell. In embodiments, the cell is a cancer cell.

In one aspect, a humanized 1E9 antibody bound to a CD73 antigen at a pH of less than about 7.5 is provided. In embodiments, the humanized 1E9 antibody includes a humanized light chain variable region and a humanized heavy chain variable region, wherein the humanized light chain variable region includes an isoleucine at a position corresponding to Kabat position 2, a leucine at a position corresponding to Kabat position 4, a serine or alanine at a position corresponding to Kabat position 9, a serine or a threonine at a position corresponding to Kabat position 10, a leucine at a position corresponding to Kabat position 11, a serine at a position corresponding to Kabat position 14, a glycine at a position corresponding to Kabat position 16, an arginine at a position corresponding to Kabat position 18, a threonine at a position corresponding to Kabat position 20 or a glutamine at a position corresponding to Kabat position 42; and wherein the humanized heavy chain variable region includes a glutamine at a position corresponding to Kabat position 1, a valine or glutamic acid at a position corresponding to Kabat position 12, a serine at a position corresponding to Kabat position 17, a methionine or valine at a position corresponding to Kabat position 20, a alanine at a position corresponding to Kabat position 24, a valine at a position corresponding to Kabat position 37, an arginine or alanine at a position corresponding to Kabat position 40, a proline at a position corresponding to Kabat position 41, a glutamine at a position corresponding to Kabat position 43, a glycine at a position corresponding to Kabat position 44, a threonine at a position corresponding to Kabat position 70, a threonine at a position corresponding to Kabat position 75, a methionine at a position corresponding to Kabat position 80, a threonine or arginine at a position corresponding to Kabat position 83, a serine at a position corresponding to Kabat position 84, a glutamic acid at a position corresponding to Kabat position 85, or a valine at a position corresponding to Kabat position 89.

In embodiments, the humanized light chain variable region includes an isoleucine at a position corresponding to Kabat position 2, a leucine at a position corresponding to Kabat position 4, a serine or threonine at a position corresponding to Kabat position 10, a leucine at a position corresponding to Kabat position 11, a threonine at a position corresponding to Kabat position 20 and a glutamine at a position corresponding to Kabat position 42; and the humanized heavy chain variable region includes a glutamine at a position corresponding to Kabat position 1, a serine at a position corresponding to Kabat position 17, a methionine or valine at a position corresponding to Kabat position 20, a alanine at a position corresponding to Kabat position 24, a valine at a position corresponding to Kabat position 37, an arginine or alanine at a position corresponding to Kabat position 40, a proline at a position corresponding to Kabat position 41, a glutamine at a position corresponding to Kabat position 43, a glycine at a position corresponding to Kabat position 44, a threonine at a position corresponding to Kabat position 70, a threonine at a position corresponding to Kabat position 75, a methionine at a position corresponding to Kabat position 80, a threonine or arginine at a position corresponding to Kabat position 83, a serine at a position corresponding to Kabat position 84, a glutamic acid at a position corresponding to Kabat position 85, and a valine at a position corresponding to Kabat position 89.

In embodiments, the humanized light chain variable region includes an isoleucine at a position corresponding to Kabat position 2, a leucine at a position corresponding to Kabat position 4, a serine or threonine at a position corresponding to Kabat position 10, a leucine at a position corresponding to Kabat position 11, a threonine at a position corresponding to Kabat position 20 or a glutamine at a position corresponding to Kabat position 42; and the humanized heavy chain variable region includes a glutamine at a position corresponding to Kabat position 1, a serine at a position corresponding to Kabat position 17, a methionine or valine at a position corresponding to Kabat position 20, a alanine at a position corresponding to Kabat position 24, a valine at a position corresponding to Kabat position 37, an arginine or alanine at a position corresponding to Kabat position 40, a proline at a position corresponding to Kabat position 41, a glutamine at a position corresponding to Kabat position 43, a glycine at a position corresponding to Kabat position 44, a threonine at a position corresponding to Kabat position 70, a threonine at a position corresponding to Kabat position 75, a methionine at a position corresponding to Kabat position 80, a threonine or arginine at a position corresponding to Kabat position 83, a serine at a position corresponding to Kabat position 84, a glutamic acid at a position corresponding to Kabat position 85 or a valine at a position corresponding to Kabat position 89.

In embodiments, the humanized light chain variable region includes an isoleucine at a position corresponding to Kabat position 2, a leucine at a position corresponding to Kabat position 4, a serine or threonine at a position corresponding to Kabat position 10, a leucine at a position corresponding to Kabat position 11, a threonine at a position corresponding to Kabat position 20 and a glutamine at a position corresponding to Kabat position 42; and the humanized heavy chain variable region includes a glutamine at a position corresponding to Kabat position 1, a serine at a position corresponding to Kabat position 17, a methionine or valine at a position corresponding to Kabat position 20, a alanine at a position corresponding to Kabat position 24, a valine at a position corresponding to Kabat position 37, an arginine or alanine at a position corresponding to Kabat position 40, a proline at a position corresponding to Kabat position 41, a glutamine at a position corresponding to Kabat position 43, a glycine at a position corresponding to Kabat position 44, a threonine at a position corresponding to Kabat position 70, a threonine at a position corresponding to Kabat position 75, a methionine at a position corresponding to Kabat position 80, a threonine or arginine at a position corresponding to Kabat position 83, a serine at a position corresponding to Kabat position 84, a glutamic acid at a position corresponding to Kabat position 85 or a valine at a position corresponding to Kabat position 89.

In embodiments, the humanized light chain variable region includes an isoleucine at a position corresponding to Kabat position 2, a leucine at a position corresponding to Kabat position 4, a serine or threonine at a position corresponding to Kabat position 10, a leucine at a position corresponding to Kabat position 11, a threonine at a position corresponding to Kabat position 20 or a glutamine at a position corresponding to Kabat position 42; and the humanized heavy chain variable region includes a glutamine at a position corresponding to Kabat position 1, a serine at a position corresponding to Kabat position 17, a methionine or valine at a position corresponding to Kabat position 20, a alanine at a position corresponding to Kabat position 24, a valine at a position corresponding to Kabat position 37, an arginine or alanine at a position corresponding to Kabat position 40, a proline at a position corresponding to Kabat position 41, a glutamine at a position corresponding to Kabat position 43, a glycine at a position corresponding to Kabat position 44, a threonine at a position corresponding to Kabat position 70, a threonine at a position corresponding to Kabat position 75, a methionine at a position corresponding to Kabat position 80, a threonine or arginine at a position corresponding to Kabat position 83, a serine at a position corresponding to Kabat position 84, a glutamic acid at a position corresponding to Kabat position 85 and a valine at a position corresponding to Kabat position 89.

In embodiments, the humanized light chain variable region includes a serine or alanine at a position corresponding to Kabat position 9, a serine at a position corresponding to Kabat position 14, a glycine at a position corresponding to Kabat position 16 and an arginine at a position corresponding to Kabat position 18; and the humanized heavy chain variable region includes a valine or glutamic acid at a position corresponding to Kabat position 12.

In embodiments, the humanized light chain variable region includes a serine or alanine at a position corresponding to Kabat position 9, a serine at a position corresponding to Kabat position 14, a glycine at a position corresponding to Kabat position 16 or an arginine at a position corresponding to Kabat position 18; and the humanized heavy chain variable region includes a valine or glutamic acid at a position corresponding to Kabat position 12.

In embodiments, the pH is from about 6.0 to about 7.0. In embodiments, the pH is about 6.7. In embodiments, the pH is about 6.3. In embodiments, the antibody inhibits catalytic activity of said CD73 antigen. In embodiments, the antibody includes a humanized light chain variable region including the sequence of SEQ ID NO:36 or SEQ ID NO:37. In embodiments, the antibody includes a humanized heavy chain variable region including the sequence of SEQ ID NO:7. In embodiments, the CD73 antigen forms part of a cell. In embodiments, the CD73 antigen is bound to a solid support.

In another aspect an anti-CD73 antibody is provided. The anti-CD73 binds the same epitope as a 1E9 antibody, wherein the 1E9 antibody includes a humanized light chain variable region including a mouse CDR L1, mouse CDR L2, or mouse CDR L3 and a humanized heavy chain variable region including a mouse CDR H1, mouse CDR H2, or mouse CDR H3.

In another aspect an anti-CD73 antibody is provided. The anti-CD73 binds the same epitope as a 1E9 antibody, wherein the 1E9 antibody includes a humanized light chain variable region and a humanized heavy chain variable region. The humanized light chain variable region includes:
(i) a mouse CDR L1 as set forth in SEQ ID NO:1, a mouse CDR L2 as set forth in SEQ ID NO:2, a mouse CDR L3 as set forth in SEQ ID NO:3 and
(ii) a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, an isoleucine at a position corresponding to Kabat position 78, a tyrosine at a position corresponding to Kabat position 85, or a phenylalanine at a position corresponding to Kabat position 87. The humanized heavy chain variable region includes:
(i) a mouse CDR H1 as set forth in SEQ ID NO:4, a mouse CDR H2 as set forth in SEQ ID NO:5, and a mouse CDR H3 as set forth in SEQ ID NO:6 and
(ii) an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80, or a glutamic acid at a position corresponding to Kabat position 81.

Humanized IgG1 Antibodies

In one aspect, provided herein is a humanized IgG1 antibody including a humanized light chain variable region and a humanized heavy chain variable region, wherein the humanized light chain variable region includes a mouse CDR L1 as set forth in SEQ ID NO:1, a mouse CDR L2 as set forth in SEQ ID NO:2, a mouse CDR L3 as set forth in SEQ ID NO:3 and wherein the humanized heavy chain variable region includes a mouse CDR H1 as set forth in SEQ ID NO:4, a mouse CDR H2 as set forth in SEQ ID NO:5, and a mouse CDR H3 as set forth in SEQ ID NO:6.

In one aspect, provided herein is a humanized IgG4 antibody including a humanized light chain variable region and a humanized heavy chain variable region, wherein the humanized light chain variable region includes a mouse CDR L1 as set forth in SEQ ID NO:1, a mouse CDR L2 as set forth in SEQ ID NO:2, a mouse CDR L3 as set forth in SEQ ID NO:3 and wherein the humanized heavy chain variable region includes a mouse CDR H1 as set forth in SEQ ID NO:4, a mouse CDR H2 as set forth in SEQ ID NO:5, and a mouse CDR H3 as set forth in SEQ ID NO:6.

The humanized light chain variable region may include a mouse CDR L1 as set forth in SEQ ID NO:1, a mouse CDR L2 as set forth in SEQ ID NO:2, or a mouse CDR L3 as set forth in SEQ ID NO:3. The humanized light chain variable region may include a mouse CDR L1 as set forth in SEQ ID NO:1, a mouse CDR L2 as set forth in SEQ ID NO:2, and a mouse CDR L3 as set forth in SEQ ID NO:3. The humanized heavy chain variable region may include a mouse CDR H1 as set forth in SEQ ID NO:4, a mouse CDR H2 as set forth in SEQ ID NO:5, or a mouse CDR H3 as set forth in SEQ ID NO:6. The humanized heavy chain variable region may include a mouse CDR H1 as set forth in SEQ ID NO:4, a mouse CDR H2 as set forth in SEQ ID NO:5, and a mouse CDR H3 as set forth in SEQ ID NO:6. In embodiments, the humanized light chain variable region includes a mouse CDR L1 as set forth in SEQ ID NO:1. In embodiments, the humanized light chain variable region includes a mouse CDR L2 as set forth in SEQ ID NO:2. In embodiments, the humanized light chain variable region includes a mouse CDR L3 as set forth in SEQ ID NO:3. In embodiments, the humanized heavy chain variable region includes a mouse CDR H1 as set forth in SEQ ID NO:4. In embodiments, the humanized heavy chain variable region includes a mouse CDR H2 as set forth in SEQ ID NO:5. In embodiments, the humanized light chain variable region includes a mouse CDR H3 as set forth in SEQ ID NO:6.

In embodiments, the humanized light chain variable region further includes a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, an isoleucine at a position corresponding to Kabat position 78, a tyrosine at a position corresponding to Kabat position 85 or a phenylalanine at a position corresponding to Kabat position 87.

In embodiments, the humanized light chain variable region further includes a valine at a position corresponding to Kabat position 2, a methionine at a position corresponding to Kabat position 4, an aspartic acid or a leucine at a position corresponding to Kabat position 9, a proline or a serine at a position corresponding to Kabat position 12, a lysine or a proline at a position corresponding to Kabat position 18, a alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100, a valine at a position corresponding to Kabat position 104, a glutamic acid or an alanine at a position corresponding to Kabat position 1, a glutamine at a position corresponding to Kabat position 3, a phenylalanine or a threonine at a position corresponding to Kabat position 10, a glutamine at a position corresponding to Kabat position 11, an alanine or a leucine at a position corresponding to Kabat position 13, a threonine at a position corresponding to Kabat position 14, a valine or a proline at a position corresponding to Kabat position 15, a lysine at a position corresponding to Kabat position 16, a glutamic acid or an aspartic acid at a position corresponding to Kabat position 17, a threonine at a position corresponding to Kabat position 22, a lysine at a position corresponding to Kabat position 42, an arginine at a position corresponding to Kabat position 45, an isoleucine at a position corresponding to Kabat position 58, a tyrosine at a position corresponding to Kabat position 67, a phenylalanine at a position corresponding to Kabat position 73, an isoleucine at a position corresponding to Kabat position 78, a tyrosine at a position corresponding to Kabat position 85 and a phenylalanine at a position corresponding to Kabat position 87.

In embodiments, the humanized heavy chain variable region further includes an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80 or a glutamic acid at a position corresponding to Kabat position 81.

In embodiments, the humanized heavy chain variable region further includes an isoleucine at a position corresponding to Kabat position 37, an alanine or a proline at a position corresponding to Kabat position 40, a lysine at a position corresponding to Kabat position 43, a serine at a position corresponding to Kabat position 70, an isoleucine or a threonine at a position corresponding to Kabat position 75, a tryptophan at a position corresponding to Kabat position 82, an arginine or a lysine at a position corresponding to Kabat position 83, a alanine at a position corresponding to Kabat position 84, a serine at a position corresponding to Kabat position 85, a valine or a methionine at a position corresponding to Kabat position 89, a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, a threonine at a position corresponding to Kabat position 87, a glutamic acid at a position corresponding to Kabat position 1, a valine at a position corresponding to Kabat position 24, a arginine at a position corresponding to Kabat position 44, a methionine at a position corresponding to Kabat position 48, a leucine at a position corresponding to Kabat position 80 and a glutamic acid at a position corresponding to Kabat position 81.

In embodiments, the humanized light chain variable region further includes a valine at a position corresponding to Kabat position 2, a methionine at a position corresponding to Kabat position 4, a leucine at a position corresponding to Kabat position 9, a proline at a position corresponding to Kabat position 12, and a proline at a position corresponding to Kabat position 18.

In embodiments, the humanized heavy chain variable region further comprises an isoleucine at a position corresponding to Kabat position 37, a proline at a position corresponding to Kabat position 40, a lysine at a position corresponding to Kabat position 43, a serine at a position corresponding to Kabat position 70, a isoleucine at a position corresponding to Kabat position 75, a tryptophan at a position corresponding to Kabat position 82, a lysine at a position corresponding to Kabat position 83, a alanine at a position corresponding to Kabat position 84, a serine at a position corresponding to Kabat position 85, and a methionine at a position corresponding to Kabat position 89.

In embodiments, the humanized heavy chain variable region comprises a valine at a position corresponding to Kabat position 5, a serine at a position corresponding to Kabat position 7, a valine at a position corresponding to Kabat position 11, a glutamic acid at a position corresponding to Kabat position 12, a valine at a position corresponding to Kabat position 20, an arginine at a position corresponding to Kabat position 38, an alanine at a position corresponding to Kabat position 40, a methionine at a position corresponding to Kabat position 48, an arginine at a position corresponding to Kabat position 66, a valine at a position corresponding to Kabat position 67, an isoleucine at a position corresponding to Kabat position 69, an alanine at a position corresponding to Kabat position 71, a lysine at a position corresponding to Kabat position 73, a threonine at a position corresponding to Kabat position 75, a glutamic acid at a position corresponding to Kabat position 81, an arginine at a position corresponding to Kabat position 83, a threonine at a position corresponding to Kabat position 87, or a valine at a position corresponding to Kabat position 89.

In embodiments, the humanized heavy chain variable region comprises a valine at a position corresponding to Kabat position 5, a serine at a position corresponding to Kabat position 7, a valine at a position corresponding to Kabat position 11, a glutamic acid at a position corresponding to Kabat position 12, a valine at a position corresponding to Kabat position 20, an arginine at a position corresponding to Kabat position 38, an alanine at a position corresponding to Kabat position 40, a methionine at a position corresponding to Kabat position 48, an arginine at a position corresponding to Kabat position 66, a valine at a position corresponding to Kabat position 67, an isoleucine at a position corresponding to Kabat position 69, an alanine at a position corresponding to Kabat position 71, a lysine at a position corresponding to Kabat position 73, a threonine at a position corresponding to Kabat position 75, a glutamic acid at a position corresponding to Kabat position 81, an arginine at a position corresponding to Kabat position 83, a threonine at a position corresponding to Kabat position 87, and a valine at a position corresponding to Kabat position 89.

In embodiments, the humanized IgG1 antibody further includes a glutamine at a position corresponding to Kabat position 297. In embodiments, the humanized IgG1 antibody provided herein including embodiments thereof is bound to a CD73 antigen. In embodiments, the CD73 antigen forms part of a cell. In embodiments, the cell is a T cell. In embodiments, the cell is a cancer cell.

Nucleic Acid Compositions

In one aspect, an isolated nucleic acid encoding a humanized 1E9 antibody provided herein including embodiments thereof is provided. The humanized 1E9 antibody encoded by the isolated nucleic acid is described in detail throughout this application (including the description above and in the examples section). Thus, the humanized antibody encoded by the isolated nucleic acid includes all of the embodiments described herein. For example, the nucleic acid may encode at least one CDR, specific residues involved in binding the epitope, or binding framework residues. For instance, the nucleic acid may encode a humanized light chain including a valine at a position corresponding to Kabat position 2.

In embodiments, the isolated nucleic acid includes the sequence of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17. In embodiments, the isolated nucleic acid includes the sequence of SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 or SEQ ID NO:27. In embodiments, the isolated nucleic acid includes the sequence of SEQ ID NO:8 and the sequence of SEQ ID NO:18. In embodiments, the isolated nucleic acid includes the sequence of SEQ ID NO:9 and the sequence of SEQ ID NO:19. In embodiments, the isolated nucleic acid includes the sequence of SEQ ID NO:10 and the sequence of SEQ ID NO:20. In embodiments, the isolated nucleic acid includes the sequence of SEQ ID NO:11 and the sequence of SEQ ID NO:21. In embodiments, the isolated nucleic acid includes the sequence of SEQ ID NO:12 and the sequence of SEQ ID NO:22. In embodiments, the isolated nucleic acid includes the sequence of SEQ ID NO:13 and the sequence of SEQ ID NO:23. In embodiments, the isolated nucleic acid includes the sequence of SEQ ID NO:14 and the sequence of SEQ ID NO:24. In embodiments, the isolated nucleic acid includes the sequence of SEQ ID NO:15 and the sequence of SEQ ID NO:25. In embodiments, the isolated nucleic acid includes the sequence of SEQ ID NO:16 and the sequence of SEQ ID NO:26. In embodiments, the isolated nucleic acid includes the sequence of SEQ ID NO:17 and the sequence of SEQ ID NO:27.

In embodiments, the isolated nucleic acid includes a codon-optimized sequence. In embodiments, the isolated nucleic acid includes SEQ ID NO:52 or SEQ ID NO:54. In embodiments, the isolated nucleic acid includes SEQ ID NO:52. In embodiments, the isolated nucleic acid includes SEQ ID NO:54. In embodiments, the isolated nucleic acid is SEQ ID NO:52 or SEQ ID NO:54. In embodiments, the isolated nucleic acid is SEQ ID NO:52. In embodiments, the isolated nucleic acid is SEQ ID NO:54.

In another aspect, an isolated nucleic acid encoding a humanized IgG1 antibody provided herein including embodiments is provided. The humanized IgG1 antibody encoded by the isolated nucleic acid is described in detail throughout this application (including the description above and in the examples section). Thus, the humanized antibody encoded by the isolated nucleic acid includes all of the embodiments described herein. For example, the nucleic acid may encode at least one CDR, specific residues involved in binding the epitope, or binding framework residues. Thus, in embodiments the nucleic acid encodes a mouse CDR L1 as set forth in SEQ ID NO:1, a mouse CDR L2 as set forth in SEQ ID NO:2, a mouse CDR L3 as set forth in SEQ ID NO:3. In embodiments, the nucleic acid encodes a mouse CDR H1 as set forth in SEQ ID NO:4, a mouse CDR H2 as set forth in SEQ ID NO:5, and a mouse CDR H3 as set forth in SEQ ID NO:6. In embodiments the nucleic acid encodes a mouse CDR L1 as set forth in SEQ ID NO:1, a mouse CDR L2 as set forth in SEQ ID NO:2, a mouse CDR L3 as set forth in SEQ ID NO:3, a mouse CDR H1 as set forth in SEQ ID NO:4, a mouse CDR H2 as set forth in SEQ ID NO:5, or a mouse CDR H3 as set forth in SEQ ID NO:6. In embodiments the nucleic acid encodes a mouse CDR L1 as set forth in SEQ ID NO:1, a mouse CDR L2 as set forth in SEQ ID NO:2, a mouse CDR L3 as set forth in SEQ ID NO:3, a mouse CDR H1 as set forth in SEQ ID NO:4, a mouse CDR H2 as set forth in SEQ ID NO:5, and a mouse CDR H3 as set forth in SEQ ID NO:6.

In another aspect, an isolated nucleic acid encoding a humanized IgG4 antibody provided herein including embodiments is provided. The humanized IgG4 antibody encoded by the isolated nucleic acid is described in detail throughout this application (including the description above and in the examples section). Thus, the humanized antibody encoded by the isolated nucleic acid includes all of the embodiments described herein. For example, the nucleic acid may encode at least one CDR, specific residues involved in binding the epitope, or binding framework residues. Thus, in embodiments the nucleic acid encodes a mouse CDR L1 as set forth in SEQ ID NO:1, a mouse CDR L2 as set forth in SEQ ID NO:2, a mouse CDR L3 as set forth in SEQ ID NO:3. In embodiments, the nucleic acid encodes a mouse CDR H1 as set forth in SEQ ID NO:4, a mouse CDR H2 as set forth in SEQ ID NO:5, and a mouse CDR H3 as set forth in SEQ ID NO:6. In embodiments the nucleic acid encodes a mouse CDR L1 as set forth in SEQ ID NO:1, a mouse CDR L2 as set forth in SEQ ID NO:2, a mouse CDR L3 as set forth in SEQ ID NO:3, a mouse CDR H1 as set forth in SEQ ID NO:4, a mouse CDR H2 as set forth in SEQ ID NO:5, or a mouse CDR H3 as set forth in SEQ ID NO:6. In embodiments the nucleic acid encodes a mouse CDR L1 as set forth in SEQ ID NO:1, a mouse CDR L2 as set forth in SEQ ID NO:2, a mouse CDR L3 as set forth in SEQ ID NO:3, a mouse CDR H1 as set forth in SEQ ID NO:4, a mouse CDR H2 as set forth in SEQ ID NO:5, and a mouse CDR H3 as set forth in SEQ ID NO:6.

Pharmaceutical Compositions

In another aspect, a pharmaceutical composition including a therapeutically effective amount of a humanized 1E9 antibody provided herein including embodiments thereof and a pharmaceutically acceptable excipient is provided.

In another aspect, a pharmaceutical composition including a therapeutically effective amount of a humanized IgG1 antibody provided herein including embodiments thereof and a pharmaceutically acceptable excipient is provided.

In another aspect, a pharmaceutical composition including a therapeutically effective amount of a humanized IgG4 antibody provided herein including embodiments thereof and a pharmaceutically acceptable excipient is provided.

A therapeutically effective amount as provided herein refers to an amount effective to achieve its intended purpose. The actual amount effective for a particular application will depend, inter alia, on the condition being treated. When administered in methods to treat a disease, the pharmaceutical compositions described herein will contain an amount of active humanized antibody effective to achieve the desired result, e.g., modulating the activity of a target molecule (e.g., CD73), and/or reducing, eliminating, or slowing the progression of disease symptoms (e.g., cancer). Determination of a therapeutically effective amount of a humanized antibody provided herein is well within the capabilities of those skilled in the art, especially in light of the detailed disclosure herein.

Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids such as glycine, carbohydrates, chelating agents, sugars, and other standard ingredients known to those skilled in the art (Remington's Pharmaceutical Science $16^{th}$ edition, Osol, A. Ed. 1980). The mAb is typically present at a concentration of 0.1-100 mg/ml, e.g., 1-10 mg/ml or 10-50 mg/ml, for example 5, 10, 20, 30, 40, 50 or 60 mg/ml.

A pharmaceutical composition including a humanized antibody as described herein can be administered by a variety of methods known in the art. The route and/or mode of administration vary depending upon the desired results. In embodiments, administration is intravenous, intramuscular, intraperitoneal, or subcutaneous, or administered proximal to the site of the target. Pharmaceutically acceptable excipients can be suitable for intravenous, intramuscular, subcutaneous, parenteral, spinal or epidermal administration (e.g., by injection or infusion).

Pharmaceutical compositions of the humanized antibody can be prepared in accordance with methods well known and routinely practiced in the art. See, e.g., Remington: *The Science and Practice of Pharmacy*, Mack Publishing Co., $20^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of the humanized antibody is employed in the pharmaceutical compositions of the invention. The humanized antibodies provided can be formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It may be advantageous to formulate the humanized antibodies in combination with other therapies or agents. It can be advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of humanized antibody calculated to produce the desired therapeutic effect in association with the required pharmaceutical excipient.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors.

A physician or veterinarian can start doses of the humanized antibodies of the invention employed in the pharmaceutical composition at levels lower than that required to achieve the desired therapeutic effect and gradually increase the dosage until the desired effect is achieved. In general, effective doses of the compositions of the present invention vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

The humanized antibody provided herein can be administered on multiple occasions. Intervals between single dosages can be weekly, monthly or yearly. Intervals can also be irregular as indicated by measuring blood levels of the humanized antibody in the patient. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, humanized antibodies show longer half-life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Methods

In one aspect, a method of treating cancer in a subject in need thereof is provided. The method includes administering to the subject a therapeutically effective amount of a humanized 1E9 antibody provided herein including embodiments thereof, thereby treating cancer in the subject. In embodiments, the cancer is a lymphoid cancer.

In one aspect, a method of treating cancer in a subject in need thereof is provided. The method includes administering to the subject a therapeutically effective amount of a humanized IgG1 antibody provided herein including embodiments thereof, thereby treating cancer in the subject. In embodiments, the cancer is a lymphoid cancer.

Methods of Inhibition

In one aspect, a method of inhibiting proliferation of a cell is provided. The method includes (i) contacting a cell with a humanized IgG1 antibody as provided herein including embodiments thereof, thereby forming a contacted cell. (ii) The humanized IgG1 antibody is allowed to bind a CD73 antigen on the contacted cell, thereby inhibiting proliferation of the cell. In embodiments, the cell is a lymphoid cell. In embodiments, the lymphoid cell is a T cell.

In one aspect, a method of inhibiting proliferation of a cell is provided. The method includes (i) contacting a cell with a humanized IgG4 antibody as provided herein including embodiments thereof, thereby forming a contacted cell. (ii) The humanized IgG4 antibody is allowed to bind a CD73 antigen on the contacted cell, thereby inhibiting proliferation of the cell. In embodiments, the cell is a lymphoid cell. In embodiments, the lymphoid cell is a T cell.

Methods of Detecting

In one aspect, a method of detecting a humanized 1E9 antibody bound to a CD73 antigen is provided. The method includes, (i) contacting a humanized 1E9 antibody with a CD73 antigen at a pH of less than about 7.5 and (ii) detecting binding of the humanized 1E9 antibody to the CD73 antigen. In embodiments, the pH is from about 6.0 to about 7.0. In embodiments, the pH is about 6.7. in embodiments, the pH is about 6.3. In embodiments, the detecting binding of step (ii) includes detecting inhibition of CD73 catalytic activity. In embodiments, the CD73 antigen forms part of a cell. In embodiments, the CD73 antigen is bound to a solid support. In embodiments, the humanized 1E9 antibody includes a detectable moiety.

Methods of T-Cell Activation

Provided herein are methods of activating an immunosuppressed (non-activated, non-proliferating) T cell in a cancer environment. Thus, in one aspect a method of activating an immunosuppressed T cell is provided. The method includes, (i) contacting a T cell with a humanized 1E9 antibody as provided herein including embodiments thereof, thereby forming a contacted T cell. (ii) The humanized 1E9 antibody is allowed to bind a CD73 antigen on the contacted T cell, thereby activating the immunosuppressed T cell. In embodiments, the T cell is in a cancer environment. In embodiments, the IFN-gamma secretion of the contacted T cell is increased relative to the absence of the antibody. In embodiments, the proliferation of the contacted T cell is increased relative to the absence of the antibody. An "immunosuppressed T cell" as provided herein is a T cell residing in a cancer environment (in the close vicinity to and/or in physiological contact with a cancer cell or solid tumor), which does not proliferate or secrete detectable amounts of cytokines or express cell surface markers characteristic of activated T cells (e.g., IFN-gamma, CD25, CD38).

Combination Treatment Methods

The methods of treating provided herein including embodiments thereof, may include administration of a second therapeutic agent. Therefore, the methods of treatment as provided herein include administering a humanized 1E9 antibody as provided herein or a humanized IgG1 or IgG4 antibody as provided herein in combination with a second therapeutic agent. The second therapeutic agent may be any composition useful in treating or preventing cancer.

In one aspect, a method of treating cancer in a subject in need thereof is provided. The method includes administering to the subject a therapeutically effective amount of a humanized 1E9 antibody provided herein including embodiments thereof and an effective amount of a second therapeutic agent, thereby treating cancer in the subject.

In another aspect, a method of treating cancer in a subject in need thereof is provided. The method includes administering to the subject a therapeutically effective amount of a humanized IgG1 antibody provided herein including embodiments thereof and an effective amount of a second therapeutic agent, thereby treating cancer in the subject.

In another aspect, a method of treating cancer in a subject in need thereof is provided. The method includes administering to the subject a therapeutically effective amount of a humanized IgG4 antibody provided herein including embodiments thereof and an effective amount of a second therapeutic agent, thereby treating cancer in the subject.

The second therapeutic agent useful for the methods provided herein may be a compound, drug, antagonist, inhibitor, or modulator, having antineoplastic properties or the ability to inhibit the growth or proliferation of cells. In embodiments, the second therapeutic agent is a chemotherapeutic. "Chemotherapeutic" or "chemotherapeutic agent" is used in accordance with its plain ordinary meaning and refers to a chemical composition or compound having antineoplastic properties or the ability to inhibit the growth or proliferation of cells. In embodiments, the second therapeutic agent is radiation therapy. In embodiments, the second therapeutic agent is an agent approved by the FDA or similar regulatory agency of a country other than the USA, for treating cancer.

In embodiments, the second therapeutic agent is a compound. In embodiments, the compound is a purine receptor antagonist. In embodiments, the compound is an $A_{2A}$ adenosine receptor antagonist or $A_{2B}$ adenosine receptor antagonist. In embodiments, the compound is an $A_{2A}$ adenosine receptor antagonist. In embodiments, the compound is an $A_{2B}$ adenosine receptor antagonist. In embodiments, the compound is any one of the compounds disclosed in U.S. Pat. Nos. 9,120,807, 8,450,328 or 8,354,415, which are hereby incorporated by reference and for all purposes. In embodiments, the compound is a thienopyrimidine compound. In embodiments, the compound as the structure of formula:

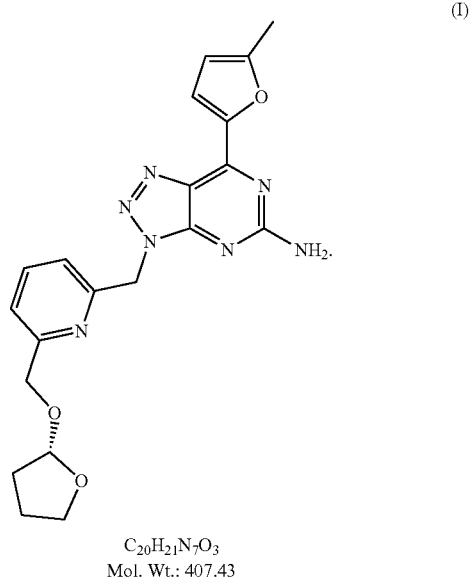 [SMILES: Cc1ccc(-c2nc(N)nc3c2nnn3Cc2cccc(CO[C@H]3CCCO3)n2)o1]

(I)

$C_{20}H_{21}N_7O_3$
Mol. Wt.: 407.43

The term "$A_{2A}$ adenosine receptor" as provided herein includes any of the recombinant or naturally-occurring forms of the $A_{2A}$ adenosine receptor (ADORA2A) or variants or homologs thereof that maintain ADORA2A protein activity (e.g. within at least 50%, 80%, 90%, 95%, 96%, 97%, 98%, 99% or 100% activity compared to ADORA2A). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADORA2A polypeptide. In embodiments, ADORA2A is the protein as identified by the NCBI sequence reference GI:5921992, homolog or functional fragment thereof.

The term "$A_{2B}$ adenosine receptor" as provided herein includes any of the recombinant or naturally-occurring forms of the $A_{2B}$ adenosine receptor (ADORA2B) or variants or homologs thereof that maintain ADORA2B protein activity (e.g. within at least 50%, 80%, 90%, 95%, 96%, 97%, 98%, 99% or 100% activity compared to ADORA2B). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ADORA2B polypeptide. In embodiments, ADORA2B is the protein as identified by the NCBI sequence reference GI:4501951, homolog or functional fragment thereof.

In embodiments, the therapeutic agent is a second humanized antibody. In embodiments, the second humanized antibody is an antibody capable of binding protein programmed cell death ligand 1 (PD-L1). In embodiments, the second humanized antibody is atezolizumab. In embodiments, the second humanized antibody is an antibody capable of binding protein programmed cell death protein 1 (PD-1). In embodiments, the second humanized antibody is an antibody capable of binding CTLA-4.

The term "atezolizumab" or "MPDL3280A" refers a fully humanized, engineered monoclonal antibody of IgG1 isotype against the protein programmed cell death ligand 1 (PD-L1). In the customary sense, atezolizumab refers to CAS Registry number 1380723-44-3.

The term "PDL-1" as provided herein includes any of the recombinant or naturally-occurring forms of the protein programmed cell death ligand 1 (PD-L1) or variants or homologs thereof that maintain PDL-1 protein activity (e.g. within at least 50%, 80%, 90%, 95%, 96%, 97%, 98%, 99% or 100% activity compared to PDL-1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PDL-1 polypeptide. In embodiments, PDL-1 is the protein as identified by the NCBI sequence reference GI:390979639, homolog or functional fragment thereof.

The term "PD-1" as provided herein includes any of the recombinant or naturally-occurring forms of the protein programmed cell death protein 1 (PD-1) or variants or homologs thereof that maintain PD-1 protein activity (e.g. within at least 50%, 80%, 90%, 95%, 96%, 97%, 98%, 99% or 100% activity compared to PD-1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 polypeptide. In embodiments, PD-1 is the protein as identified by the NCBI sequence reference GI:167857792, homolog or functional fragment thereof.

The term "CTLA-4" or "CTLA-4 protein" as provided herein includes any of the recombinant or naturally-occurring forms of the cytotoxic T-lymphocyte-associated protein 4 (CTLA-4) or variants or homologs thereof that maintain CTLA-4 protein activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 polypeptide. In embodiments, CTLA-4 is the protein as identified by the NCBI sequence reference GI:83700231, homolog or functional fragment thereof.

In the provided methods of treatment, additional therapeutic agents can be used that are suitable to the disease (e.g., cancer) being treated. Thus, in some embodiments, the provided methods of treatment further include administering a second therapeutic agent to the subject. Suitable additional therapeutic agents include, but are not limited to analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

According to the methods provided herein, the subject is administered an effective amount of one or more of the therapeutic agents provided herein (i.e. a humanized 1E9 antibody or a humanized IgG1 or IgG4 antibody in combination with, for example, a compound or a second humanized antibody). The terms effective amount and effective dosage are used interchangeably. The term effective amount is defined as any amount necessary to produce a desired physiologic response (e.g., reduction of inflammation). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

EXAMPLES

Example 1

Switching Anti-CD73 (1E9) to Human IgG1 Isotype Eliminates Direct Effects on T Cell Activation Seen with Mouse IgG3 Isotype.

The antibody prepared from the 1E9 hybridoma cell line is a mIgG3 isotype. This antibody has been shown to synergize with PMA to activate T cell proliferation, IL-2 secretion, and upregulation of IL-2 receptor expression (PMID: 2550543). This effect is thought to be through a direct signaling mechanism, as 1E9 mediates these effects on cells that express catalytically inactive CD73 or CD73 that is attached to the cell membrane through a transmembrane region as opposed to the GPI-anchoring mechanism that is used endogenously (PMID: 9113412, 7697732, 8027539). Applicants swapped the variable regions from 1E9 onto a human IgG1 framework, creating a chimeric 1E9 antibody. Chimeric 1E9 does not mediate activation of T cell proliferation or IL-2 receptor (CD25 expression). Thus, Applicants have discovered that switching of the isotype can alter antibody-mediated effects on CD73 signaling.

A Cellular Assay to Evaluate Catalytic Activity of CD73

CD73 is expressed on the cell surface and is an ecto-nucleotidase that hydrolyzes AMP to adenosine and phosphate. In order to assess the catalytic activity of CD73 and the ability of Applicants' anti-CD73 antibodies to inhibit this activity, Applicants used a cellular assay. Cells endogenously expressing CD73 were incubated with anti-CD73 antibodies or an isotype control over a range of concentrations at 37° C. prior to addition of AMP. Cells were incubated with AMP at 37° C. for 20 minutes. Phosphate levels in the media were measured with a commercially available reagent (Sensolyte MG phosphate assay kit, AnaSpec) and are directly proportional to CD73 activity. This assay was adapted from the literature and has been previously described for use in measuring CD73 activity (PMID: 21506751). To Applicants' knowledge, this assay is always performed at a physiological pH of approximately 7.2. Surprisingly, Applicants' were able to show that if the assay was performed at a lower pH to screen for anti-CD73 activities, the ability to block CD73 activity at lower pH was retained. Robust activity at slightly acidic pH would be a desired property of a therapeutic antibody to be used for solid tumor indications as the solid tumor microenvironment is known to be slightly acidic. Applicants found that some antibodies (CPX-002, CPX-005, CPX-006) retain potency in blocking of CD73 activity at lower pH (6.3 or 6.7), while other antibodies (CPX-003, CPX-004) lose potency at lower pH.

Affinity Measurements

Applicants obtained affinity measurements for 5 humanized anti-CD73 candidates (CPX-003, CPX-004, CPX-005, CPX-006, CPX-007) as well as a chimeric antibody (CPX-002) to measure binding of these antibodies to CD73. The results of these affinity measurements are summarized in Table 1.

TABLE 1

| Affinity measurements of humanized and chimeric anti-CD73 antibodies. ||
| Antibody | kD |
| --- | --- |
| CPX-002 | 9.4 nM |
| CPX-003 | 19.5 nM |
| CPX-004 | 17.8 nM |
| CPX-005 | 6.9 nM |
| CPX-006 | 7.1 nM |
| CPX-007 | 15.9 nM |

Specific Chain Associated with Highest CD73 Affinity and Best Potency at Low pH.

Two humanized antibodies (CPX-005, CPX-006) have higher affinity for CD73 and improved potency for inhibition of CD73 activity compared to other candidates. These two antibodies use the same heavy chain and differ only in the light chain. Thus, this particular heavy chain may be important for achieving high affinity and potent inhibition of CD73 activity. In embodiments, the humanized heavy chain variable region includes the sequence of SEQ ID NO:7. In embodiments, the humanized heavy chain variable region is the sequence of SEQ ID NO:7.

Example 2

Humanization of Clone BAP094-01

Applicants have completed the construction of the humanization library of clone BAP094-01 (chimeric 1E9). Double stranded DNA fragments coding for the light chain and heavy chain CDR sequences of BAP094-01 (SEQ ID NO:28 and SEQ ID NO:29, respectively) were combined with pools of human frameworks. Full length variable domains were then cloned into mammalian expression vector. Light chain variable domains were cloned in frame with a secretion signal and a human kappa constant domain. Heavy chain variable domains were cloned in frame with a leader sequence and a human IgG1 constant domain. The quality of the library (diversity of the synthesized variable domains) was confirmed by sequencing (data not shown).

Screening of Humanized Variants

Figure 5:
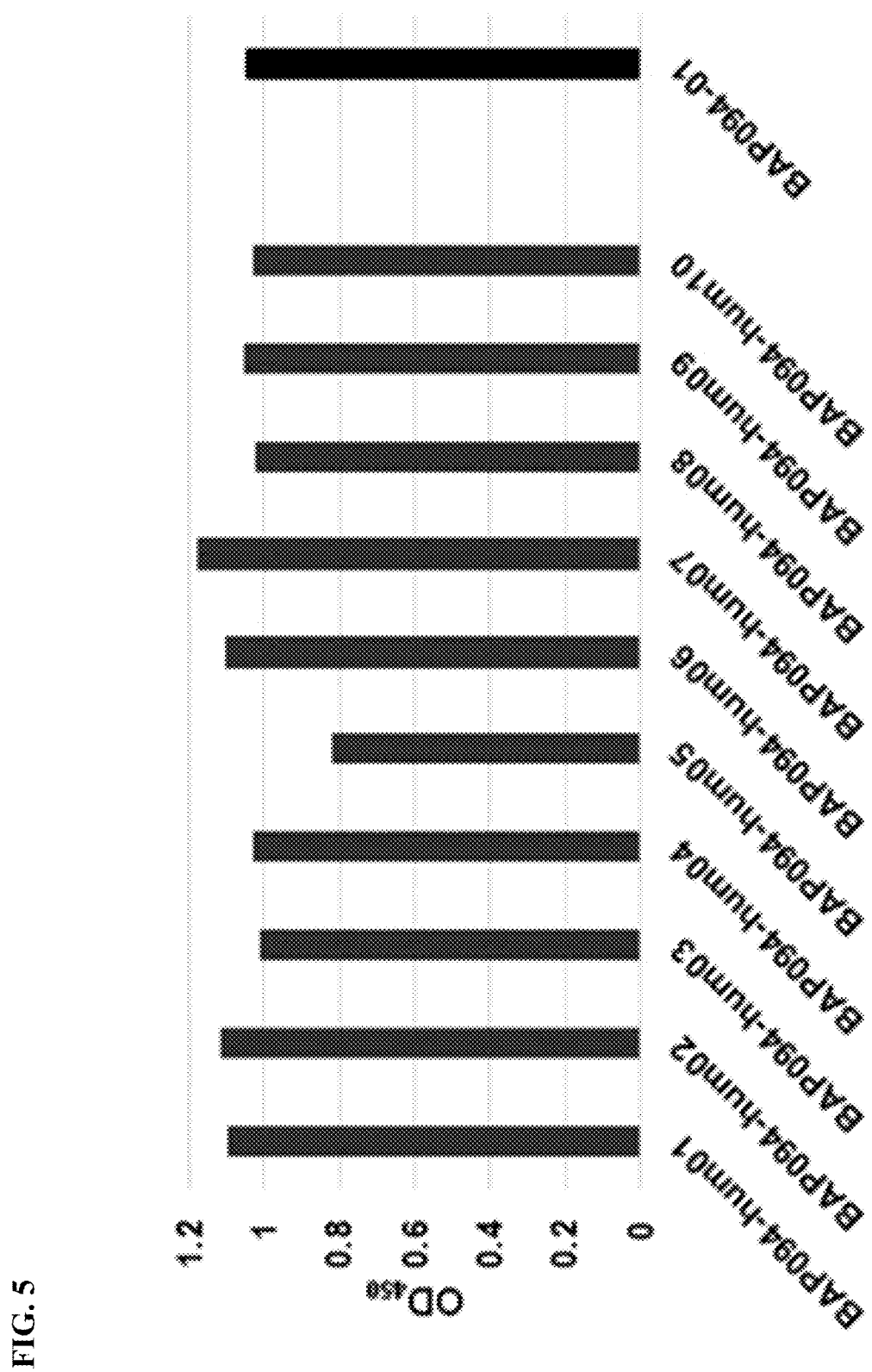
FIG. 5: Cell-based ELISA of selected top 10 humanized variants. CHO cells were seeded in 6 well plates, transfected with BAP094-01 (i.e. a chimeric 1E9 antibody including a variable light chain of SEQ ID NO:30 and a variable heavy chain of SEQ ID NO:41), selected humanized variants or vector only and cultured at 37° C. in DMEM with 10% fetal bovine serum. Supernatants were collected at 48 hours post-transfection. Concentration of antibodies in the supernatant was determined by a quantitation ELISA protocol where unknown values were interpolated to a standard curve. Supernatants were diluted to 50 ng/ml in growth media (DMEM with 10% serum). 100 µl of diluted supernatant was added to the 96 wells containing MDA-MB231 cells (3×10⁴ MDA-MB231 cells/well were seeded the day before) and incubated at room temperature for one hour. Anti-human IgG (H+L) conjugated with HRP (Promega #W4031) was used as secondary antibody for detection. The reactions were stopped at 6 minutes after TMB was added to the wells and read immediately.
Figure 6:
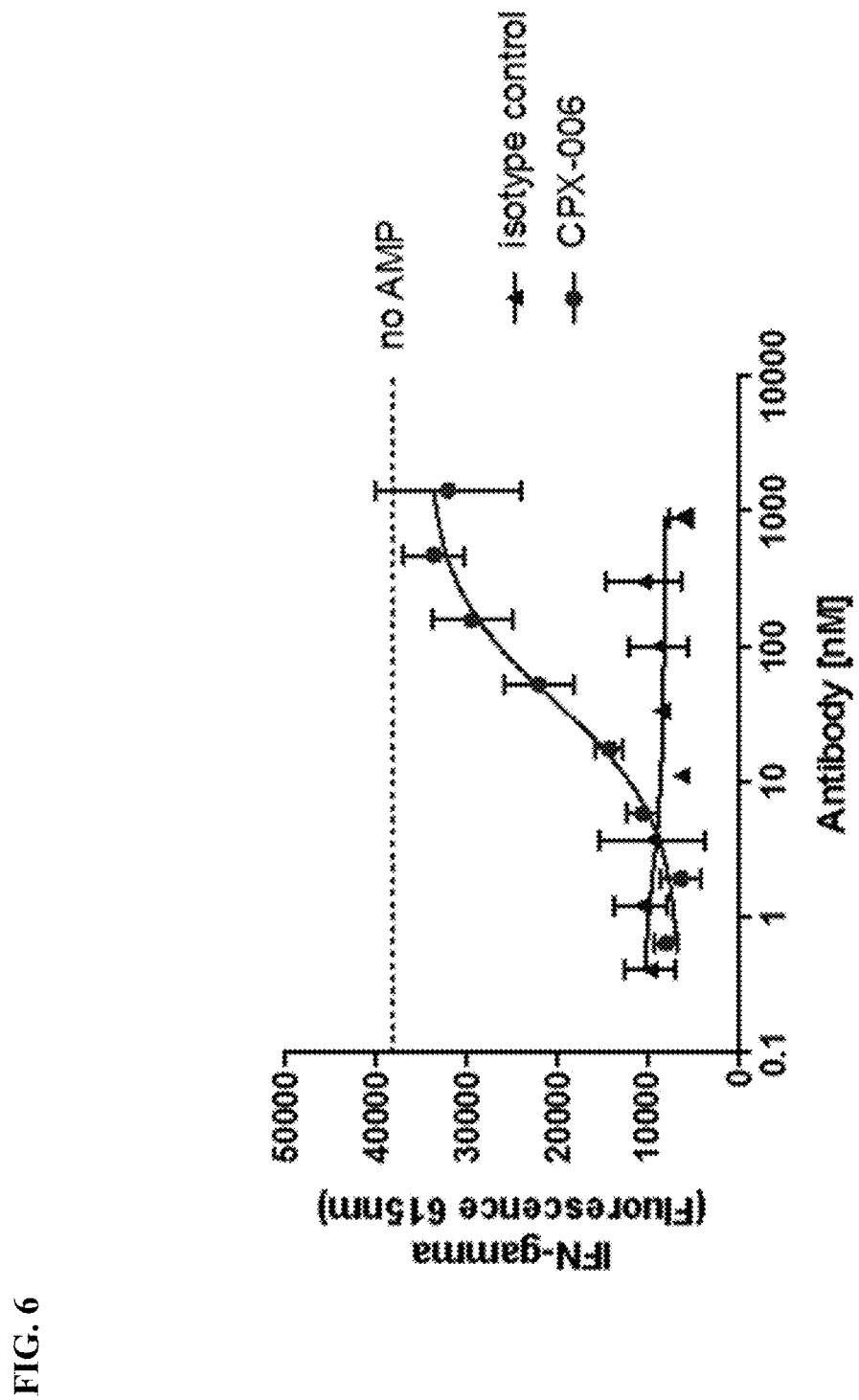
FIG. 6: CPX-006 relieves AMP-dependent suppression of IFN-gamma. Human peripheral blood mononuclear cells were incubated with 1 ug/mL anti-CD3 and anti-CD28 to stimulate T cell proliferation. 1 mM AMP was added to cultures as substrate for cellular CD73 to convert to immunosuppressive adenosine. Cultures were also incubated with anti-CD73 (CPX-006) or isotype control over a range of concentrations. After 4 days in culture, interferon-gamma (IFN-gamma) levels were measured in cell culture media by AlphaLISA. Fluorescence signal is proportional to amounts of IFN-gamma present. CPX-006 relieved AMP-dependent suppression of T cell activity as measured by IFN-gamma secretion.
Figure 7:
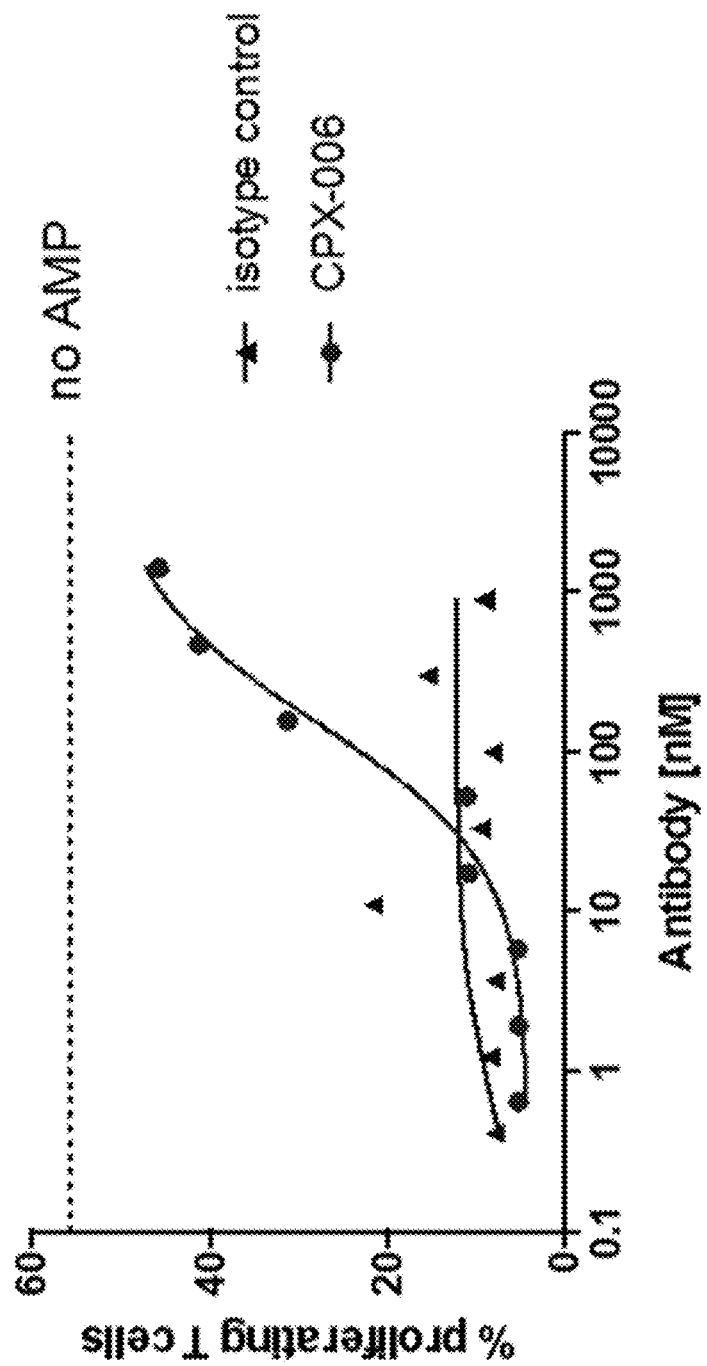
FIG. 7: CPX-006 relieves AMP-dependent suppression of T cell proliferation. Human peripheral blood mononuclear cells were labeled with Cell Trace Violet stain and incubated with 1 ug/mL anti-CD3 and anti-CD28 to stimulate T cell proliferation. 1 mM AMP was added to cultures as substrate for cellular CD73 to convert to immunosuppressive adenosine. Cultures were also incubated with anti-CD73 (CPX-006) or isotype control over a range of concentrations. After 4 days in culture, cells were stained with fluorophore-labeled anti-CD3 antibody and analyzed by flow cytometry. Proliferation of CD3+ T cells was gated as events that had undergone dilution of the Cell Trace Violet dye. CPX-006 relieved AMP-dependent suppression of T cell proliferation.

The humanized clones were arrayed into 96 well plates. Each plate also contains two wells of positive control (BAP094-01, i.e., chimeric 1E9) and negative control (vector only). Plasmid DNA was prepared for each plate and transfected into CHO-S cells in 96 well format. Supernatant was collected at 48 hours post transfection. IgG concentration was determined using ELISA protocol for quantitation of human IgGs. Binding of the humanized clones to CD73 expressed on the surface of MDA-MB-231 cells was determined using a cell based ELISA. Top hits from the primary screening were rearrayed, re-transfected and screened again by cell-based ELISA (FIG. 5).

Sequence Analysis of Top Humanized Variant Hits

Figure 4A:
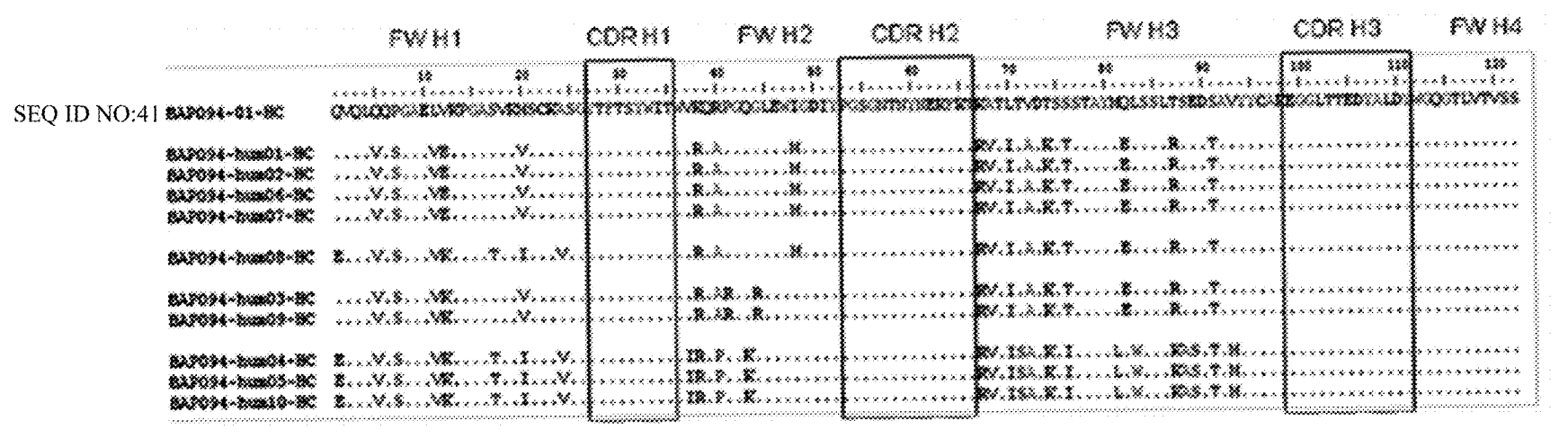
Figure 4B:
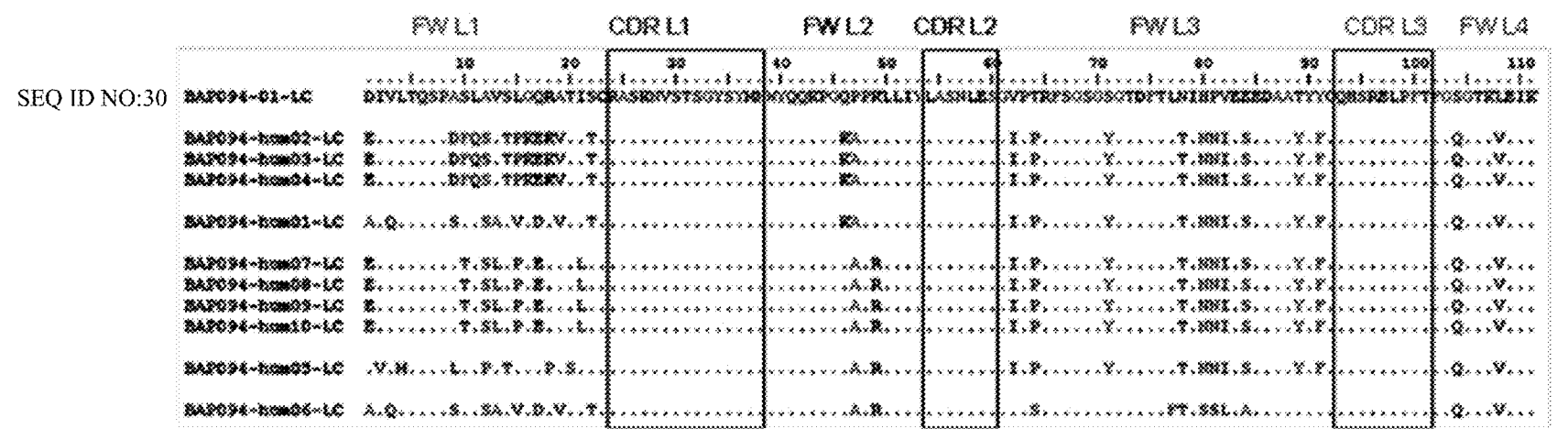

The light chain and heavy chain variable domains of the selected top humanized variant clones were sequenced and aligned with the parental murine sequences of clone BAP094-01 (1E9). Sequence analysis shows that there are four different heavy chains and 5 different light chains within the top 10 clones (FIG. 4A and FIG. 4B). Each top hit has a unique combination of humanized light and heavy chain.

```
                    FORMAL SEQUENCE LISTING

SEQ ID NO: 1:
RASKNVSTSGYSYMH

SEQ ID NO: 2:
LASNLES

SEQ ID NO: 3:
QHSRELPFT

SEQ ID NO: 4:
GYTFTSYWIT

SEQ ID NO: 5:
PGSGNTNYNEKFKT

SEQ ID NO: 6:
EGGLTTEDYALDY

SEQ ID NO: 7:
QVQLVQSGAEVEKPGASVKVSCKASGYTFTSYWITWVRQAPGQGLEWMGDIYPGSGN

TNYNEKFKTRVTITADKSTSTAYMELSSLRSEDTAVYYCAKEGGLTTEDYALDYWGQG

TLVTV

BAP094-hum01-LC SEQ ID NO: 8:
GCCATCCAGTTGACCCAGTCTCCATCCTCCCTGTCTGCATCTGTAGGAGACAGAGTC

ACCATCACTTGCAGGGCCAGCAAAAATGTCAGTACATCTGGCTATAGTTATATGCAC

TGGTATCAGCAGAAACCAGGGAAAGCTCCTAAGCTCCTGATCTATCTTGCATCCAAC

CTAGAATCTGGGATCCCACCTCGGTTCAGTGGCAGCGGGTATGGAACAGATTTTACC

CTCACAATTAATAACATAGAATCTGAGGATGCTGCATATTACTTCTGTCAGCACAGT

AGGGAGCTTCCATTCACGTTCGGCCAAGGGACCAAGGTGGAAATCAAA

BAP094-hum02-LC SEQ ID NO: 9:
GAAATTGTGCTGACTCAGTCTCCAGACTTTCAGTCTGTGACTCCAAAGGAGAAAGTC

ACCATCACCTGCAGGGCCAGCAAAAATGTCAGTACATCTGGCTATAGTTATATGCAC

TGGTATCAGCAGAAACCAGGGAAAGCTCCTAAGCTCCTGATCTATCTTGCATCCAAC

CTAGAATCTGGGATCCCACCTCGATTCAGTGGCAGCGGGTATGGAACAGATTTTACC

CTCACAATTAATAACATAGAATCTGAGGATGCTGCATATTACTTCTGTCAGCACAGT

AGGGAGCTTCCATTCACGTTCGGCCAAGGGACCAAGGTGGAAATCAAA

BAP094-hum03-LC, CPX-003 SEQ ID NO: 10:
GAAATTGTGCTGACTCAGTCTCCAGACTTTCAGTCTGTGACTCCAAAGGAGAAAGTC

ACCATCACCTGCAGGGCCAGCAAAAATGTCAGTACATCTGGCTATAGTTATATGCAC

TGGTATCAGCAGAAACCAGGGAAAGCTCCTAAGCTCCTGATCTATCTTGCATCCAAC

CTAGAATCTGGGATCCCACCTCGATTCAGTGGCAGCGGGTATGGAACAGATTTTACC

CTCACAATTAATAACATAGAATCTGAGGATGCTGCATATTACTTCTGTCAGCACAGT

AGGGAGCTTCCATTCACGTTCGGCCAAGGGACCAAGGTGGAAATCAAA

BAP094-hum04-LC SEQ ID NO: 11:
GAAATTGTGCTGACTCAGTCTCCAGACTTTCAGTCTGTGACTCCAAAGGAGAAAGTC

ACCATCACCTGCAGGGCCAGCAAAAATGTCAGTACATCTGGCTATAGTTATATGCAC

TGGTATCAGCAGAAACCAGGGAAAGCTCCTAAGCTCCTGATCTATCTTGCATCCAAC
```

CTAGAATCTGGGATCCCACCTCGATTCAGTGGCAGCGGGTATGGAACAGATTTTACC

CTCACAATTAATAACATAGAATCTGAGGATGCTGCATATTACTTCTGTCAGCACAGT

AGGGAGCTTCCATTCACGTTCGGCCAAGGGACCAAGGTGGAAATCAAA

BAP094-hum05-LC, CPX-004 SEQ ID NO: 12:
GATGTTGTGATGACTCAGTCTCCACTCTCCCTGCCCGTCACCCTTGGACAGCCGGCC

TCCATCTCCTGCAGGGCCAGCAAAAATGTCAGTACATCTGGCTATAGTTATATGCAC

TGGTACCAGCAGAAACCTGGCCAGGCTCCCAGGCTCCTCATCTATCTTGCATCCAAC

CTAGAATCTGGGATCCCACCTCGATTCAGTGGCAGCGGGTATGGAACAGATTTTACC

CTCACAATTAATAACATAGAATCTGAGGATGCTGCATATTACTTCTGTCAGCACAGT

AGGGAGCTTCCATTCACGTTCGGCCAAGGGACCAAGGTGGAAATCAAA

BAP094-hum06-LC, CPX-005 SEQ ID NO: 13:
GCCATCCAGTTGACCCAGTCTCCATCCTCCCTGTCTGCATCTGTAGGAGACAGAGTC

ACCATCACTTGCAGGGCCAGCAAAAATGTCAGTACATCTGGCTATAGTTATATGCAC

TGGTACCAGCAGAAACCTGGCCAGGCTCCCAGGCTCCTCATCTATCTTGCATCCAAC

CTAGAATCTGGGGTCCCCTCGAGGTTCAGTGGCAGTGGATCTGGGACAGATTTCACC

TTTACCATCAGTAGCCTGGAAGCTGAAGATGCTGCAACATATTACTGTCAGCACAGT

AGGGAGCTTCCATTCACGTTCGGCCAAGGGACCAAGGTGGAAATCAAA

BAP094-hum07-LC, CPX-006, CPX-007 SEQ ID NO: 14:
GAAATTGTGTTGACACAGTCTCCAGCCACCCTGTCTTTGTCTCCAGGGGAAAGAGCC

ACCCTCTCCTGCAGGGCCAGCAAAAATGTCAGTACATCTGGCTATAGTTATATGCAC

TGGTACCAGCAGAAACCTGGCCAGGCTCCCAGGCTCCTCATCTATCTTGCATCCAAC

CTAGAATCTGGGATCCCACCTCGATTCAGTGGCAGCGGGTATGGAACAGATTTTACC

CTCACAATTAATAACATAGAATCTGAGGATGCTGCATATTACTTCTGTCAGCACAGT

AGGGAGCTTCCATTCACGTTCGGCCAAGGGACCAAGGTGGAAATCAAA

BAP094-hum08-LC SEQ ID NO: 15:
GAAATTGTGTTGACACAGTCTCCAGCCACCCTGTCTTTGTCTCCAGGGGAAAGAGCC

ACCCTCTCCTGCAGGGCCAGCAAAAATGTCAGTACATCTGGCTATAGTTATATGCAC

TGGTACCAGCAGAAACCTGGCCAGGCTCCCAGGCTCCTCATCTATCTTGCATCCAAC

CTAGAATCTGGGATCCCACCTCGATTCAGTGGCAGCGGGTATGGAACAGATTTTACC

CTCACAATTAATAACATAGAATCTGAGGATGCTGCATATTACTTCTGTCAGCACAGT

AGGGAGCTTCCATTCACGTTCGGCCAAGGGACCAAGGTGGAAATCAAA

BAP094-hum09-LC SEQ ID NO: 16:
GAAATTGTGTTGACACAGTCTCCAGCCACCCTGTCTTTGTCTCCAGGGGAAAGAGCC

ACCCTCTCCTGCAGGGCCAGCAAAAATGTCAGTACATCTGGCTATAGTTATATGCAC

TGGTACCAGCAGAAACCTGGCCAGGCTCCCAGGCTCCTCATCTATCTTGCATCCAAC

CTAGAATCTGGGATCCCACCTCGATTCAGTGGCAGCGGGTATGGAACAGATTTTACC

CTCACAATTAATAACATAGAATCTGAGGATGCTGCATATTACTTCTGTCAGCACAGT

AGGGAGCTTCCATTCACGTTCGGCCAAGGGACCAAGGTGGAAATCAAA

BAP094-hum10-LC SEQ ID NO: 17:
GAAATTGTGTTGACACAGTCTCCAGCCACCCTGTCTTTGTCTCCAGGGGAAAGAGCC

ACCCTCTCCTGCAGGGCCAGCAAAAATGTCAGTACATCTGGCTATAGTTATATGCAC

TGGTACCAGCAGAAACCTGGCCAGGCTCCCAGGCTCCTCATCTATCTTGCATCCAAC

| FORMAL SEQUENCE LISTING |
| --- |

CTAGAATCTGGGATCCCACCTCGATTCAGTGGCAGCGGGTATGGAACAGATTTTACC

CTCACAATTAATAACATAGAATCTGAGGATGCTGCATATTACTTCTGTCAGCACAGT

AGGGAGCTTCCATTCACGTTCGGCCAAGGGACCAAGGTGGAAATCAAA

BAP094-hum01-HC SEQ ID NO: 18:
CAGGTTCAGCTGGTGCAGTCTGGAGCTGAGGTGGAGAAGCCTGGGGCCTCAGTGAA

GGTCTCCTGCAAGGCTTCTGGCTACACCTTCACCAGCTACTGGATAACCTGGGTGCG

ACAGGCCCCTGGACAAGGGCTTGAGTGGATGGGTGATATTTATCCTGGTAGTGGTAA

TACTAACTACAATGAGAAGTTCAAGACCAGAGTCACGATTACCGCGGACAAATCCA

CGAGCACAGCCTACATGGAGCTGAGCAGCCTGAGATCTGAGGACACGGCCGTGTAT

TACTGTGCAAAAGAGGGAGGTCTTACTACGGAGGATTATGCTTTGGACTACTGGGGC

CAGGGAACGCTGGTCACCGTCAGCTCA

BAP094-hum02-HC SEQ ID NO: 19:
CAGGTTCAGCTGGTGCAGTCTGGAGCTGAGGTGGAGAAGCCTGGGGCCTCAGTGAA

GGTCTCCTGCAAGGCTTCTGGCTACACCTTCACCAGCTACTGGATAACCTGGGTGCG

ACAGGCCCCTGGACAAGGGCTTGAGTGGATGGGTGATATTTATCCTGGTAGTGGTAA

TACTAACTACAATGAGAAGTTCAAGACCAGAGTCACGATTACCGCGGACAAATCCA

CGAGCACAGCCTACATGGAGCTGAGCAGCCTGAGATCTGAGGACACGGCCGTGTAT

TACTGTGCAAAAGAGGGAGGTCTTACTACGGAGGATTATGCTTTGGACTACTGGGGC

CAGGGAACGCTGGTCACCGTCAGCTCA

BAP094-hum03-HC, CPX-003, CPX-007 SEQ ID NO: 20:
CAGGTTCAGCTGGTGCAGTCTGGAGCTGAGGTGAAGAAGCCTGGGGCCTCAGTGAA

GGTCTCCTGCAAGGCTTCTGGCTACACCTTCACCAGCTACTGGATAACCTGGGTGCG

ACAGGCTCGTGGACAACGCCTTGAGTGGATAGGTGATATTTATCCTGGTAGTGGTAA

TACTAACTACAATGAGAAGTTCAAGACCAGAGTCACGATTACCGCGGACAAATCCA

CGAGCACAGCCTACATGGAGCTGAGCAGCCTGAGATCTGAGGACACGGCCGTGTAT

TACTGTGCAAAAGAGGGAGGTCTTACTACGGAGGATTATGCTTTGGACTACTGGGGC

CAGGGAACGCTGGTCACCGTCAGCTCA

BAP094-hum04-HC SEQ ID NO: 21:
GAGGTCCAGCTGGTACAGTCTGGGGCTGAGGTGAAGAAGCCTGGGGCTACAGTGAA

AATCTCCTGCAAGGTTTCTGGCTACACCTTCACCAGCTACTGGATAACCTGGATCCG

CCAGCCCCCAGGGAAGGGGCTGGAGTGGATTGGTGATATTTATCCTGGTAGTGGTA

ATACTAACTACAATGAGAAGTTCAAGACCAGAGTCACCATCTCAGCCGACAAGTCC

ATCAGCACCGCCTACCTGCAGTGGAGCAGCCTGAAGGCCTCGGACACCGCCATGTA

TTACTGTGCAAAAGAGGGAGGTCTTACTACGGAGGATTATGCTTTGGACTACTGGGG

CCAGGGAACGCTGGTCACCGTCAGCTCA

BAP094-hum05-HC, CPX-004 SEQ ID NO: 22:
GAGGTCCAGCTGGTACAGTCTGGGGCTGAGGTGAAGAAGCCTGGGGCTACAGTGAA

AATCTCCTGCAAGGTTTCTGGCTACACCTTCACCAGCTACTGGATAACCTGGATCCG

CCAGCCCCCAGGGAAGGGGCTGGAGTGGATTGGTGATATTTATCCTGGTAGTGGTA

ATACTAACTACAATGAGAAGTTCAAGACCAGAGTCACCATCTCAGCCGACAAGTCC

ATCAGCACCGCCTACCTGCAGTGGAGCAGCCTGAAGGCCTCGGACACCGCCATGTA

TTACTGTGCAAAAGAGGGAGGTCTTACTACGGAGGATTATGCTTTGGACTACTGGGG

CCAGGGAACGCTGGTCACCGTCAGCTCA

BAP094-hum06-HC, CPX-005, CPX-006 SEQ ID NO: 23:
CAGGTTCAGCTGGTGCAGTCTGGAGCTGAGGTGGAGAAGCCTGGGGCCTCAGTGAA

GGTCTCCTGCAAGGCTTCTGGCTACACCTTCACCAGCTACTGGATAACCTGGGTGCG

ACAGGCCCCTGGACAAGGGCTTGAGTGGATGGGTGATATTTATCCTGGTAGTGGTAA

TACTAACTACAATGAGAAGTTCAAGACCAGAGTCACGATTACCGCGGACAAATCCA

CGAGCACAGCCTACATGGAGCTGAGCAGCCTGAGATCTGAGGACACGGCCGTGTAT

TACTGTGCAAAAGAGGGAGGTCTTACTACGGAGGATTATGCTTTGGACTACTGGGC

CAGGGAACGCTGGTCACCGTCAGCTCA

BAP094-hum07-HC SEQ ID NO: 24:
CAGGTTCAGCTGGTGCAGTCTGGAGCTGAGGTGGAGAAGCCTGGGGCCTCAGTGAA

GGTCTCCTGCAAGGCTTCTGGCTACACCTTCACCAGCTACTGGATAACCTGGGTGCG

ACAGGCCCCTGGACAAGGGCTTGAGTGGATGGGTGATATTTATCCTGGTAGTGGTAA

TACTAACTACAATGAGAAGTTCAAGACCAGAGTCACGATTACCGCGGACAAATCCA

CGAGCACAGCCTACATGGAGCTGAGCAGCCTGAGATCTGAGGACACGGCCGTGTAT

TACTGTGCAAAAGAGGGAGGTCTTACTACGGAGGATTATGCTTTGGACTACTGGGC

CAGGGAACGCTGGTCACCGTCAGCTCA

BAP094-hum08-HC SEQ ID NO: 25:
GAGGTCCAGCTGGTACAGTCTGGGGCTGAGGTGAAGAAGCCTGGGGCTACAGTGAA

AATCTCCTGCAAGGTTTCTGGCTACACCTTCACCAGCTACTGGATAACCTGGGTGCG

ACAGGCCCCTGGACAAGGGCTTGAGTGGATGGGTGATATTTATCCTGGTAGTGGTAA

TACTAACTACAATGAGAAGTTCAAGACCAGAGTCACGATTACCGCGGACAAATCCA

CGAGCACAGCCTACATGGAGCTGAGCAGCCTGAGATCTGAGGACACGGCCGTGTAT

TACTGTGCAAAAGAGGGAGGTCTTACTACGGAGGATTATGCTTTGGACTACTGGGC

CAGGGAACGCTGGTCACCGTCAGCTCA

BAP094-hum09-HC SEQ ID NO: 26:
CAGGTTCAGCTGGTGCAGTCTGGAGCTGAGGTGAAGAAGCCTGGGGCCTCAGTGAA

GGTCTCCTGCAAGGCTTCTGGCTACACCTTCACCAGCTACTGGATAACCTGGGTGCG

ACAGGCTCGTGGACAACGCCTTGAGTGGATAGGTGATATTTATCCTGGTAGTGGTAA

TACTAACTACAATGAGAAGTTCAAGACCAGAGTCACGATTACCGCGGACAAATCCA

CGAGCACAGCCTACATGGAGCTGAGCAGCCTGAGATCTGAGGACACGGCCGTGTAT

TACTGTGCAAAAGAGGGAGGTCTTACTACGGAGGATTATGCTTTGGACTACTGGGC

CAGGGAACGCTGGTCACCGTCAGCTCA

BAP094-hum10-HC SEQ ID NO: 27:
GAGGTCCAGCTGGTACAGTCTGGGGCTGAGGTGAAGAAGCCTGGGGCTACAGTGAA

AATCTCCTGCAAGGTTTCTGGCTACACCTTCACCAGCTACTGGATAACCTGGATCCG

CCAGCCCCCAGGGAAGGGGCTGGAGTGGATTGGTGATATTTATCCTGGTAGTGGTA

ATACTAACTACAATGAGAAGTTCAAGACCAGAGTCACCATCTCAGCCGACAAGTCC

| FORMAL SEQUENCE LISTING |
| --- |
| ATCAGCACCGCCTACCTGCAGTGGAGCAGCCTGAAGGCCTCGGACACCGCCATGTA |
| TTACTGTGCAAAAGAGGGAGGTCTTACTACGGAGGATTATGCTTTGGACTACTGGGG |
| CCAGGGAACGCTGGTCACCGTCAGCTCA |
| |
| [0253]BAP094-01-LC CPX-002 (chimeric) SEQ ID NO: 28: |
| GACATTGTGCTGACACAGTCTCCTGCTTCCTTAGCTGTATCTCTGGGGCAGAGGGCC |
| ACCATCTCATGCAGGGCCAGCAAAAATGTCAGTACATCTGGCTATAGTTATATGCAC |
| TGGTACCAACAGAAACCAGGACAGCCACCCAAACTCCTCATCTATCTTGCATCCAAC |
| CTAGAATCTGGGGTCCCTACCAGGTTCAGTGGCAGTGGGTCTGGGACAGACTTCACC |
| CTCAACATCCATCCTGTGGAGGAGGAGGATGCTGCAACCTATTACTGTCAGCACAGT |
| AGGGAGCTTCCATTCACGTTCGGCTCGGGGACAAAGTTGGAAATAAAA |
| |
| [0254]BAP094-01-HC CPX-002 (chimeric) SEQ ID NO: 29: |
| CAGGTCCAACTGCAGCAGCCTGGGGCTGAGCTTGTGAAGCCTGGGGCTTCAGTGAA |
| GATGTCCTGCAAGGCTTCTGGCTACACCTTCACCAGCTACTGGATAACCTGGGTGAA |
| GCAGAGGCCTGGACAAGGCCTTGAGTGGATTGGAGATATTTATCCTGGTAGTGGTA |
| ATACTAACTACAATGAGAAGTTCAAGACCAAGGCCACACTGACTGTAGACACATCC |
| TCCAGCACAGCCTACATGCAGCTCAGCAGCCTGACATCTGAGGACTCTGCGGTCTAT |
| TACTGTGCAAAAGAGGGAGGTCTTACTACGGAGGATTATGCTTTGGACTACTGGGGC |
| CAGGGAACGCTGGTCACCGTCAGCTCA |
| |
| BAP094-01-LC SEQ ID NO: 30: |
| DIVLTQSPASLAVSLGQRATISCRASKNVSTSGYSYMHWYQQKPGQPPKLLIYLASNLES |
| GVPTRFSGSGSGTDFTLNIHPVEEEDAATYYCQHSRELPFTFGSGTKLEIK |
| |
| BAP094-hum01-LC SEQ ID NO: 31: |
| AIQLTQSPSSLSASVGDRVTITCRASKNVSTSGYSYMHWYQQKPGKAPKLLIYLASNLES |
| GIPPRFSGSGYGTDFTLTINNIESEDAAYYFCQHSRELPFTFGQGTKVEIK |
| |
| BAP094-hum02-LC SEQ ID NO: 32: |
| EIVLTQSPDFQSVTPKEKVTITCRASKNVSTSGYSYMHWYQQKPGKAPKLLIYLASNLES |
| GIPPRFSGSGYGTDFTLTINNIESEDAAYYFCQHSRELPFTFGQGTKVEIK |
| |
| BAP094-hum03-LC SEQ ID NO: 33: |
| EIVLTQSPDFQSVTPKEKVTITCRASKNVSTSGYSYMHWYQQKPGKAPKLLIYLASNLES |
| GIPPRFSGSGYGTDFTLTINNIESEDAAYYFCQHSRELPFTFGQGTKVEI |
| |
| BAP094-hum04-LC SEQ ID NO: 34: |
| EIVLTQSPDFQSVTPKEKVTITCRASKNVSTSGYSYMHWYQQKPGKAPKLLIYLASNLES |
| GIPPRFSGSGYGTDFTLTINNIESEDAAYYFCQHSRELPFTFGQGTKVEIK |
| |
| BAP094-hum05-LC SEQ ID NO: 35: |
| DVVMTQSPLSLPVTLGQPASISCRASKNVSTSGYSYMHWYQQKPGQAPRLLIYLASNLE |
| SGIPPRFSGSGYGTDFTLTINNIESEDAAYYFCQHSRELPFTFGQGTKVEIK |
| |
| BAP094-hum06-LC SEQ ID NO: 36: |
| AIQLTQSPSSLSASVGDRVTITCRASKNVSTSGYSYMHWYQQKPGQAPRLLIYLASNLES |
| GVPSRFSGSGSGTDFTFTISSLEAEDAATYYCQHSRELPFTFGQGTKVEIK |
| |
| BAP094-hum07-LC SEQ ID NO: 37: |
| EIVLTQSPATLSLSPGERATLSCRASKNVSTSGYSYMHWYQQKPGQAPRLLIYLASNLES |
| GIPPRFSGSGYGTDFTLTINNIESEDAAYYFCQHSRELPFTFGQGTKVEIK |

| FORMAL SEQUENCE LISTING |
|---|
| BAP094-hum08-LC SEQ ID NO: 38:<br>EIVLTQSPATLSLSPGERATLSCRASKNVSTSGYSYMHWYQQKPGQAPRLLIYLASNLES<br><br>GIPPRFSGSGYGTDFTLTINNIESEDAAYYFCQHSRELPFTFGQGTKVEIK |
| BAP094-hum09-LC SEQ ID NO: 39:<br>EIVLTQSPATLSLSPGERATLSCRASKNVSTSGYSYMHWYQQKPGQAPRLLIYLASNLES<br><br>GIPPRFSGSGYGTDFTLTINNIESEDAAYYFCQHSRELPFTFGQGTKVEIK |
| BAP094-hum10-LC SEQ ID NO: 40:<br>EIVLTQSPATLSLSPGERATLSCRASKNVSTSGYSYMHWYQQKPGQAPRLLIYLASNLES<br><br>GIPPRFSGSGYGTDFTLTINNIESEDAAYYFCQHSRELPFTFGQGTKVEIK |
| BAP094-01-HC SEQ ID NO: 41:<br>QVQLQQPGAELVKPGASVKMSCKASGYTFTSYWITWVKQRPGQGLEWIGDIYPGSGNT<br><br>NYNEKFKTKATLTVDTSSSTAYMQLSSLTSEDSAVYYCAKEGGLTTEDYALDYWGQGT<br><br>LVTVSS |
| BAP094-hum01-HC SEQ ID NO: 42:<br>QVQLVQSGAEVEKPGASVKVSCKASGYTFTSYWITWVRQAPGQGLEWMGDIYPGSGN<br><br>TNYNEKFKTRVTITADKSTSTAYMELSSLRSEDTAVYYCAKEGGLTTEDYALDYWGQG<br><br>TLVTVSS |
| BAP094-hum02-HC SEQ ID NO: 43:<br>QVQLVQSGAEVEKPGASVKVSCKASGYTFTSYWITWVRQAPGQGLEWMGDIYPGSGN<br><br>TNYNEKFKTRVTITADKSTSTAYMELSSLRSEDTAVYYCAKEGGLTTEDYALDYWGQG<br><br>TLVTVSS |
| BAP094-hum03-HC SEQ ID NO: 44:<br>QVQLVQSGAEVKKPGASVKVSCKASGYTFTSYWITWVRQARGQRLEWIGDIYPGSGNT<br><br>NYNEKFKTRVTITADKSTSTAYMELSSLRSEDTAVYYCAKEGGLTTEDYALDYWGQGT<br><br>LVTVSS |
| BAP094-hum04-HC SEQ ID NO: 45:<br>EVQLVQSGAEVKKPGATVKISCKVSGYTFTSYWITWIRQPPGKGLEWIGDIYPGSGNTN<br><br>YNEKFKTRVTISADKSISTAYLQWSSLKASDTAMYYCAKEGGLTTEDYALDYWGQGTL<br><br>VTVSS |
| BAP094-hum05-HC SEQ ID NO: 46:<br>EVQLVQSGAEVKKPGATVKISCKVSGYTFTSYWITWIRQPPGKGLEWIGDIYPGSGNTN<br><br>YNEKFKTRVTISADKSISTAYLQWSSLKASDTAMYYCAKEGGLTTEDYALDYWGQGTL<br><br>VTVSS |
| BAP094-hum06-HC SEQ ID NO: 47:<br>QVQLVQSGAEVEKPGASVKVSCKASGYTFTSYWITWVRQAPGQGLEWMGDIYPGSGN<br><br>TNYNEKFKTRVTITADKSTSTAYMELSSLRSEDTAVYYCAKEGGLTTEDYALDYWGQG<br><br>TLVTVSS |
| BAP094-hum07-HC SEQ ID NO: 48:<br>QVQLVQSGAEVEKPGASVKVSCKASGYTFTSYWITWVRQAPGQGLEWMGDIYPGSGN<br><br>TNYNEKFKTRVTITADKSTSTAYMELSSLRSEDTAVYYCAKEGGLTTEDYALDYWGQG<br><br>TLVTVSS |
| BAP094-hum08-HC SEQ ID NO: 49:<br>EVQLVQSGAEVKKPGATVKISCKVSGYTFTSYWITWVRQAPGQGLEWMGDIYPGSGNT<br><br>NYNEKFKTRVTITADKSTSTAYMELSSLRSEDTAVYYCAKEGGLTTEDYALDYWGQGT<br><br>LVTVSS |

FORMAL SEQUENCE LISTING

BAP094-hum09-HC SEQ ID NO: 50:
QVQLVQSGAEVKKPGASVKVSCKASGYTFTSYWITWVRQARGQRLEWIGDIYPGSGNT

NYNEKFKTRVTITADKSTSTAYMELSSLRSEDTAVYYCAKEGGLTTEDYALDYWGQGT

LVTVSS

BAP094-hum10-HC SEQ ID NO: 51:
EVQLVQSGAEVKKPGATVKISCKVSGYTFTSYWITWIRQPPGKGLEWIGDIYPGSGNTN

YNEKFKTRVTISADKSISTAYLQWSSLKASDTAMYYCAKEGGLTTEDYALDYWGQGTL

VTVSS

CPX-006_HC (codon-optimized) SEQ ID NO: 52:
AAGCTTGCCGCCACCATGGAATGGTCCTGGGTGTTCCTGTTCTTCCTGTCCGTGACCA

CCGGCGTGCACTCCCAGGTGCAGCTGGTGCAGTCTGGCGCCGAGGTGGAAAAGCCT

GGCGCCTCTGTGAAGGTGTCCTGCAAGGCCTCCGGCTACACCTTTACCAGCTACTGG

ATCACCTGGGTGCGACAGGCTCCTGGACAGGGCCTGGAATGGATGGGCGACATCTA

CCCTGGCTCCGGCAACACCAACTACAACGAGAAGTTCAAGACCCGCGTGACCATCA

CCGCCGACAAGTCCACCTCCACCGCCTACATGGAACTGTCCTCCCTGCGGAGCGAGG

ACACCGCCGTGTACTACTGTGCTAAAGAGGGCGGCCTGACCACCGAGGACTACGCC

CTGGATTATTGGGGCCAGGGCACCCTCGTGACCGTGTCCTCTGCTTCTACCAAGGGC

CCCTCCGTGTTCCCTCTGGCCCCTTCCAGCAAGTCTACCTCTGGCGGCACAGCCGCTC

TGGGCTGCCTCGTGAAGGACTACTTCCCCGAGCCCGTGACAGTGTCTTGGAACTCTG

GCGCCCTGACCAGCGGAGTGCACACCTTCCCTGCTGTGCTGCAGTCCTCCGGCCTGT

ACTCCCTGTCCTCCGTCGTGACTGTGCCCTCCAGCTCTCTGGGCACCCAGACCTACAT

CTGCAACGTGAACCACAAGCCCTCCAACACCAAGGTGGACAAGAAGGTGGAACCCA

AGTCCTGCGACAAGACCCACACCTGTCCCCCTTGTCCTGCCCCTGAACTGCTGGGCG

GACCCTCTGTGTTTCTGTTCCCCCCAAAGCCCAAGGACACCCTGATGATCTCCCGGA

CCCCCGAAGTGACCTGCGTGGTGGTGGATGTGTCCCACGAGGACCCTGAAGTGAAG

TTCAATTGGTACGTGGACGGCGTGGAAGTGCACAACGCCAAGACCAAGCCTAGAGA

GGAACAGTACCAGTCCACCTACCGGGTGGTGTCCGTGCTGACCGTGCTGCACCAGG

ATTGGCTGAACGGCAAAGAGTACAAGTGCAAGGTGTCCAACAAGGCTCTGCCTGCC

CCCATCGAAAAGACCATCTCCAAGGCCAAGGGCCAGCCCCGGGAACCCCAGGTGTA

CACACTGCCCCCTAGCAGGGACGAGCTGACCAAGAACCAGGTGTCCCTGACCTGTC

TCGTGAAAGGCTTCTACCCCTCCGATATCGCCGTGGAATGGGAGTCCAACGGCCAGC

CTGAGAACAACTACAAGACCACCCCCCCTGTGCTGGACTCCGACGGCTCATTCTTTC

TGTACTCCAAGCTGACAGTGGACAAGTCCCGGTGGCAGCAGGGCAACGTGTTCTCCT

GCAGCGTGATGCACGAGGCCCTGCACAACCACTACACCCAGAAGTCCCTGTCCCTG

AGCCCCGGCAAGTGATGAATTC

CPX-006_HC (codon-optimized) SEQ ID NO: 53:
MEWSWVFLFFLSVTTGVHS

QVQLVQSGAEVEKPGASVKVSCKASGYTFTSYWITWVRQAPGQGLEWMGDIYPGSGN

TNYNEKFKTRVTITADKSTSTAYMELSSLRSEDTAVYYCAKEGGLTTEDYALDYWGQG

TLVTVSSASTKGPSVFPLAPSSKSTSGGTAALGCLVKDYFPEPVTVSWNSGALTSGVHTF

FORMAL SEQUENCE LISTING

PAVLQSSGLYSLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVDGVEVHNAKT

KPREEQYQSTYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGK

CPX-006_LC (codon-optimized) SEQ ID NO: 54:
AAGCTTGCCGCCACCATGTCCGTGCCTACCCAGGTGCTGGGACTGCTGCTGCTGTGG

CTGACCGATGCCAGATGCGAGATCGTGCTGACCCAGTCCCCTGCCACCCTGTCACTG

TCTCCAGGCGAGAGAGCCACCCTGAGCTGCCGGGCCTCCAAGAACGTGTCCACCTC

CGGCTACTCCTACATGCACTGGTATCAGCAGAAGCCCGGCCAGGCCCCCAGACTGCT

GATCTACCTGGCCTCCAACCTGGAATCCGGCATCCCCCCTAGATTCTCCGGCTCTGG

CTACGGCACCGACTTCACCCTGACCATCAACAACATCGAGTCCGAGGACGCCGCCT

ACTACTTCTGCCAGCACTCCAGAGAGCTGCCCTTCACCTTTGGCCAGGGCACCAAGG

TGGAAATCAAGCGGACCGTGGCCGCTCCCTCCGTGTTCATCTTCCCACCTTCCGACG

AGCAGCTGAAGTCCGGCACCGCTTCTGTCGTGTGCCTGCTGAACAACTTCTACCCCC

GCGAGGCCAAGGTGCAGTGGAAGGTGGACAACGCCCTGCAGTCCGGCAACTCCCAG

GAATCCGTGACCGAGCAGGACTCCAAGGACAGCACCTACTCCCTGTCCTCTACCCTG

ACCCTGTCCAAGGCCGACTACGAGAAGCACAAGGTGTACGCCTGCGAAGTGACCCA

CCAGGGCCTGTCTAGCCCCGTGACCAAGTCTTTCAACCGGGGCGAGTGCTGATGAAT

TC

CPX-006_LC (codon-optimized) SEQ ID NO: 55:
MSVPTQVLGLLLLWLTDARC

EIVLTQSPATLSLSPGERATLSCRASKNVSTSGYSYMHWYQQKPGQAPRLLIYLASNLES

GIPPRFSGSGYGTDFTLTINNIESEDAAYYFCQHSRELPFTFGQGTKVEIKRTVAAPSVFIF

PPSDEQLKSGTASVVCLLNNFYPREAKVQWKVDNALQSGNSQESVTEQDSKDSTYSLSS

TLTLSKADYEKHKVYACEVTHQGLSSPVTKSFNRGEC

What is claimed is:

1. A humanized 1E9 antibody comprising a humanized light chain variable region and a humanized heavy chain variable region,
   wherein said humanized light chain variable region comprises:
   (i) a mouse CDR L1 as set forth in SEQ ID NO:1, a mouse CDR L2 as set forth in SEQ ID NO:2, a mouse CDR L3 as set forth in SEQ ID NO:3 and
   (ii) a proline or a serine at a position corresponding to Kabat position 12, an alanine at a position corresponding to Kabat position 43, a proline or a serine at a position corresponding to Kabat position 60, a threonine at a position corresponding to Kabat position 74, an asparagine or a serine at a position corresponding to Kabat position 76, an asparagine or a serine at a position corresponding to Kabat position 77, an isoleucine or a leucine at a position corresponding to Kabat position 78, a serine or an alanine at a position corresponding to Kabat position 80, a glutamine at a position corresponding to Kabat position 100 and a valine at a position corresponding to Kabat position 104; and
   wherein said humanized heavy chain variable region comprises:
   (i) a mouse CDR H1 as set forth in SEQ ID NO:4, a mouse CDR H2 as set forth in SEQ ID NO:5, and a mouse CDR H3 as set forth in SEQ ID NO:6 and
   (ii) a valine at a position corresponding to Kabat position 5, a serine at a position corresponding to Kabat position 7, a valine at a position corresponding to Kabat position 11, a glutamic acid or a lysine at a position corresponding to Kabat position 12, an isoleucine or a valine at a position corresponding to Kabat position 20, an arginine at a position corresponding to Kabat position 38, an alanine or a proline at a position corresponding to Kabat position 40, an arginine at a position corresponding to Kabat position 66, an valine at a position corresponding to Kabat position 67, an isoleucine at a position corresponding to Kabat position 69, an alanine at a position corresponding to Kabat position 71, an lysine at a position corresponding to Kabat position 73, an isoleucine or a threonine at a position corresponding to Kabat position 75, an arginine or a lysine at a position corresponding to Kabat position 83 and a threonine at a position corresponding to Kabat position 87.

2. The humanized 1E9 antibody of claim 1, wherein said humanized heavy chain variable region comprises a valine at a position corresponding to Kabat position 5, a serine at a position corresponding to Kabat position 7, a valine at a position corresponding to Kabat position 11, a glutamic acid at a position corresponding to Kabat position 12, a valine at a position corresponding to Kabat position 20, an arginine at a position corresponding to Kabat position 38, an alanine at a position corresponding to Kabat position 40, a methionine at a position corresponding to Kabat position 48, an arginine at a position corresponding to Kabat position 66, a valine at a position corresponding to Kabat position 67, an isoleucine at a position corresponding to Kabat position 69, an alanine at a position corresponding to Kabat position 71, a lysine at a position corresponding to Kabat position 73, a threonine at a position corresponding to Kabat position 75, a glutamic acid at a position corresponding to Kabat position 81, an arginine at a position corresponding to Kabat position 83, a threonine at a position corresponding to Kabat position 87, and a valine at a position corresponding to Kabat position 89.

3. The humanized 1E9 antibody of claim 1, wherein said humanized heavy chain variable region comprises the sequence of SEQ ID NO:7.

4. The humanized 1E9 antibody of claim 1, wherein said antibody is capable of binding a CD73 antigen at a pH of about 6.3.

5. The humanized 1E9 antibody of claim 1 bound to a CD73 antigen.

6. The humanized 1E9 antibody of claim 5, wherein said CD73 antigen forms part of a cell.

7. The humanized 1E9 antibody of claim 6, wherein said cell is a cancer cell.

8. An isolated nucleic acid encoding a humanized 1E9 antibody of claim 1.

9. The isolated nucleic acid of claim 8, wherein said isolated nucleic acid comprises SEQ ID NO:52 or SEQ ID NO:54.

10. A pharmaceutical composition comprising a therapeutically effective amount of a humanized 1E9 antibody of claim 1 and a pharmaceutically acceptable excipient.

11. A method of treating cancer in a subject in need thereof, said method comprising administering to said subject a therapeutically effective amount of a humanized 1E9 antibody of claim 1, thereby treating cancer in said subject.

12. A humanized 1E9 antibody bound to a CD73 antigen at a pH of less than about 7.5, wherein said humanized light chain variable region comprises an isoleucine at a position corresponding to Kabat position 2, a leucine at a position corresponding to Kabat position 4, a serine or alanine at a position corresponding to Kabat position 9, a serine or threonine at a position corresponding to Kabat position 10, a leucine at a position corresponding to Kabat position 11, a serine at a position corresponding to Kabat position 14, a glycine at a position corresponding to Kabat position 16, an arginine at a position corresponding to Kabat position 18, a threonine at a position corresponding to Kabat position 20 and a glutamine at a position corresponding to Kabat position 42; and wherein said humanized heavy chain variable region comprises a glutamine at a position corresponding to Kabat position 1, a serine at a position corresponding to Kabat position 17, a methionine or valine at a position corresponding to Kabat position 20, a alanine at a position corresponding to Kabat position 24, a valine at a position corresponding to Kabat position 37, an arginine or alanine at a position corresponding to Kabat position 40, a proline at a position corresponding to Kabat position 41, a glutamine at a position corresponding to Kabat position 43, a glycine at a position corresponding to Kabat position 44, a threonine at a position corresponding to Kabat position 70, a threonine at a position corresponding to Kabat position 75, a methionine at a position corresponding to Kabat position 80, a threonine or arginine at a position corresponding to Kabat position 83, a serine at a position corresponding to Kabat position 84, a glutamic acid at a position corresponding to Kabat position 85, and a valine at a position corresponding to Kabat position 89.

13. The humanized 1E9 antibody of claim 12, wherein said pH is from about 6.0 to about 7.0.

14. The humanized 1E9 antibody of claim 12, wherein said antibody comprises a humanized light chain variable region comprising the sequence of SEQ ID NO:36 or SEQ ID NO:37.

15. The humanized 1E9 antibody of claim 12, wherein said antibody comprises a humanized heavy chain variable region comprising the sequence of SEQ ID NO:7.

* * * * *

SEQUENCE LISTING

```
<160> NUMBER OF SEQ ID NOS: 55

<210> SEQ ID NO 1
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 1

Arg Ala Ser Lys Asn Val Ser Thr Ser Gly Tyr Ser Tyr Met His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide
```

```
<400> SEQUENCE: 2

Leu Ala Ser Asn Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 3

Gln His Ser Arg Glu Leu Pro Phe Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 4

Gly Tyr Thr Phe Thr Ser Tyr Trp Ile Thr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 5

Pro Gly Ser Gly Asn Thr Asn Tyr Asn Glu Lys Phe Lys Thr
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 6

Glu Gly Gly Leu Thr Thr Glu Asp Tyr Ala Leu Asp Tyr
1               5                   10

<210> SEQ ID NO 7
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 7

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Gly Leu Glu Trp Met
        35                  40                  45

Gly Asp Ile Tyr Pro Gly Ser Gly Asn Thr Asn Tyr Asn Glu Lys Phe
    50                  55                  60
```

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val
        115                 120

<210> SEQ ID NO 8
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 8
gccatccagt tgacccagtc tccatcctcc ctgtctgcat ctgtaggaga cagagtcacc    60
atcacttgca gggccagcaa aaatgtcagt acatctggct atagttatat gcactggtat   120
cagcagaaac cagggaaagc tcctaagctc ctgatctatc ttgcatccaa cctagaatct   180
gggatcccac ctcggttcag tggcagcggg tatggaacag attttaccct cacaattaat   240
aacatagaat ctgaggatgc tgcatattac ttctgtcagc acagtaggga gcttccattc   300
acgttcggcc aagggaccaa ggtggaaatc aaa                                333

<210> SEQ ID NO 9
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 9
gaaattgtgc tgactcagtc tccagacttt cagtctgtga ctccaaagga gaaagtcacc    60
atcacctgca gggccagcaa aaatgtcagt acatctggct atagttatat gcactggtat   120
cagcagaaac cagggaaagc tcctaagctc ctgatctatc ttgcatccaa cctagaatct   180
gggatcccac ctcgattcag tggcagcggg tatggaacag attttaccct cacaattaat   240
aacatagaat ctgaggatgc tgcatattac ttctgtcagc acagtaggga gcttccattc   300
acgttcggcc aagggaccaa ggtggaaatc aaa                                333

<210> SEQ ID NO 10
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 10
gaaattgtgc tgactcagtc tccagacttt cagtctgtga ctccaaagga gaaagtcacc    60
atcacctgca gggccagcaa aaatgtcagt acatctggct atagttatat gcactggtat   120
cagcagaaac cagggaaagc tcctaagctc ctgatctatc ttgcatccaa cctagaatct   180
gggatcccac ctcgattcag tggcagcggg tatggaacag attttaccct cacaattaat   240
aacatagaat ctgaggatgc tgcatattac ttctgtcagc acagtaggga gcttccattc   300
acgttcggcc aagggaccaa ggtggaaatc aaa                                333

<210> SEQ ID NO 11
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 11

| | | | | | |
|---|---|---|---|---|---|
| gaaattgtgc | tgactcagtc | tccagacttt | cagtctgtga | ctccaaagga | gaaagtcacc | 60 |
| atcacctgca | gggccagcaa | aaatgtcagt | acatctggct | atagttatat | gcactggtat | 120 |
| cagcagaaac | cagggaaagc | tcctaagctc | ctgatctatc | ttgcatccaa | cctagaatct | 180 |
| gggatcccac | ctcgattcag | tggcagcggg | tatggaacag | attttaccct | cacaattaat | 240 |
| aacatagaat | ctgaggatgc | tgcatattac | ttctgtcagc | acagtaggga | gcttccattc | 300 |
| acgttcggcc | aagggaccaa | ggtggaaatc | aaa | | | 333 |

<210> SEQ ID NO 12
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 12

| | | | | | |
|---|---|---|---|---|---|
| gatgttgtga | tgactcagtc | tccactctcc | ctgcccgtca | cccttggaca | gccggcctcc | 60 |
| atctcctgca | gggccagcaa | aaatgtcagt | acatctggct | atagttatat | gcactggtac | 120 |
| cagcagaaac | ctggccaggc | tcccaggctc | ctcatctatc | ttgcatccaa | cctagaatct | 180 |
| gggatcccac | ctcgattcag | tggcagcggg | tatggaacag | attttaccct | cacaattaat | 240 |
| aacatagaat | ctgaggatgc | tgcatattac | ttctgtcagc | acagtaggga | gcttccattc | 300 |
| acgttcggcc | aagggaccaa | ggtggaaatc | aaa | | | 333 |

<210> SEQ ID NO 13
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 13

| | | | | | |
|---|---|---|---|---|---|
| gccatccagt | tgacccagtc | tccatcctcc | ctgtctgcat | ctgtaggaga | cagagtcacc | 60 |
| atcacttgca | gggccagcaa | aaatgtcagt | acatctggct | atagttatat | gcactggtac | 120 |
| cagcagaaac | ctggccaggc | tcccaggctc | ctcatctatc | ttgcatccaa | cctagaatct | 180 |
| ggggtcccct | cgaggttcag | tggcagtgga | tctgggacag | atttcacctt | taccatcagt | 240 |
| agcctggaag | ctgaagatgc | tgcaacatat | tactgtcagc | acagtaggga | gcttccattc | 300 |
| acgttcggcc | aagggaccaa | ggtggaaatc | aaa | | | 333 |

<210> SEQ ID NO 14
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 14

| | | | | | |
|---|---|---|---|---|---|
| gaaattgtgt | tgacacagtc | tccagccacc | ctgtctttgt | ctccagggga | aagagccacc | 60 |
| ctctcctgca | gggccagcaa | aaatgtcagt | acatctggct | atagttatat | gcactggtac | 120 |

| | |
|---|---|
| cagcagaaac ctggccaggc tcccaggctc ctcatctatc ttgcatccaa cctagaatct | 180 |
| gggatcccac ctcgattcag tggcagcggg tatggaacag attttaccct cacaattaat | 240 |
| aacatagaat ctgaggatgc tgcatattac ttctgtcagc acagtaggga gcttccattc | 300 |
| acgttcggcc aagggaccaa ggtggaaatc aaa | 333 |

<210> SEQ ID NO 15
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 15

| | |
|---|---|
| gaaattgtgt tgacacagtc tccagccacc ctgtctttgt ctccagggga aagagccacc | 60 |
| ctctcctgca gggccagcaa aaatgtcagt acatctggct atagttatat gcactggtac | 120 |
| cagcagaaac ctggccaggc tcccaggctc ctcatctatc ttgcatccaa cctagaatct | 180 |
| gggatcccac ctcgattcag tggcagcggg tatggaacag attttaccct cacaattaat | 240 |
| aacatagaat ctgaggatgc tgcatattac ttctgtcagc acagtaggga gcttccattc | 300 |
| acgttcggcc aagggaccaa ggtggaaatc aaa | 333 |

<210> SEQ ID NO 16
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 16

| | |
|---|---|
| gaaattgtgt tgacacagtc tccagccacc ctgtctttgt ctccagggga aagagccacc | 60 |
| ctctcctgca gggccagcaa aaatgtcagt acatctggct atagttatat gcactggtac | 120 |
| cagcagaaac ctggccaggc tcccaggctc ctcatctatc ttgcatccaa cctagaatct | 180 |
| gggatcccac ctcgattcag tggcagcggg tatggaacag attttaccct cacaattaat | 240 |
| aacatagaat ctgaggatgc tgcatattac ttctgtcagc acagtaggga gcttccattc | 300 |
| acgttcggcc aagggaccaa ggtggaaatc aaa | 333 |

<210> SEQ ID NO 17
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 17

| | |
|---|---|
| gaaattgtgt tgacacagtc tccagccacc ctgtctttgt ctccagggga aagagccacc | 60 |
| ctctcctgca gggccagcaa aaatgtcagt acatctggct atagttatat gcactggtac | 120 |
| cagcagaaac ctggccaggc tcccaggctc ctcatctatc ttgcatccaa cctagaatct | 180 |
| gggatcccac ctcgattcag tggcagcggg tatggaacag attttaccct cacaattaat | 240 |
| aacatagaat ctgaggatgc tgcatattac ttctgtcagc acagtaggga gcttccattc | 300 |
| acgttcggcc aagggaccaa ggtggaaatc aaa | 333 |

<210> SEQ ID NO 18
<211> LENGTH: 366
<212> TYPE: DNA

<213> ORGANISM: Artificial Sequence
<220> FEATURE:
<223> OTHER INFORMATION: Synthetic polynucleotide

<400> SEQUENCE: 18

| | |
|---|---|
| caggttcagc tggtgcagtc tggagctgag gtggagaagc ctggggcctc agtgaaggtc | 60 |
| tcctgcaagg cttctggcta caccttcacc agctactgga taacctgggt gcgacaggcc | 120 |
| cctggacaag gcttgagtg gatgggtgat atttatcctg gtagtggtaa tactaactac | 180 |
| aatgagaagt tcaagaccag agtcacgatt accgcggaca aatccacgag cacagcctac | 240 |
| atggagctga gcagcctgag atctgaggac acggccgtgt attactgtgc aaaagaggga | 300 |
| ggtcttacta cggaggatta tgctttggac tactggggcc agggaacgct ggtcaccgtc | 360 |
| agctca | 366 |

<210> SEQ ID NO 19
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 19

| | |
|---|---|
| caggttcagc tggtgcagtc tggagctgag gtggagaagc ctggggcctc agtgaaggtc | 60 |
| tcctgcaagg cttctggcta caccttcacc agctactgga taacctgggt gcgacaggcc | 120 |
| cctggacaag gcttgagtg gatgggtgat atttatcctg gtagtggtaa tactaactac | 180 |
| aatgagaagt tcaagaccag agtcacgatt accgcggaca aatccacgag cacagcctac | 240 |
| atggagctga gcagcctgag atctgaggac acggccgtgt attactgtgc aaaagaggga | 300 |
| ggtcttacta cggaggatta tgctttggac tactggggcc agggaacgct ggtcaccgtc | 360 |
| agctca | 366 |

<210> SEQ ID NO 20
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 20

| | |
|---|---|
| caggttcagc tggtgcagtc tggagctgag gtgaagaagc ctggggcctc agtgaaggtc | 60 |
| tcctgcaagg cttctggcta caccttcacc agctactgga taacctgggt gcgacaggct | 120 |
| cgtggacaac gccttgagtg gataggtgat atttatcctg gtagtggtaa tactaactac | 180 |
| aatgagaagt tcaagaccag agtcacgatt accgcggaca aatccacgag cacagcctac | 240 |
| atggagctga gcagcctgag atctgaggac acggccgtgt attactgtgc aaaagaggga | 300 |
| ggtcttacta cggaggatta tgctttggac tactggggcc agggaacgct ggtcaccgtc | 360 |
| agctca | 366 |

<210> SEQ ID NO 21
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 21

| | |
|---|---|
| gaggtccagc tggtacagtc tggggctgag gtgaagaagc ctggggctac agtgaaaatc | 60 |

```
tcctgcaagg tttctggcta caccttcacc agctactgga taacctggat ccgccagccc    120
ccagggaagg ggctggagtg gattggtgat atttatcctg gtagtggtaa tactaactac    180
aatgagaagt tcaagaccag agtcaccatc tcagccgaca gtccatcag caccgcctac     240 ctgcagtgga gcagcctgaa ggcctcggac accgccatgt attactgtgc aaaagaggga    300
ggtcttacta cggaggatta tgctttggac tactggggcc agggaacgct ggtcaccgtc    360
agctca                                                               366

<210> SEQ ID NO 22
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 22
gaggtccagc tggtacagtc tggggctgag gtgaagaagc ctggggctac agtgaaaatc    60
tcctgcaagg tttctggcta caccttcacc agctactgga taacctggat ccgccagccc    120
ccagggaagg ggctggagtg gattggtgat atttatcctg gtagtggtaa tactaactac    180
aatgagaagt tcaagaccag agtcaccatc tcagccgaca gtccatcag caccgcctac     240 ctgcagtgga gcagcctgaa ggcctcggac accgccatgt attactgtgc aaaagaggga    300
ggtcttacta cggaggatta tgctttggac tactggggcc agggaacgct ggtcaccgtc    360
agctca                                                               366

<210> SEQ ID NO 23
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 23
caggttcagc tggtgcagtc tggagctgag gtggagaagc ctggggcctc agtgaaggtc    60
tcctgcaagg cttctggcta caccttcacc agctactgga taacctgggt gcgacaggcc    120
cctggacaag ggcttgagtg gatgggtgat atttatcctg gtagtggtaa tactaactac    180
aatgagaagt tcaagaccag agtcacgatt accgcggaca atccacgag cacagcctac     240 atggagctga gcagcctgag atctgaggac acggccgtgt attactgtgc aaaagaggga    300
ggtcttacta cggaggatta tgctttggac tactggggcc agggaacgct ggtcaccgtc    360
agctca                                                               366

<210> SEQ ID NO 24
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 24
caggttcagc tggtgcagtc tggagctgag gtggagaagc ctggggcctc agtgaaggtc    60
tcctgcaagg cttctggcta caccttcacc agctactgga taacctgggt gcgacaggcc    120
cctggacaag ggcttgagtg gatgggtgat atttatcctg gtagtggtaa tactaactac    180
aatgagaagt tcaagaccag agtcacgatt accgcggaca atccacgag cacagcctac     240
```

```
atggagctga gcagcctgag atctgaggac acggccgtgt attactgtgc aaaagaggga      300
ggtcttacta cggaggatta tgctttggac tactggggcc agggaacgct ggtcaccgtc      360
agctca                                                                 366

<210> SEQ ID NO 25
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 25
gaggtccagc tggtacagtc tggggctgag gtgaagaagc ctggggctac agtgaaaatc       60
tcctgcaagg tttctggcta caccttcacc agctactgga taacctgggt gcgacaggcc      120
cctggacaag gcttgagtg gatgggtgat atttatcctg gtagtggtaa tactaactac       180
aatgagaagt tcaagaccag agtcacgatt accgcggaca atccacgag cacagcctac       240 atggagctga gcagcctgag atctgaggac acggccgtgt attactgtgc aaaagaggga      300
ggtcttacta cggaggatta tgctttggac tactggggcc agggaacgct ggtcaccgtc      360
agctca                                                                 366

<210> SEQ ID NO 26
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 26
caggttcagc tggtgcagtc tggagctgag gtgaagaagc ctggggcctc agtgaaggtc       60
tcctgcaagg cttctggcta caccttcacc agctactgga taacctgggt gcgacaggct      120
cgtggacaac gccttgagtg gataggtgat atttatcctg gtagtggtaa tactaactac      180
aatgagaagt tcaagaccag agtcacgatt accgcggaca atccacgag cacagcctac       240 atggagctga gcagcctgag atctgaggac acggccgtgt attactgtgc aaaagaggga      300
ggtcttacta cggaggatta tgctttggac tactggggcc agggaacgct ggtcaccgtc      360
agctca                                                                 366

<210> SEQ ID NO 27
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 27
gaggtccagc tggtacagtc tggggctgag gtgaagaagc ctggggctac agtgaaaatc       60
tcctgcaagg tttctggcta caccttcacc agctactgga taacctggat ccgccagccc      120
ccagggaagg gcctggagtg gattggtgat atttatcctg gtagtggtaa tactaactac      180
aatgagaagt tcaagaccag agtcaccatc tcagccgaca gtccatcag caccgcctac       240 ctgcagtgga gcagcctgaa ggcctcggac accgccatgt attactgtgc aaaagaggga      300
ggtcttacta cggaggatta tgctttggac tactggggcc agggaacgct ggtcaccgtc      360
agctca                                                                 366
```

<210> SEQ ID NO 28
<211> LENGTH: 333
<212> TYPE: DNA
<213> ORGANISM: Artificial Sequence
<220> FEATURE:
<223> OTHER INFORMATION: Synthetic polynucleotide

<400> SEQUENCE: 28

```
gacattgtgc tgacacagtc tcctgcttcc ttagctgtat ctctggggca gagggccacc      60
atctcatgca gggccagcaa aaatgtcagt acatctggct atagttatat gcactggtac     120
caacagaaac caggacagcc acccaaactc ctcatctatc ttgcatccaa cctagaatct     180
ggggtcccta ccaggttcag tggcagtggg tctgggacag acttcaccct caacatccat     240
cctgtggagg aggaggatgc tgcaacctat tactgtcagc acagtaggga gcttccattc     300
acgttcggct cggggacaaa gttggaaata aaa                                  333
```

<210> SEQ ID NO 29
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 29

```
caggtccaac tgcagcagcc tggggctgag cttgtgaagc ctggggcttc agtgaagatg      60
tcctgcaagg cttctggcta ccttcacc agctactgga taacctgggt gaagcagagg      120
cctggacaag gccttgagtg gattggagat atttatcctg gtagtggtaa tactaactac     180
aatgagaagt tcaagaccaa ggccacactg actgtagaca catcctccag cacagcctac     240
atgcagctca gcagcctgac atctgaggac tctgcggtct attactgtgc aaaagaggga     300
ggtcttacta cggaggatta tgctttggac tactggggcc agggaacgct ggtcaccgtc     360
agctca                                                               366
```

<210> SEQ ID NO 30
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 30

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Asn Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Thr
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys
            100                 105                 110
```

<210> SEQ ID NO 31
<211> LENGTH: 111

```
<212> TYPE: PRT
<213> ORGANISM: Artificial Sequence
<220> FEATURE:
<223> OTHER INFORMATION: Synthetic polypeptide

<400> SEQUENCE: 31

Ala Ile Gln Leu Thr Gln Ser Pro Ser Ser Leu Ser Ala Ser Val Gly
1               5                   10                  15

Asp Arg Val Thr Ile Thr Cys Arg Ala Ser Lys Asn Val Ser Thr Ser
            20                  25                  30

Gly Tyr Ser Tyr Met His Trp Tyr Gln Gln Lys Pro Gly Lys Ala Pro
        35                  40                  45

Lys Leu Leu Ile Tyr Leu Ala Ser Asn Leu Glu Ser Gly Ile Pro Pro
    50                  55                  60

Arg Phe Ser Gly Ser Gly Tyr Gly Thr Asp Phe Thr Leu Thr Ile Asn
65                  70                  75                  80

Asn Ile Glu Ser Glu Asp Ala Ala Tyr Tyr Phe Cys Gln His Ser Arg
                85                  90                  95

Glu Leu Pro Phe Thr Phe Gly Gln Gly Thr Lys Val Glu Ile Lys
            100                 105                 110

<210> SEQ ID NO 32
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 32

Glu Ile Val Leu Thr Gln Ser Pro Asp Phe Gln Ser Val Thr Pro Lys
1               5                   10                  15

Glu Lys Val Thr Ile Thr Cys Arg Ala Ser Lys Asn Val Ser Thr Ser
            20                  25                  30

Gly Tyr Ser Tyr Met His Trp Tyr Gln Gln Lys Pro Gly Lys Ala Pro
        35                  40                  45

Lys Leu Leu Ile Tyr Leu Ala Ser Asn Leu Glu Ser Gly Ile Pro Pro
    50                  55                  60

Arg Phe Ser Gly Ser Gly Tyr Gly Thr Asp Phe Thr Leu Thr Ile Asn
65                  70                  75                  80

Asn Ile Glu Ser Glu Asp Ala Ala Tyr Tyr Phe Cys Gln His Ser Arg
                85                  90                  95

Glu Leu Pro Phe Thr Phe Gly Gln Gly Thr Lys Val Glu Ile Lys
            100                 105                 110

<210> SEQ ID NO 33
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 33

Glu Ile Val Leu Thr Gln Ser Pro Asp Phe Gln Ser Val Thr Pro Lys
1               5                   10                  15

Glu Lys Val Thr Ile Thr Cys Arg Ala Ser Lys Asn Val Ser Thr Ser
            20                  25                  30

Gly Tyr Ser Tyr Met His Trp Tyr Gln Gln Lys Pro Gly Lys Ala Pro
        35                  40                  45

Lys Leu Leu Ile Tyr Leu Ala Ser Asn Leu Glu Ser Gly Ile Pro Pro
```

```
                50                  55                  60

Arg Phe Ser Gly Ser Gly Tyr Gly Thr Asp Phe Thr Leu Thr Ile Asn
 65                  70                  75                  80

Asn Ile Glu Ser Glu Asp Ala Ala Tyr Tyr Phe Cys Gln His Ser Arg
                 85                  90                  95

Glu Leu Pro Phe Thr Phe Gly Gln Gly Thr Lys Val Glu Ile
            100                 105                 110

<210> SEQ ID NO 34
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 34

Glu Ile Val Leu Thr Gln Ser Pro Asp Phe Gln Ser Val Thr Pro Lys
 1               5                  10                  15

Glu Lys Val Thr Ile Thr Cys Arg Ala Ser Lys Asn Val Ser Thr Ser
                20                  25                  30

Gly Tyr Ser Tyr Met His Trp Tyr Gln Gln Lys Pro Gly Lys Ala Pro
            35                  40                  45

Lys Leu Leu Ile Tyr Leu Ala Ser Asn Leu Glu Ser Gly Ile Pro Pro
 50                  55                  60

Arg Phe Ser Gly Ser Gly Tyr Gly Thr Asp Phe Thr Leu Thr Ile Asn
 65                  70                  75                  80

Asn Ile Glu Ser Glu Asp Ala Ala Tyr Tyr Phe Cys Gln His Ser Arg
                 85                  90                  95

Glu Leu Pro Phe Thr Phe Gly Gln Gly Thr Lys Val Glu Ile Lys
            100                 105                 110

<210> SEQ ID NO 35
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 35

Asp Val Val Met Thr Gln Ser Pro Leu Ser Leu Pro Val Thr Leu Gly
 1               5                  10                  15

Gln Pro Ala Ser Ile Ser Cys Arg Ala Ser Lys Asn Val Ser Thr Ser
                20                  25                  30

Gly Tyr Ser Tyr Met His Trp Tyr Gln Gln Lys Pro Gly Gln Ala Pro
            35                  40                  45

Arg Leu Leu Ile Tyr Leu Ala Ser Asn Leu Glu Ser Gly Ile Pro Pro
 50                  55                  60

Arg Phe Ser Gly Ser Gly Tyr Gly Thr Asp Phe Thr Leu Thr Ile Asn
 65                  70                  75                  80

Asn Ile Glu Ser Glu Asp Ala Ala Tyr Tyr Phe Cys Gln His Ser Arg
                 85                  90                  95

Glu Leu Pro Phe Thr Phe Gly Gln Gly Thr Lys Val Glu Ile Lys
            100                 105                 110

<210> SEQ ID NO 36
<211> LENGTH: 111
<212> TYPE: PRT
<213> ORGANISM: Artificial Sequence
<220> FEATURE:
```

<223> OTHER INFORMATION: Synthetic polypeptide

<400> SEQUENCE: 36

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Lys Asn Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Glu Ala Glu Asp Ala Ala Thr Tyr Tyr Cys Gln His Ser Arg
                85                  90                  95

Glu Leu Pro Phe Thr Phe Gly Gln Gly Thr Lys Val Glu Ile Lys
            100                 105                 110
```

<210> SEQ ID NO 37
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 37

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Asn Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Ile Pro Pro
    50                  55                  60

Arg Phe Ser Gly Ser Gly Tyr Gly Thr Asp Phe Thr Leu Thr Ile Asn
65                  70                  75                  80

Asn Ile Glu Ser Glu Asp Ala Ala Tyr Tyr Phe Cys Gln His Ser Arg
                85                  90                  95

Glu Leu Pro Phe Thr Phe Gly Gln Gly Thr Lys Val Glu Ile Lys
            100                 105                 110
```

<210> SEQ ID NO 38
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 38

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Asn Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Ile Pro Pro
    50                  55                  60

Arg Phe Ser Gly Ser Gly Tyr Gly Thr Asp Phe Thr Leu Thr Ile Asn
```

```
                65                  70                  75                  80
Asn Ile Glu Ser Glu Asp Ala Ala Tyr Tyr Phe Cys Gln His Ser Arg
                    85                  90                  95

Glu Leu Pro Phe Thr Phe Gly Gln Gly Thr Lys Val Glu Ile Lys
                100                 105                 110

<210> SEQ ID NO 39
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Asn Val Ser Thr Ser
                20                  25                  30

Gly Tyr Ser Tyr Met His Trp Tyr Gln Gln Lys Pro Gly Gln Ala Pro
            35                  40                  45

Arg Leu Leu Ile Tyr Leu Ala Ser Asn Leu Glu Ser Gly Ile Pro Pro
        50                  55                  60

Arg Phe Ser Gly Ser Gly Tyr Gly Thr Asp Phe Thr Leu Thr Ile Asn
65                  70                  75                  80

Asn Ile Glu Ser Glu Asp Ala Ala Tyr Tyr Phe Cys Gln His Ser Arg
                    85                  90                  95

Glu Leu Pro Phe Thr Phe Gly Gln Gly Thr Lys Val Glu Ile Lys
                100                 105                 110

<210> SEQ ID NO 40
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Asn Val Ser Thr Ser
                20                  25                  30

Gly Tyr Ser Tyr Met His Trp Tyr Gln Gln Lys Pro Gly Gln Ala Pro
            35                  40                  45

Arg Leu Leu Ile Tyr Leu Ala Ser Asn Leu Glu Ser Gly Ile Pro Pro
        50                  55                  60

Arg Phe Ser Gly Ser Gly Tyr Gly Thr Asp Phe Thr Leu Thr Ile Asn
65                  70                  75                  80

Asn Ile Glu Ser Glu Asp Ala Ala Tyr Tyr Phe Cys Gln His Ser Arg
                    85                  90                  95

Glu Leu Pro Phe Thr Phe Gly Gln Gly Thr Lys Val Glu Ile Lys
                100                 105                 110

<210> SEQ ID NO 41
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 41
```

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Lys Gln Arg Pro Gly Gln Gly Leu Glu Trp Ile
        35                  40                  45

Gly Asp Ile Tyr Pro Gly Ser Gly Asn Thr Asn Tyr Asn Glu Lys Phe
    50                  55                  60

Lys Thr Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val Ser Ser
        115                 120

<210> SEQ ID NO 42
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 42

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Gly Leu Glu Trp Met
        35                  40                  45

Gly Asp Ile Tyr Pro Gly Ser Gly Asn Thr Asn Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val Ser Ser
        115                 120

<210> SEQ ID NO 43
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 43

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Gly Leu Glu Trp Met
        35                  40                  45

Gly Asp Ile Tyr Pro Gly Ser Gly Asn Thr Asn Tyr Asn Glu Lys Phe
```

```
            50                  55                  60
Lys Thr Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Glu Gly Gly Leu Thr Thr Glu Asp Tyr Ala Leu Asp Tyr Trp
             100                 105                 110

Gly Gln Gly Thr Leu Val Thr Val Ser Ser
        115                 120

<210> SEQ ID NO 44
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 44

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Trp Ile Thr Trp Val Arg Gln Ala Arg Gly Gln Arg Leu Glu Trp Ile
         35                  40                  45

Gly Asp Ile Tyr Pro Gly Ser Gly Asn Thr Asn Tyr Asn Glu Lys Phe
     50                  55                  60

Lys Thr Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Glu Gly Gly Leu Thr Thr Glu Asp Tyr Ala Leu Asp Tyr Trp
             100                 105                 110

Gly Gln Gly Thr Leu Val Thr Val Ser Ser
        115                 120

<210> SEQ ID NO 45
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 45

Glu Val Gln Leu Val Gln Ser Gly Ala Glu Val Lys Lys Pro Gly Ala
 1               5                  10                  15

Thr Val Lys Ile Ser Cys Lys Val Ser Gly Tyr Thr Phe Thr Ser Tyr
             20                  25                  30

Trp Ile Thr Trp Ile Arg Gln Pro Pro Gly Lys Gly Leu Glu Trp Ile
         35                  40                  45

Gly Asp Ile Tyr Pro Gly Ser Gly Asn Thr Asn Tyr Asn Glu Lys Phe
     50                  55                  60

Lys Thr Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Lys Glu Gly Gly Leu Thr Thr Glu Asp Tyr Ala Leu Asp Tyr Trp
             100                 105                 110
```

```
Gly Gln Gly Thr Leu Val Thr Val Ser Ser
            115                 120
```

<210> SEQ ID NO 46
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 46

```
Glu Val Gln Leu Val Gln Ser Gly Ala Glu Val Lys Pro Gly Ala
1               5                   10                  15

Thr Val Lys Ile Ser Cys Lys Val Ser Gly Tyr Thr Phe Thr Ser Tyr
            20                  25                  30

Trp Ile Thr Trp Ile Arg Gln Pro Pro Gly Lys Gly Leu Glu Trp Ile
            35                  40                  45

Gly Asp Ile Tyr Pro Gly Ser Gly Asn Thr Asn Tyr Asn Glu Lys Phe
        50                  55                  60

Lys Thr Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val Ser Ser
            115                 120
```

<210> SEQ ID NO 47
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 47

```
Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Gly Leu Glu Trp Met
            35                  40                  45

Gly Asp Ile Tyr Pro Gly Ser Gly Asn Thr Asn Tyr Asn Glu Lys Phe
        50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val Ser Ser
            115                 120
```

<210> SEQ ID NO 48
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 48

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Pro Gly Gln Gly Leu Glu Trp Met
        35                  40                  45

Gly Asp Ile Tyr Pro Gly Ser Gly Asn Thr Asn Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val Ser Ser
        115                 120

<210> SEQ ID NO 49
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 49

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Ile Thr Trp Val Arg Gln Ala Pro Gly Gln Gly Leu Glu Trp Met
        35                  40                  45

Gly Asp Ile Tyr Pro Gly Ser Gly Asn Thr Asn Tyr Asn Glu Lys Phe
    50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val Ser Ser
        115                 120

<210> SEQ ID NO 50
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Thr Trp Val Arg Gln Ala Arg Gly Gln Arg Leu Glu Trp Ile
        35                  40                  45

Gly Asp Ile Tyr Pro Gly Ser Gly Asn Thr Asn Tyr Asn Glu Lys Phe
            50                  55                  60

Lys Thr Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val Ser Ser
        115                 120

<210> SEQ ID NO 51
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 51

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
                20                  25                  30

Trp Ile Thr Trp Ile Arg Gln Pro Pro Gly Lys Gly Leu Glu Trp Ile
            35                  40                  45

Gly Asp Ile Tyr Pro Gly Ser Gly Asn Thr Asn Tyr Asn Glu Lys Phe
        50                  55                  60

Lys Thr Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Lys Glu Gly Gly Leu Thr Thr Glu Asp Tyr Ala Leu Asp Tyr Trp
            100                 105                 110

Gly Gln Gly Thr Leu Val Thr Val Ser Ser
        115                 120

<210> SEQ ID NO 52
<211> LENGTH: 1438
<212> TYPE: DNA
<213> ORGANISM: Artificial Sequence
<220> FEATURE:
<223> OTHER INFORMATION: Synthetic polynucleotide

<400> SEQUENCE: 52
aagcttgccg ccaccatgga atggtcctgg gtgttcctgt tcttcctgtc cgtgaccacc       60
ggcgtgcact cccaggtgca gctggtgcag tctggcgccg aggtggaaaa gcctggcgcc      120
tctgtgaagg tgtcctgcaa ggcctccggc tacaccttta ccagctactg gatcacctgg      180
gtgcgacagg ctcctggaca gggcctggaa tggatgggcg acatctaccc tggctccggc      240
aacaccaact acaacgagaa gttcaagacc cgcgtgacca tcaccgccga caagtccacc      300
tccaccgcct acatggaact gtcctccctg cggagcgagg acaccgccgt gtactactgt      360
gctaaagagg gcggcctgac caccgaggac tacgccctgg attattgggg ccagggcacc      420
ctcgtgaccg tgtcctctgc ttctaccaag ggcccctccg tgttccctct ggccccttcc      480
agcaagtcta cctctggcgg cacagccgct ctgggctgcc tcgtgaagga ctacttcccc      540
gagcccgtga cagtgtcttg gaactctggc gccctgacca gcggagtgca caccttccct      600

```
gctgtgctgc agtcctccgg cctgtactcc ctgtcctccg tcgtgactgt gccctccagc    660
tctctgggca cccagaccta catctgcaac gtgaaccaca agccctccaa caccaaggtg    720
gacaagaagg tggaacccaa gtcctgcgac aagacccaca cctgtccccc ttgtcctgcc    780
cctgaactgc tgggcggacc ctctgtgttt ctgttccccc caaagcccaa ggacaccctg    840
atgatctccc ggacccccga agtgacctgc gtggtggtgg atgtgtccca cgaggaccct    900
gaagtgaagt tcaattggta cgtggacggc gtggaagtgc acaacgccaa gaccaagcct    960
agagaggaac agtaccagtc cacctaccgg gtggtgtccg tgctgaccgt gctgcaccag   1020
gattggctga acggcaaaga gtacaagtgc aaggtgtcca acaaggctct gcctgccccc   1080
atcgaaaaga ccatctccaa ggccaagggc cagccccggg aaccccaggt gtacacactg   1140
ccccctagca gggacgagct gaccaagaac caggtgtccc tgacctgtct cgtgaaaggc   1200
ttctacccct ccgatatcgc cgtggaatgg gagtccaacg gccagcctga gaacaactac   1260
aagaccaccc cccctgtgct ggactccgac ggctcattct ttctgtactc caagctgaca   1320
gtggacaagt cccggtggca gcagggcaac gtgttctcct gcagcgtgat gcacgaggcc   1380
ctgcacaacc actacaccca gaagtccctg tccctgagcc ccggcaagtg atgaattc     1438
```

```

<210> SEQ ID NO 53
<211> LENGTH: 471
<212> TYPE: PRT
<213> ORGANISM: Artificial Sequence
<220> FEATURE:
<223> OTHER INFORMATION: Synthetic polypeptide

<400> SEQUENCE: 53

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Glu Lys
            20                  25                  30

Pro Gly Ala Ser Val Lys Val Ser Cys Lys Ala Ser Gly Tyr Thr Phe
        35                  40                  45

Thr Ser Tyr Trp Ile Thr Trp Val Arg Gln Ala Pro Gly Gln Gly Leu
    50                  55                  60

Glu Trp Met Gly Asp Ile Tyr Pro Gly Ser Gly Asn Thr Asn Tyr Asn
65                  70                  75                  80

Glu Lys Phe Lys Thr Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Lys Glu Gly Gly Leu Thr Thr Glu Asp Tyr Ala Leu
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220
```

```
Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
            245                 250                 255

Glu Leu Leu Gly Gly Pro Ser Val Phe Leu Phe Pro Pro Lys Pro Lys
        260                 265                 270

Asp Thr Leu Met Ile Ser Arg Thr Pro Glu Val Thr Cys Val Val Val
    275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Gln Ser Thr Tyr Arg Val Val Ser Val Leu Thr Val Leu His Gln Asp
            325                 330                 335

Trp Leu Asn Gly Lys Glu Tyr Lys Cys Lys Val Ser Asn Lys Ala Leu
        340                 345                 350

Pro Ala Pro Ile Glu Lys Thr Ile Ser Lys Ala Lys Gly Gln Pro Arg
    355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
        420                 425                 430

Lys Leu Thr Val Asp Lys Ser Arg Trp Gln Gln Gly Asn Val Phe Ser
    435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 54
<211> LENGTH: 739
<212> TYPE: DNA
<213> ORGANISM: Artificial Sequence
<220> FEATURE:
<223> OTHER INFORMATION: Synthetic polynucleotide

<400> SEQUENCE: 54
aagcttgccg ccaccatgtc cgtgcctacc caggtgctgg gactgctgct gctgtggctg    60
accgatgcca gatgcgagat cgtgctgacc cagtcccctg ccaccctgtc actgtctcca   120
ggcgagagag ccaccctgag ctgccgggcc tccaagaacg tgtccacctc cggctactcc   180
tacatgcact ggtatcagca gaagcccggc caggccccca ctgctgat ctacctggcc    240 tccaacctgg aatccggcat ccccctaga ttctccggct ctggctacgg caccgacttc    300
accctgacca tcaacaacat cgagtccgag gacgccgcct actacttctg ccagcactcc   360
agagagctgc ccttcacctt tggccagggc accaaggtgg aaatcaagcg gaccgtggcc   420
gctccctccg tgttcatctt cccaccttcc gacgagcagc tgaagtccgg caccgcttct   480
gtcgtgtgcc tgctgaacaa cttctacccc cgcgaggcca aggtgcagtg gaaggtggac   540
aacgccctgc agtccggcaa ctcccaggaa tccgtgaccg agcaggactc caaggacagc   600
```

```
acctactccc tgtcctctac cctgaccctg tccaaggccg actacgagaa gcacaaggtg    660
tacgcctgcg aagtgaccca ccagggcctg tctagccccg tgaccaagtc tttcaaccgg    720
ggcgagtgct gatgaattc                                                 739
```

<210> SEQ ID NO 55
<211> LENGTH: 238
<212> TYPE: PRT
<213> ORGANISM: Artificial Sequence
<220> FEATURE:
<223> OTHER INFORMATION: Synthetic polypeptide

<400> SEQUENCE: 55

```
Met Ser Val Pro Thr Gln Val Leu Gly Leu Leu Leu Leu Trp Leu Thr
1               5                   10                  15

Asp Ala Arg Cys Glu Ile Val Leu Thr Gln Ser Pro Ala Thr Leu Ser
            20                  25                  30

Leu Ser Pro Gly Glu Arg Ala Thr Leu Ser Cys Arg Ala Ser Lys Asn
        35                  40                  45

Val Ser Thr Ser Gly Tyr Ser Tyr Met His Trp Tyr Gln Gln Lys Pro
    50                  55                  60

Gly Gln Ala Pro Arg Leu Leu Ile Tyr Leu Ala Ser Asn Leu Glu Ser
65                  70                  75                  80

Gly Ile Pro Pro Arg Phe Ser Gly Ser Gly Tyr Gly Thr Asp Phe Thr
                85                  90                  95

Leu Thr Ile Asn Asn Ile Glu Ser Glu Asp Ala Ala Tyr Tyr Phe Cys
            100                 105                 110

Gln His Ser Arg Glu Leu Pro Phe Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```